(12) United States Patent
Entcheva et al.

(10) Patent No.: US 11,680,904 B2
(45) Date of Patent: Jun. 20, 2023

(54) AUTOMATED SYSTEM FOR HIGH-THROUGHPUT ALL-OPTICAL DYNAMIC ELECTROPHYSIOLOGY

(71) Applicant: The George Washington University, Washington, DC (US)

(72) Inventors: Emilia Entcheva, Washington, DC (US); Aleksandra Klimas, Alexandria, VA (US)

(73) Assignee: The George Washington University, Washington, DC (US)

( * ) Notice: Subject to any disclaimer, the term of this patent is extended or adjusted under 35 U.S.C. 154(b) by 1210 days.

(21) Appl. No.: 16/098,795

(22) PCT Filed: May 2, 2017

(86) PCT No.: PCT/US2017/030626
§ 371 (c)(1),
(2) Date: Nov. 2, 2018

(87) PCT Pub. No.: WO2017/192579
PCT Pub. Date: Nov. 9, 2017

(65) Prior Publication Data
US 2019/0137398 A1 May 9, 2019

Related U.S. Application Data

(60) Provisional application No. 62/330,741, filed on May 2, 2016.

(51) Int. Cl.
| | | |
|---|---|---|
| *G01N 21/00* | (2006.01) | |
| *G01N 21/64* | (2006.01) | |
| *G01N 33/50* | (2006.01) | |
| *C12N 13/00* | (2006.01) | |
| *C12N 5/077* | (2010.01) | |

(52) U.S. Cl.
CPC ....... *G01N 21/6452* (2013.01); *C12N 5/0657* (2013.01); *C12N 13/00* (2013.01); *G01N 33/50* (2013.01); *G01N 33/502* (2013.01); *G01N 21/6428* (2013.01); *G01N 2021/6439* (2013.01)

(58) Field of Classification Search
None
See application file for complete search history.

(56) References Cited

U.S. PATENT DOCUMENTS

| | | |
|---|---|---|
| 2001/0005586 A1 | 6/2001 | Palsson et al. |
| 2009/0294692 A1 | 12/2009 | Bourke, Jr. et al. |
| 2011/0318775 A1 | 12/2011 | Mercola et al. |
| 2013/0274838 A1* | 10/2013 | Entcheva ............. A61N 1/3629 607/88 |
| 2015/0328313 A1 | 11/2015 | Chow et al. |
| 2016/0069876 A1 | 3/2016 | Cohen et al. |

FOREIGN PATENT DOCUMENTS

| | | |
|---|---|---|
| JP | 2016176949 A | 10/2016 |
| WO | 2011069124 A2 | 6/2011 |
| WO | 2017192579 A1 | 11/2017 |

OTHER PUBLICATIONS

Becker-Baldus et al., Angew. Chem. Int. Ed. 2021, 60, 16442-16447 (Year: 2021).*
Jia et al., Circ Arrhythm Electrophysiol. 2011; 4: 753-760 (Year: 2011).*
He et al Journal of Molecular and Cellular Cardiology 51 (2011) 198-206 (Year: 2011).*
Nussinovitch et al., Cardiovascular Research (2014) 102, 176-187 (Year: 2014).*
Merriam-Webster: non-biological, retrieved from the internet Feb. 16, 2023: https://www.merriam-webster.com/dictionary/non-biological (Year: 2023).*
Shah et al., Nanoscale, 2015, 7, 16571-16577 (Year: 2015).*
International Search Report and Written Opinion; PCT Application No. PCT/US2017/030626; dated Sep. 28, 2017.
Abilez O., "Cardiac Optogenetics," 2012 Annual International Conference of the IEEE Engineering in Medicine and Biology Society, 2012, vol. 2012, pp. 1386-1389.
Akemann W., et al., "Effect of Voltage Sensitive Fluorescent Proteins on Neuronal Excitability," Biophysical Journal, May 2009, vol. 96, pp. 3959-3976.
Ambrosi C.M., et al., "Optogenetic Control of Cardiomyocytes via Viral Delivery," Methods in Molecular Biology, 2014, vol. 1181, pp. 215-228.
Ambrosi C.M., et al., "Optogenetics-Enabled Assessment of Viral Gene and Cell Therapy for Restoration of Cardiac Excitability," Scientific Reports, Dec. 1, 2015, vol. 5, No. 17350, 16 pages.
Bamann C., et al., "Spectral Characteristics of the Photocycle of Channelrhodopsin-2 and Its Implication for Channel Function," Journal of Molecular Biology, Jan. 18, 2008, vol. 375, No. 3, pp. 686-694.

(Continued)

*Primary Examiner* — Evelyn Y Pyla
(74) *Attorney, Agent, or Firm* — Kory D. Christensen

(57) ABSTRACT

Bio-photonic devices or target cells and cell cultures including bio-photonic devices and target cells are provided. Methods of preparing cell cultures including bio-photonic devices and target cells are also provided. Methods of analyzing the electrophysiology of target cells using the cell cultures are provided. Systems for analyzing the electrophysiology of target cells are also provided.

19 Claims, 32 Drawing Sheets

(56) References Cited

OTHER PUBLICATIONS

Bellin M., et al., "Induced Pluripotent Stem Cells: The New Patient?," Nature Reviews Molecular Cell Biology, Nov. 2012, vol. 13, No. 11, pp. 713-726.
Bowlby M.R., et al., "hERG (KCNH2 or Kv11.1) K+ Channels: Screening for Cardiac Arrhythmia Risk," Current Drug Metabolism, Nov. 2008, vol. 9, No. 9, pp. 965-970.
Brandenburger M., et al., "Organotypic Slice Culture from Human Adult Ventricular Myocardium," Cardiovascular Research, 2012, vol. 93, pp. 50-59.
Burton R.A.B., et al., "Optical Control of Excitation Waves in Cardiac Tissue," Nature Photonics, Dec. 2015, vol. 9, No. 12, pp. 813-816.
Chang T.C., et al., "Parallel Microfluidic Chemosensitivity Testing on Individual Slice Cultures," Lab on a Chip, Dec. 7, 2014, vol. 14, No. 23, pp. 4540-4551.
Chung C.Y., et al., "Hypertrophic Phenotype in Cardiac Cell Assemblies Solely by Structural Cues and Ensuing Self-Organization," The FASEB Journal, Mar. 2011, vol. 25, No. 3, pp. 851-862.
Chung C.Y., et al., "The Role of Cardiac Tissue Alignment in Modulating Electrical Function," Journal of Cardiovascular Electrophysiology, Dec. 2007, vol. 18, No. 12, pp. 1323-1329.
Clements I.P., et al., "Optogenetic Stimulation of Multiwell MEA Plates for Neural and Cardiac Applications," Proceedings of SPIE, Mar. 10, 2016, vol. 9690, 10 pages.
Dugue G.P., et al., "A Comprehensive Concept of Optogenetics," Progress in Brain Research, 2012, vol. 196, pp. 1-28.
Dunlop J., et al., "High-Throughput Electrophysiology: An Emerging Paradigm for Ion-Channel Screening and Physiology," Nature Reviews Drug Discovery, Apr. 2008, vol. 7, No. 4, pp. 358-368.
Efimov I.R., et al., "Optical Imaging of the Heart," Circulation Research, Jul. 9, 2004, vol. 95, No. 1, pp. 21-33.
Entcheva E., "Cardiac Optogenetics," The American Journal of Physiology-Heart and Circulatory Physiology, 2013, vol. 304, pp. H1179-H1191.
Entcheva E., et al., "Acoustic Micromachining of Three-Dimensional Surfaces for Biological Applications," Lab on a Chip, 2005, vol. 5, pp. 179-183.
Entcheva E., et al., "All-Optical Control of Cardiac Excitation: Combined High-Resolution Optogenetic Actuation and Optical Mapping," The Journal of Physiology, 2016, vol. 594, No. 9, pp. 1-8.
Entcheva E., et al., "Macroscopic Optical Mapping of Excitation in Cardiac Cell Networks With Ultra-High Spatiotemporal Resolution," Progress in Biophysics and Molecular Biology, 2006, vol. 92, pp. 232-257.
FDA., "Challenge and Opportunity on the Critical Path to New Medical Products," 2004, 3 pages.
Fermini B., et al., "A New Perspective in the Field of Cardiac Safety Testing through the Comprehensive in Vitro Proarrhythmia Assay Paradigm," Journal of Biomolecular Screening, 2016, vol. 21, No. 1, pp. 1-11.
Fertig N., et al., "Renaissance of Ion Channel Research and Drug Discovery by Patch Clamp Automation," Future Medicinal Chemistry, 2010, vol. 2, No. 5, pp. 691-695.
Herron T.J., et a., "Optical Imaging of Voltage and Calcium in Cardiac Cells & Tissues," Circulation Research, Feb. 17, 2012, vol. 110, No. 4, pp. 609-623.
Hochbaum D.R., et al., "All-Optical Electrophysiology in Mammalian Neurons Using Engineered Microbial Rhodopsins," Nature Methods, Aug. 2014, vol. 11, No. 8, pp. 825-833.
Hortigon-Vinagre M.P., et al., "The Use of Ratiometric Fluorescence Measurements of the Voltage Sensitive Dye Di-4-ANEPPS to Examine Action Potential Characteristics and Drug Effects on Human Induced Pluripotent Stem Cell-Derived Cardiomyocytes," Toxicological Sciences, 2016, vol. 154, No. 2, pp. 320-331.
Johnson D.M., et al., "Diastolic Spontaneous Calcium Release from the Sarcoplasmic Reticulum Increases Beat-to-Beat Variability of Repolarization in Canine Ventricular Myocytes after Beta-Adrenergic Stimulation," Circulation Research, Jan. 18, 2013, vol. 112, No. 2, pp. 246-256.
Khan J.M., et al., "The Case for Induced Pluripotent Stem Cell-Derived Cardiomyocytes in Pharmacological Screening," British Journal of Pharmacology, 2013, vol. 169, pp. 304-317.
Knollmann B.C., "Induced Pluripotent Stem Cell-Derived Cardiomyocytes: Boutique Science or Valuable Arrhythmia Model?," Circulation Research, Mar. 15, 2013, vol. 112, No. 6, pp. 969-976.
Leyton-Mange J.S., et al., "Rapid Cellular Phenotyping of Human Pluripotent Stem Cell-Derived Cardiomyocytes using a Genetically Encoded Fluorescent Voltage Sensor," Stem Cell Reports, Feb. 11, 2014, vol. 2, pp. 163-170.
Lu Z., et al., "Suppression of Phosphoinositide 3-Kinase Signaling and Alteration of Multiple Ion Currents in Drug-Induced Long QT Syndrome," Science Translational Medicine, Apr. 25, 2012, vol. 4, No. 131, 20 pages.
MacCannell K.A., et al., "A Mathematical Model of Electrotonic Interactions between Ventricular Myocytes and Fibroblasts," Biophysical Journal, Jun. 2007, vol. 92, pp. 1421-1432.
McPheeters M.T., et al., "An Infrared Optical Pacing System for High-Throughput Screening of Cardiac Electrophysiology in Human Cardiomyocytes (Conference Presentation)," Proceeding SPIE 10042, Diagnostic and Therapeutic Applications of Light in Cardiology, Apr. 19, 2017, DOI: https://doi.org/10.1117/12.2253110, 3 pages.
Mirams G.R., et al., "Simulation of Multiple Ion Channel Block Provides Improved Early Prediction of Compounds' Clinical Torsadogenic Risk," Cardiovascular Research, 2017, vol. 91, pp. 53-61.
Moreno J.D., et al., "A Computational Model to Predict the Effects of Class I Anti-Arrhythmic Drugs on Ventricular Rhythms," Science Translational Medicine, Aug. 31, 2011, vol. 3, No. 98, 20 pages.
Nagel G., et al., "Channelrhodopsin-2, a Directly Light-Gated Cation-Selective Membrane Channel," PNAS, Nov. 25, 2003, vol. 100, No. 24, pp. 13940-13945.
Nagel G., et al., "Channelrhodopsins: Directly Light-Gated Cation Channels," Biochemical Society Transactions, 2005, vol. 33, No. 4, 5 pages.
Packer A.M., et al., "Targeting Neurons and Photons for Optogenetics," Nature Neuroscience, Jul. 2013, vol. 16, No. 7, pp. 805-815.
Piccini J.P., et al., "Current Challenges in the Evaluation of Cardiac Safety during Drug Development: Translational Medicine Meets the Critical Path Initiative," American Heart Journal, Sep. 2009, vol. 158, No. 3, pp. 317-326.
Preziosi P., "Science, Pharmacoeconomics and Ethics in Drug R&D: A Sustainable Future Scenario?," Nature Review Drug Discovery, 2004, vol. 3, pp. 521-526.
Redfern W.S., et al., "Relationships between Preclinical Cardiac Electrophysiology, Clinical QT Interval Prolongation and Torsade De Pointes for a Broad Range of Drugs: Evidence for a Provisional Safety Margin in Drug Development," Cardiovascular Research, 2003, vol. 58, pp. 32-45.
Rodriguez B., et al., "The System Biology Approach to Drug Development: Application to Toxicity Assessment of Cardiac Drugs," Clinical Pharmacology & Therapeutics, Jun. 2, 2010, vol. 88, No. 1, pp. 130-134.
Smedemark-Margulies N., et al., "Tools, Methods, and Applications for Optophysiology in Neuroscience," Frontiers in Molecular Neuroscience, Jul. 17, 2013, vol. 6, No. 18, pp. 13 pages.
Tusscher K.H.W.J.T., et al., "Alternans and Spiral Breakup in a Human Ventricular Tissue Model," American Journal of Physiology, Sep. 1, 2006, 59 pages.
Williams J.C., et al., "Computational Optogenetics: Empirically-Derived Voltage- and Light-Sensitive Channelrhodopsin-2 Model," PLOS Computational Biology, Sep. 2013, vol. 9, No. 9, 19 pages.
Williams J.C., et al., "Optogenetic versus Electrical Stimulation of Human Cardiomyocytes: Modeling Insights," Biophysical Journal, Apr. 2015, vol. 108, pp. 1934-1945.
Yang T., et al., "Screening for Acute Ikr Block is Insufficient to Detect Torsades de Pointes Liability Role of Late Sodium Current," Circulation, Jan. 15, 2014, vol. 130, No. 3, pp. 224-234.

(56) References Cited

OTHER PUBLICATIONS

Yu J., et al., "Cardiac Optogenetics: Enhancement by All-Trans-Retinal," Scientific Reports, Nov. 16, 2015, vol. 5, No. 16542, 12 pages.
Zhang F., et al., "Multimodal Fast Optical Interrogation of Neural Circuitry," Nature, Apr. 5, 2007, vol. 446, pp. 633-639.

* cited by examiner

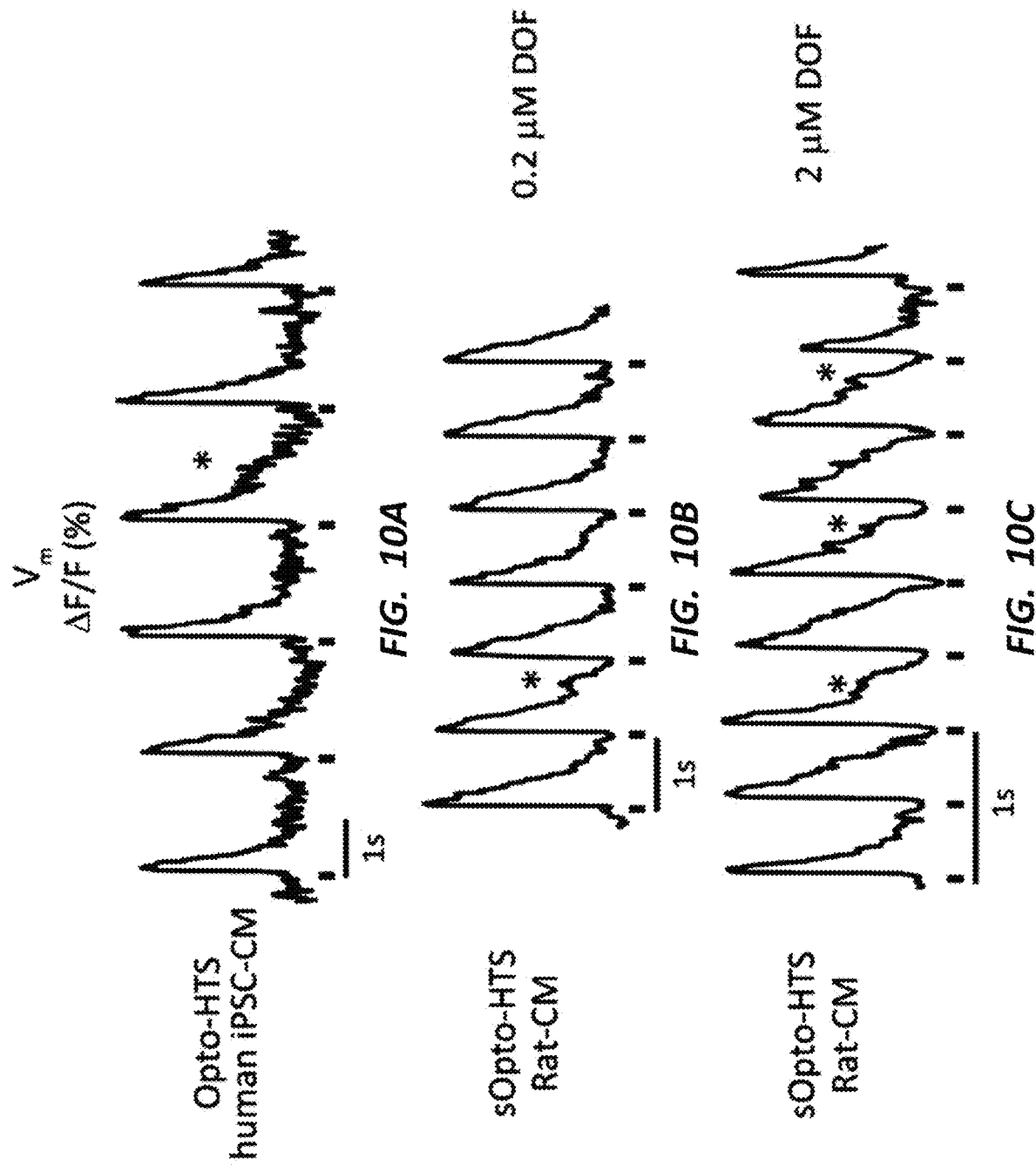

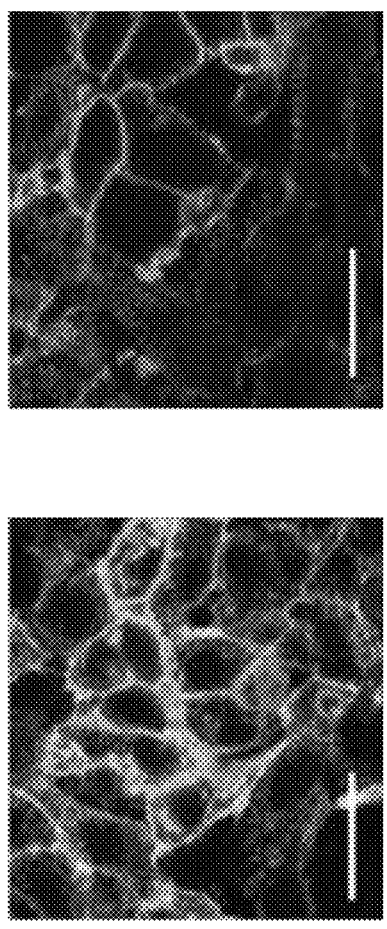
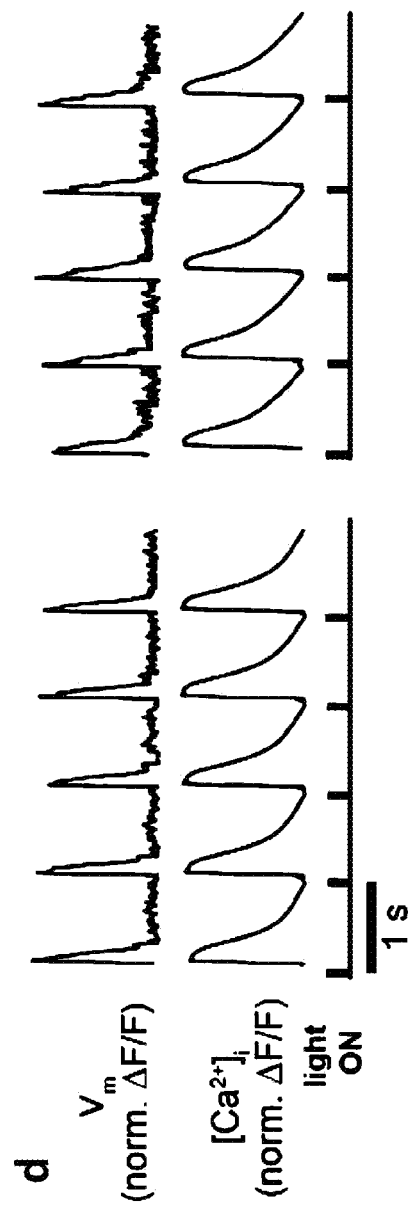
FIG. 16 (Cont'd)

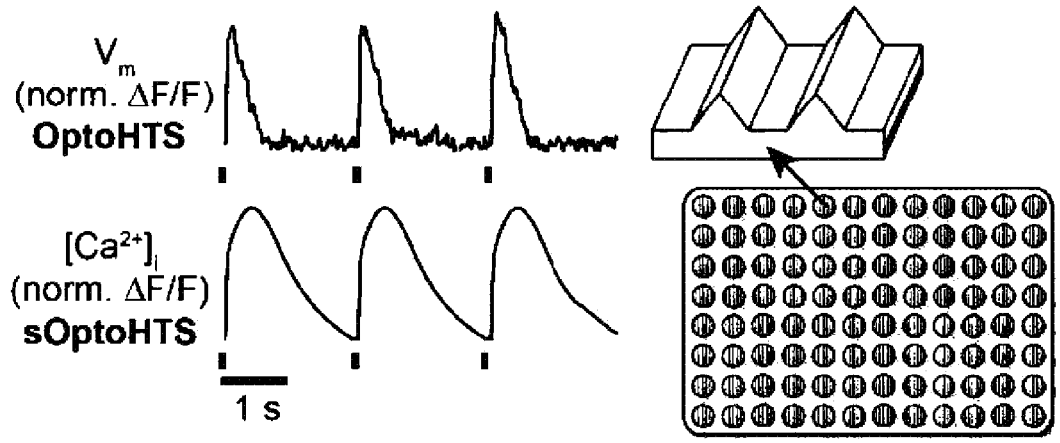
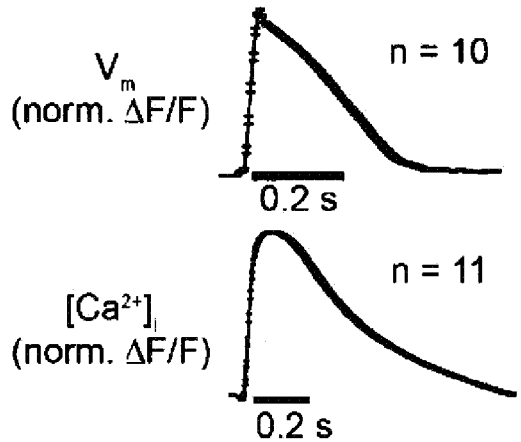 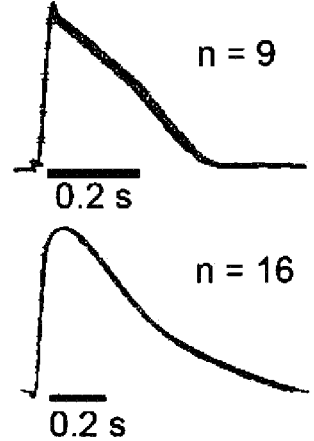
FIG. 16 (Cont'd)

h
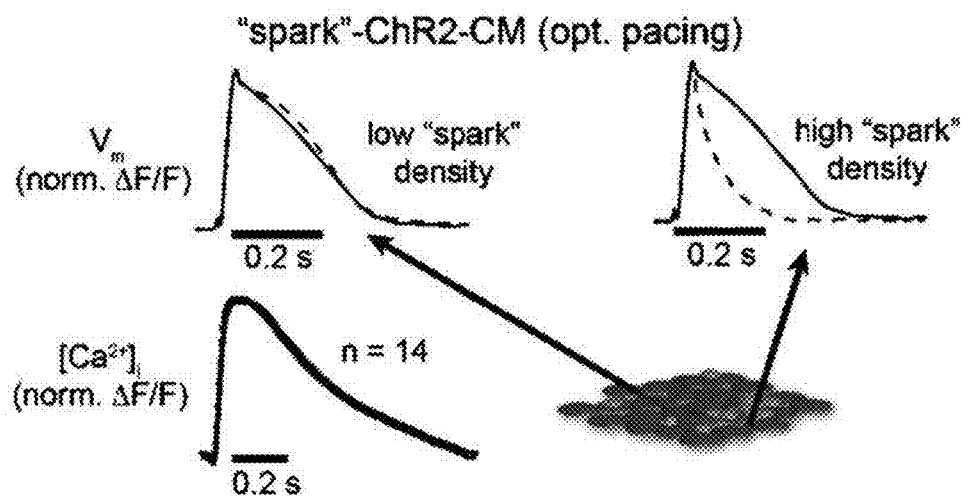
i
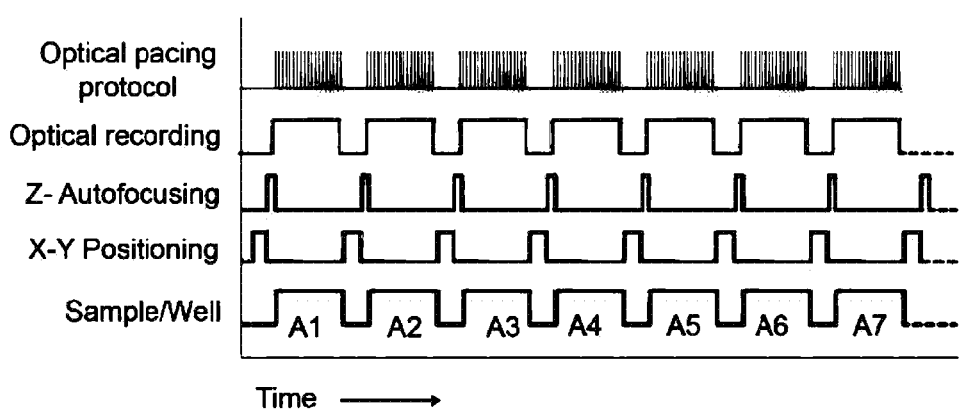
FIG. 16 (Cont'd)

a
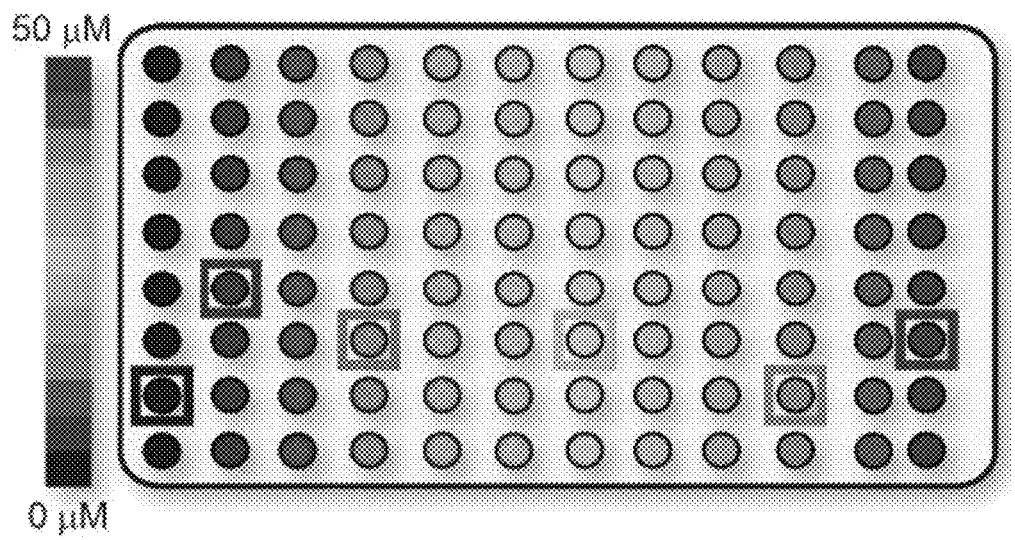
b
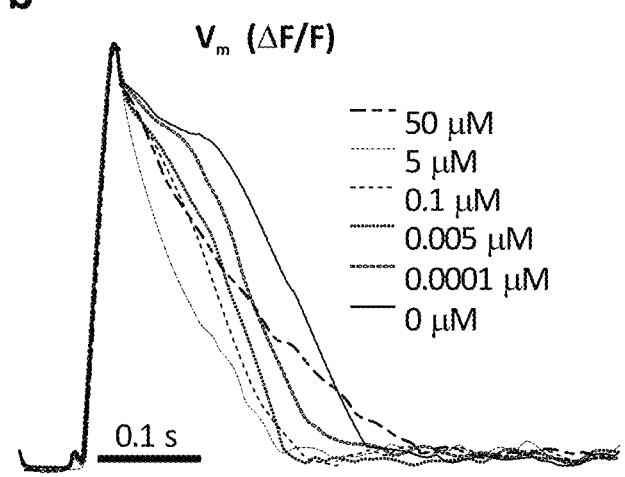
FIG. 17

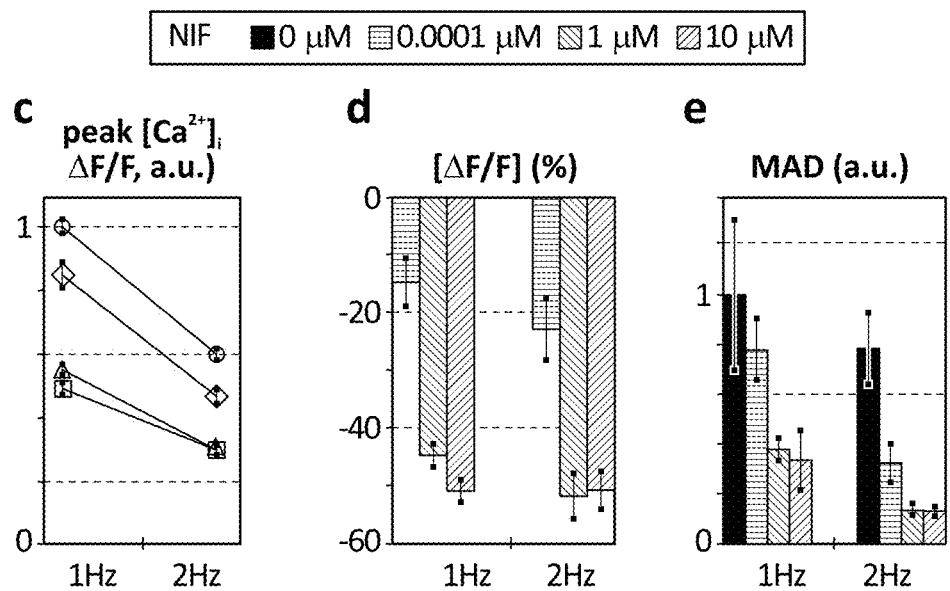
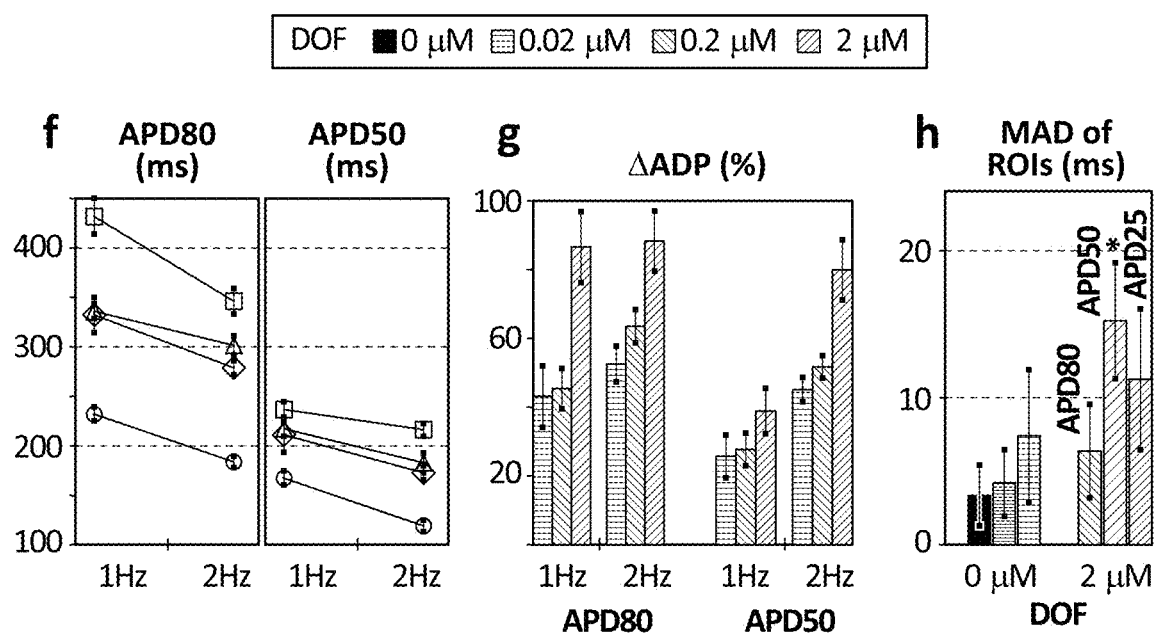
FIG. 19 (Con'd)

AUTOMATED SYSTEM FOR HIGH-THROUGHPUT ALL-OPTICAL DYNAMIC ELECTROPHYSIOLOGY

CROSS-REFERENCE TO RELATED APPLICATIONS

This application is a national stage entry of PCT/US2017/030626 filed May 2, 2017, which claims the benefit of U.S. Provisional Application No. 62/330,741, filed on May 2, 2016, each of which is hereby incorporated by reference in their entirety.

STATEMENT REGARDING FEDERALLY SPONSORED RESEARCH

This invention was made with government support under Grant No. 1511353 awarded by the National Science Foundation and Grant No. R01 HL111649 awarded by the National Institutes of Health. The government has certain rights in the invention.

TECHNICAL FIELD

The present disclosure relates generally to bio-photonic devices. The present disclosure also relates to cell cultures including bio-photonic devices and target cells. Systems for using the cell cultures to analyze the electrophysiology of the target cells and related methods are also provided.

BACKGROUND

Current preclinical testing for cardiac toxicity generally relies on assessing QT prolongation and HERG block, which is not a complete predictor of cardiotoxicity. This often results in drugs being thrown out prior to preclinical testing that may not end up causing arrhythmias. Although the Comprehensive in vitro Proarrhythmia Assay (CiPA) initiative is attempting to alleviate this by studying drug effects on multiple human cardiac currents using more traditional methods or other high-throughput (HT) methods, it relies on computer simulations to integrate multiple patch-clamp obtained data (in non-myocytes) to predict drug effects.

Current HT screening systems used by the main drug testing companies, such as ASTRAZENECA™ and GLAXOSMITHKLINE™, are: 1) MOLECULAR DEVICES™ IONWORKS®, and 2) MOLECULAR DEVICES™ FLIPR® (Fluorometric Imaging Plate Reader). IONWORKS®, featuring an automated planar patch platform, relies on contact perforation on the bottom of each well, through which suction is applied to create a "seal"; electrodes (up to 48) are lowered in the solution to electrically stimulate; readouts are electrical. The need for contact (high seal) limits this assay to certain cell lines and prevents further scalability. FLIPR® shows promise as an optical readout system but only slow voltage changes can be tracked (about 1 Hz readout) and stimulation is done by adding depolarizing (KCl) solution to each well, i.e., no dynamic testing is possible.

Also, none of these systems are able to provide spatio-temporally dynamic stimulation and also look at the spatial dispersion of activation. This may be important because there are drugs that are known to cause long QT but do not induce TdP because they do not induce EADs and reduce dispersion. Additionally, there are limited means of testing cardiotoxicity of certain types of drugs (e.g., cancer drugs) that cannot be tested in healthy patients in preclinical trials.

Generally, none of these systems provide a means of high-resolution simultaneous recording of both voltage and calcium relationships. This can be important when dealing with drugs that are made to affect calcium handling (e.g., the immunosuppressant tacrolimus) thus disrupting electromechanical coupling.

BRIEF DESCRIPTION OF THE DRAWINGS

The embodiments disclosed herein will become more fully apparent from the following description and appended claims, taken in conjunction with the accompanying drawings.

provide more relevant, and even patient-specific predictions, compared to the main testing route on the left (a comprehensive characterization of all ion channels, signaling and other intracellular processes is impossible, and hence the complex computational models operate in a high level of uncertainty, thus providing only probabilistic predictions). Furthermore, OptoDyCE can provide additional simultaneous cellular and multicellular readouts, e.g., intracellular calcium, contractility, and cell coupling, which are relevant to arrhythmia testing but cannot be derived by the approach on the left. Therefore, OptoDyCE can help further constrain/improve computational modeling as well.

Figure 5A:
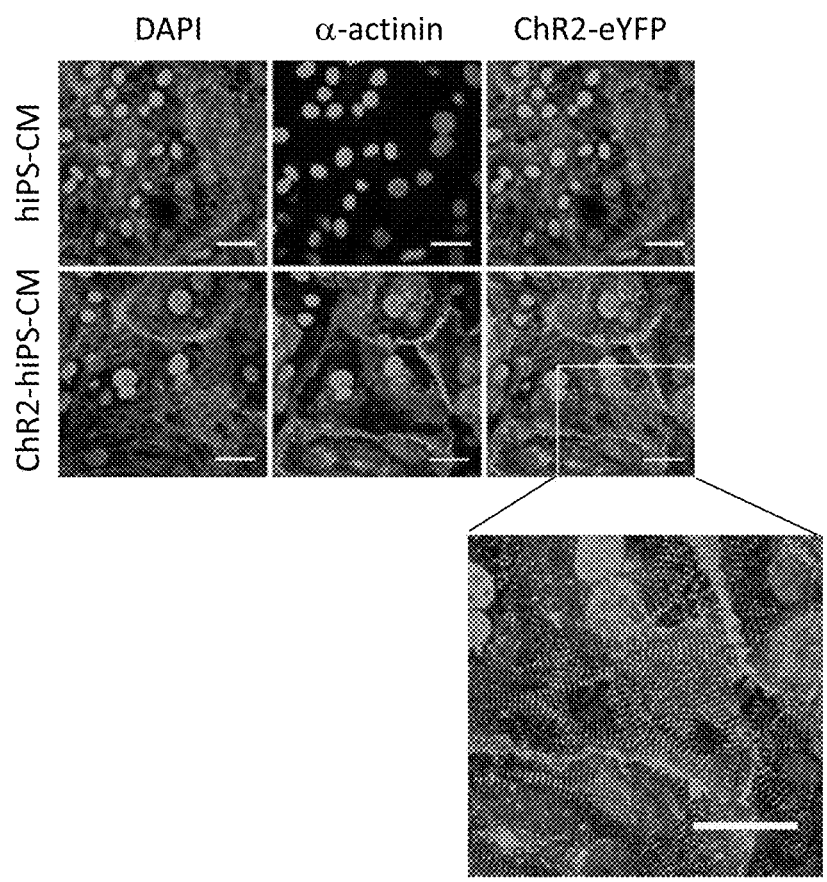

FIG. 5A shows all-optical electrophysiology in human iPS-CMs. hiPS-CMs without (top) and with Ad-ChR2 (H134R)-eYFP delivery at MOI 250 (bottom). Red fluorescence indicates α-actinin staining illustrating the CM-like properties of hiPS-CMs, blue indicates DAPI nuclear staining, and green fluorescence indicates the eYFP reporter of Channelrhodopsin-2 (ChR2). Combination (left) of the α-actinin (right) and eYFP (center) channels indicate expression of ChR2 in the ChR2-hiPS-CMs. Scale bar is 30 μm.

Figure 5B:
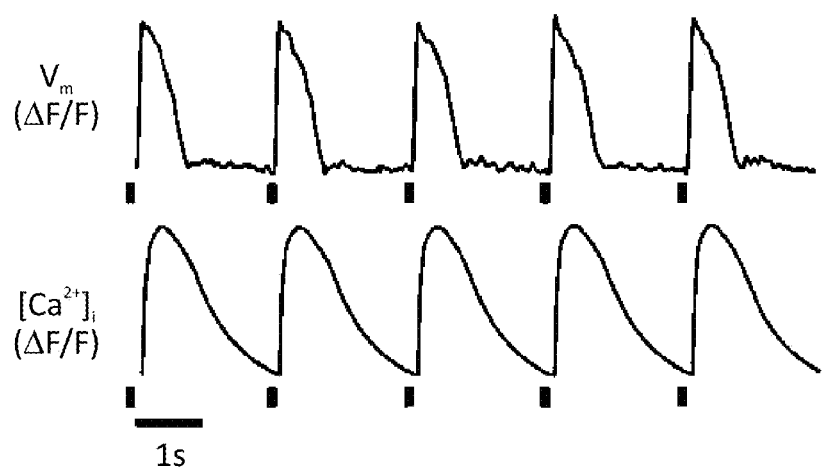

FIG. 5B shows an optical recording of $V_m$ and $[Ca^{2+}]_i$ in optically paced ChR2-hiPS-CMs used in an automated readout (96-well plate format).

Figure 6A:
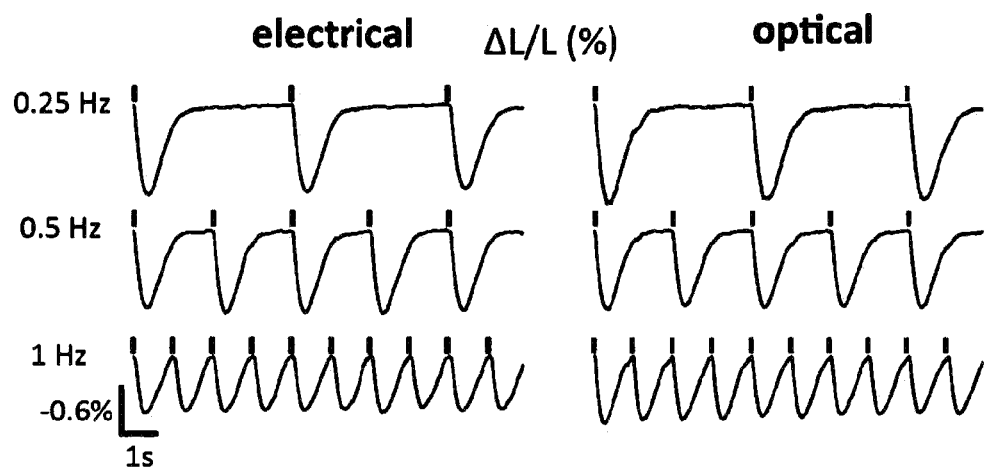

FIG. 6A illustrates validation of comparable contractility in response to optical (90 ms, 0.015 mW/mm$^2$) vs. electrical (5 ms, 10 V bipolar) stimulation under different pacing frequencies. Tick marks indicate stimulation pulses. Shown are measurements in neonatal rat ventricular ChR2-CMs.

Figure 6B:
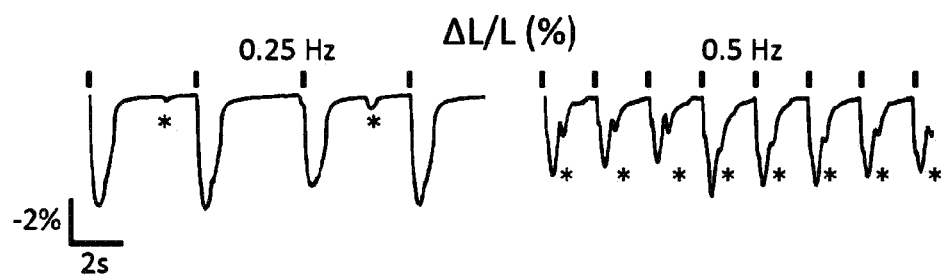

FIG. 6B illustrates that the OptoDyCE system is capable of resolving abnormal contractile responses, e.g., aftercontractions (asterisks) that can be used as arrhythmogenic markers.

Figures 7A, 7B:
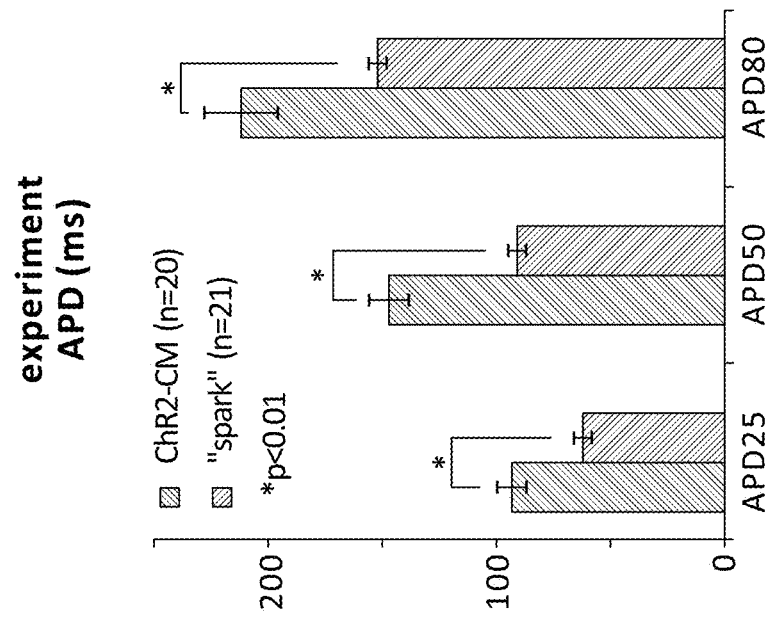

FIG. 7A shows a computational example of human ventricular APs, scaled and normalized in amplitude (as would be measured by an optical method) for two cases of "spark"-driven excitation of CMs: when 2 "spark" cells were connected to a CM or when 5 "spark" cells were connected to a CM. The loading effect in the latter case resulted in action potential duration (APD) shortening in the CM (see FIG. 16, panel "h"). The computer model employed ChR2-expressing cardiac fibroblasts (not HEK cells) as "spark" cells (see also Example 10 below), but the effect is applicable to both cell types.

Figure 16:
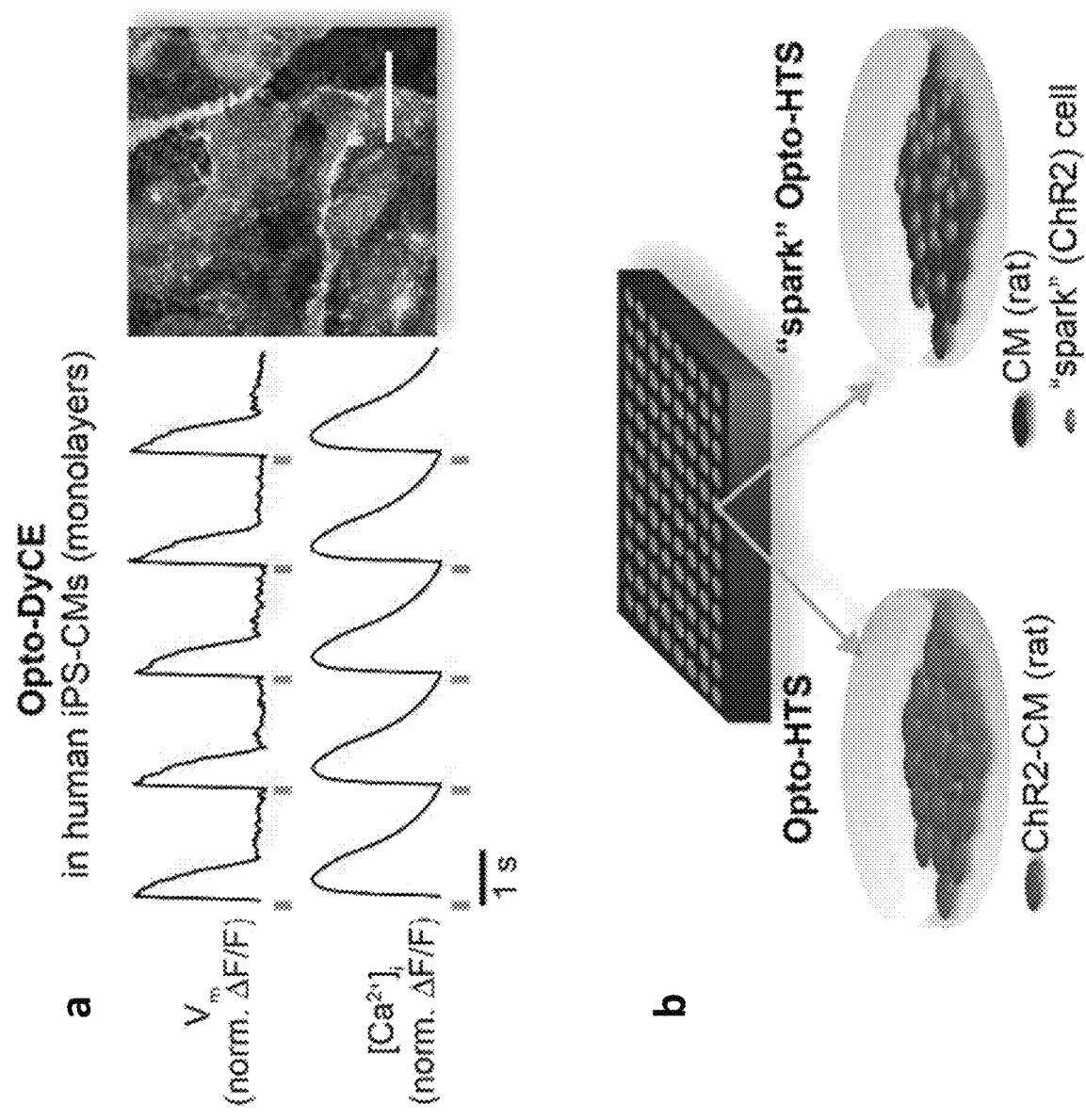
Figure 16:
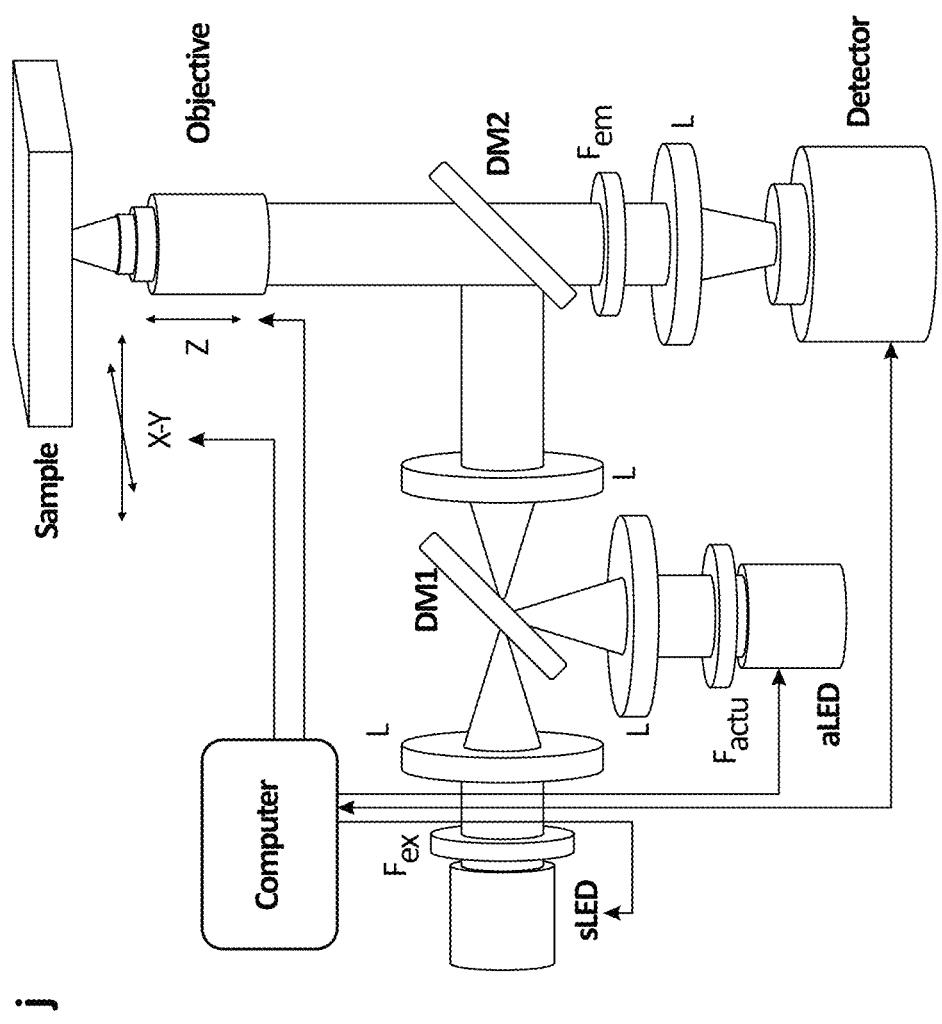

FIG. 7B depicts a comparison of the experimentally measured APD for optically paced ChR2-CMs and HEK-ChR2-CMs for the samples shown in FIG. 16, panels "g" and "h." For the cell density and the implementation here, with random sprinkling, there was overall APD shortening in the "spark"-driven HEK-ChR2-CMs compared to the ChR2-CMs (p<0.01 using ANOVA test followed by a Tukey-Kramer post hoc correction for multiple comparisons). To avoid APD shortening, the "spark" cells can easily be localized and can serve as optical pacemaking conduits without affecting the APD of the CMs. FIGS. 7A and 7B show the effect of "spark" cell density on measured APD in CMs.

Figure 8:
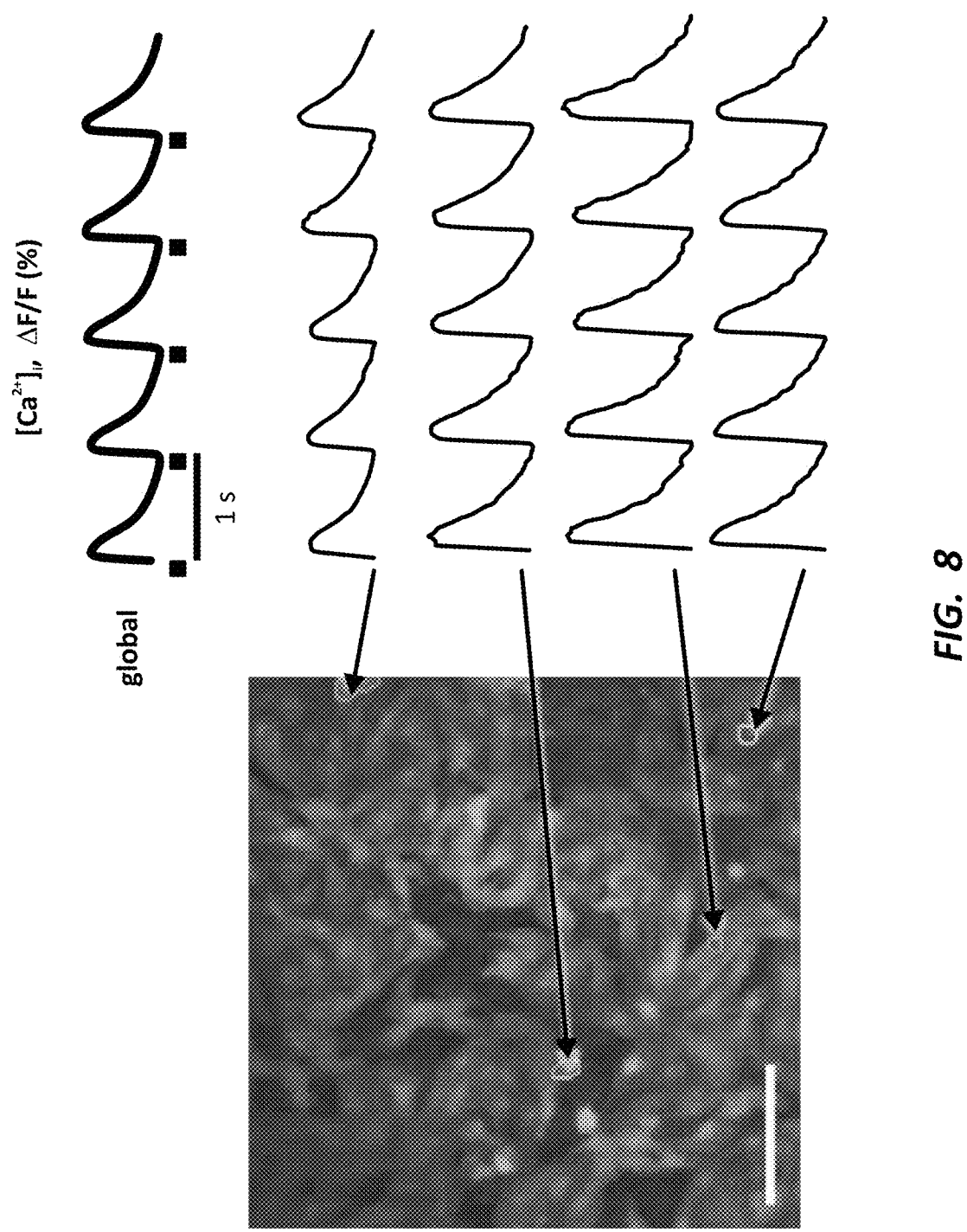

FIG. 8 illustrates the parallelism of the OptoHTS system. In each well, optical recording was performed over multiple cells in parallel. Typical field of view (FOV) was 400 μm×400 μm, resulting in about 200-400 parallel cell measurements per FOV (well), i.e., about 30,000 cell-level measurements per 96-well plate at 20× magnification. For a dynamic pacing protocol, using multi-beat pacing (6 second dwell time per well), this resulted in about 10 min/plate, i.e., about 600 independent multi-cellular (>200 cells) samples (or compounds) per hour (with the possibility to reach >10,000 compounds per day, which qualifies for high-throughput screening (HTS)). Shown here are the global (space-integrated) calcium measurement for a well (scale bar 100 μm) and traces from individual cell-level regions, as outlined. While most of the analysis presented here dealt with the global responses, the parallelism is built-in into the disclosed approach and can easily be utilized further.

Figure 9A:
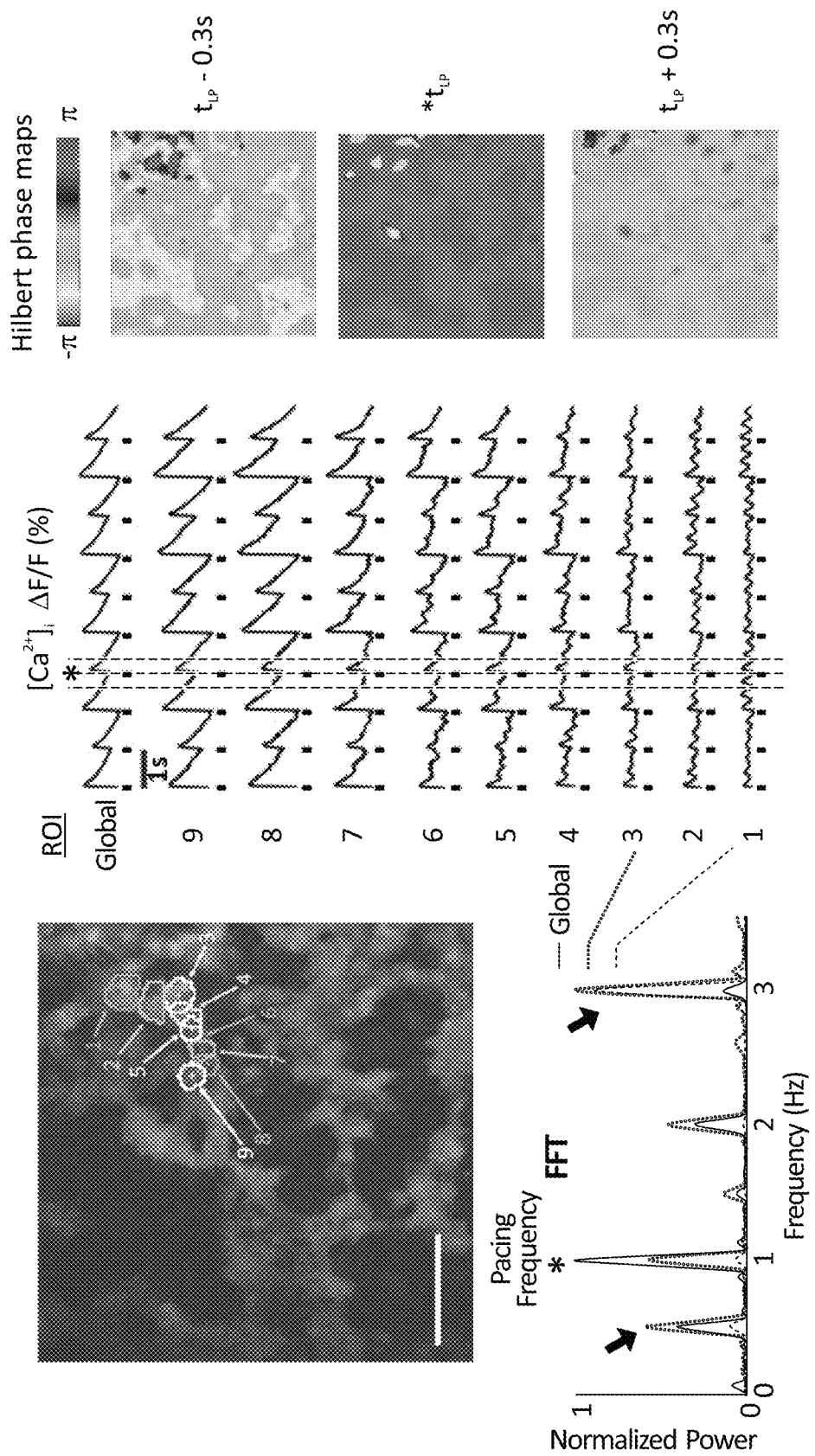

FIG. 9A depicts an example of spatial heterogeneity with localized spontaneous calcium release (SCR) in a ChR2-CM sample treated with 0.02 μM dofetilide, when paced at 1 Hz using 0.539 mW/mm$^2$ 10 ms light pulses. Traces from 9 outlined ROIs (top left; scale bar 100 μm), along with the global trace, exhibit abnormal pacing behavior (center). Deviation from the global signal, progressing from ROI 9 to ROI 1, can be seen in both trace morphology and in the frequency domain (FFT plot left), where the 1 Hz pacing frequency is indicated by an asterisk; a strong low frequency component at 0.5 Hz is due to alternans (arrow), while the observed sub-cellular SCR results in a higher frequency component (arrow) at 3 Hz. Phase maps (Hilbert transform, right) were used to identify localized intracellular $Ca^{2+}$ waves due to SCR; the three panels, corresponding to the grey dashed lines in the recorded traces, show the instantaneous phase 300 ms prior to the optical stimulus ($t_{LP}$–0.3 s), during the optical stimulus ($t_{LP}$), and 300 ms after the optical stimulus ($t_{LP}$+0.3 s).

Figures 9B, 9C:
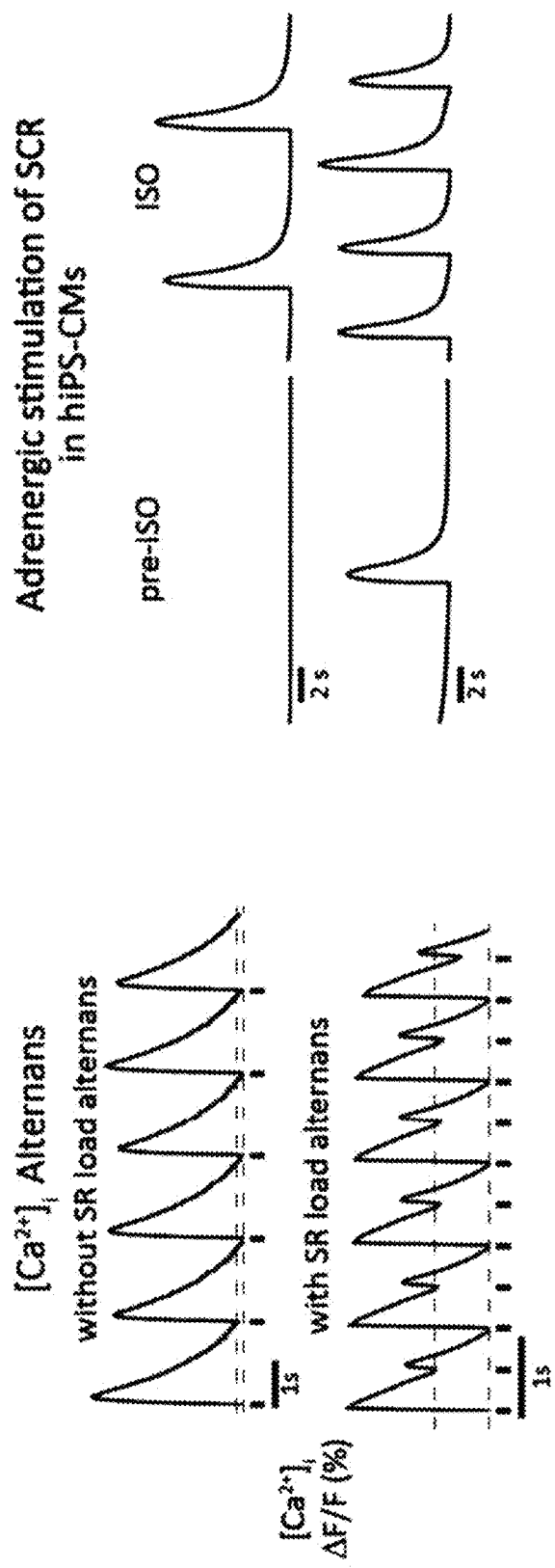

FIG. 9B illustrates that OptoDyCE can identify $[Ca^{2+}]_i$ alternans with and without SR load alternation. An example trace from "spark"-hiPSC-CMs (top) shows subtle alternans without SR load alternation when paced at 0.5 Hz with 1.51 mW/mm$^2$ 5 ms pulses, while an example trace from a ChR2-CMs sample paced at 2 Hz with a 0.455 mW/mm$^2$ 10 ms pulse shows prominent SR load alternation (dashed lines).

FIG. 9C illustrates that calcium-mediated pacing activity was induced by 1 μM isoproterenol (10 min) in quiescent hiPS-CMs (top) and rate of pacing was accelerated in spontaneously beating hiPS-CMs (bottom). FIGS. 9A-9C illustrate capturing sub-cellular spontaneous $Ca^{2+}$ release (SCR) events. The recording of SCR events and other calcium instabilities within multicellular samples can be easily performed using OptoDyCE.

FIG. 10A shows intrinsic variability, including EADs (asterisks), observed in this ChR2-hiPSC-CM sample, paced at 0.5 Hz pacing.

FIG. 10B shows drug-induced AP variation in sOptoHTS samples treated with 0.2 μM dofetilide paced at 1 Hz. FIGS. 10A and 10B show abnormalities in AP morphology captured by OptoDyCE.

FIG. 10C shows drug-induced AP variation in sOptoHTS samples treated with 2 μM dofetilide paced 2 Hz. Lower doses of dofetilide create sporadic EADs (asterisks), while higher doses yield large temporal variability in AP morphology (in addition to spatial variability quantified in FIG. 19), with increased instances of EADs.

Figure 11:
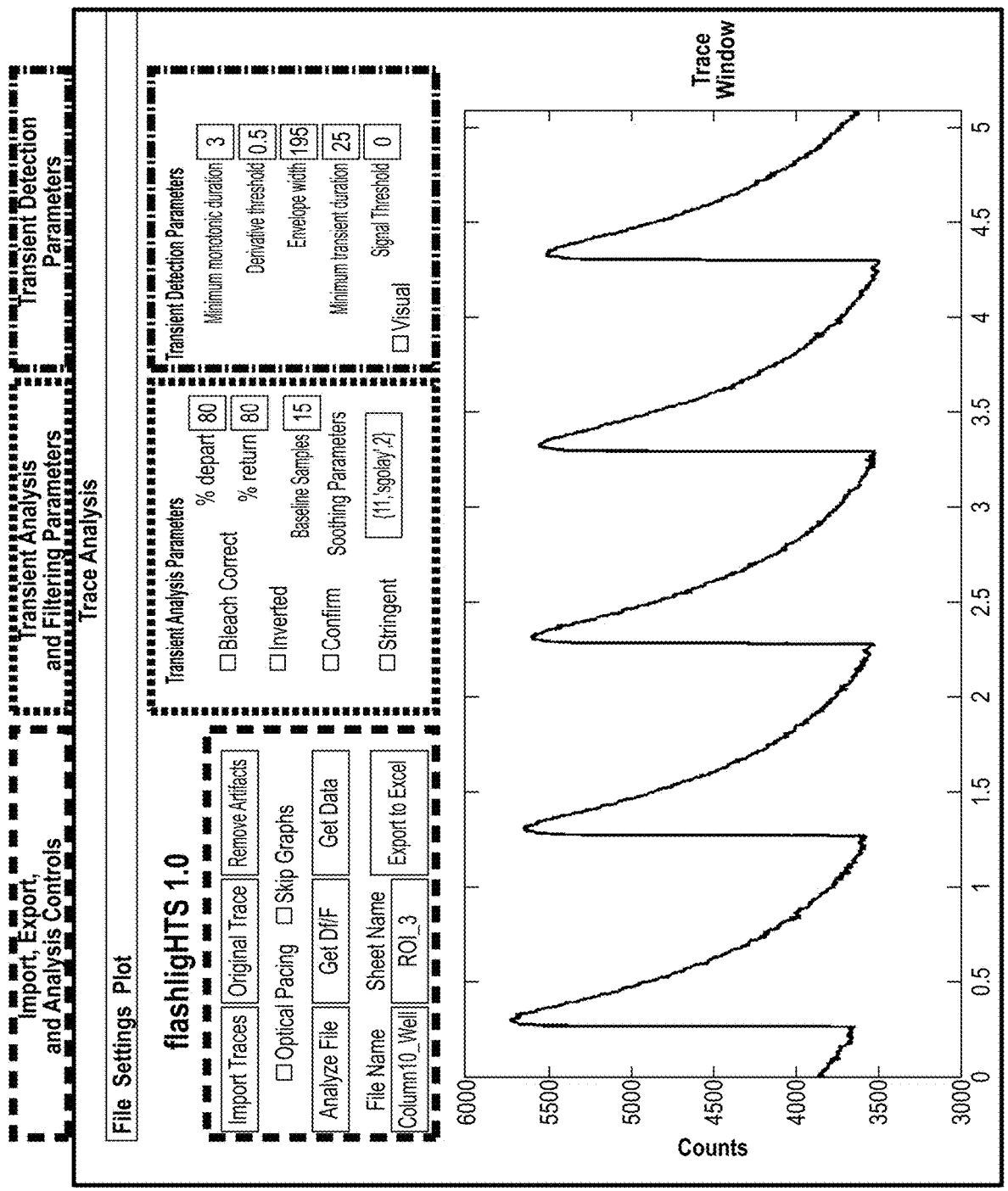

FIG. 11 is a snapshot of the custom-developed automated analysis software, flashligHTS.

Figure 12:
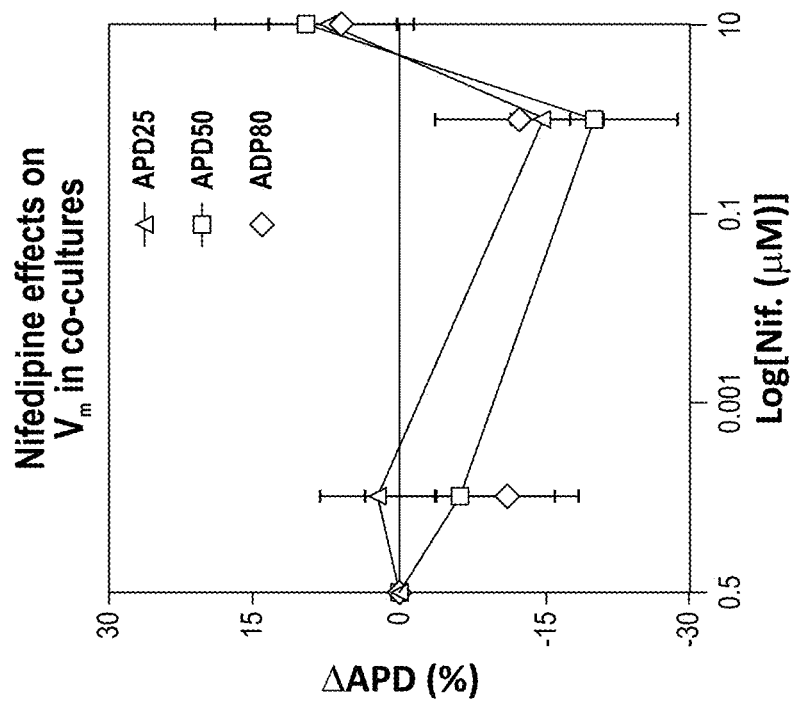

FIG. 12 depicts drug action in standard TCU co-cultures. Shown is the effect of nifedipine on APD in standard co-cultures based on the TCU concept, when the "spark" cells are not "sprinkled" at a later point but rather mixed uniformly at the time of plating of the CMs. Comparing with FIG. 18, panel "a," all three cases qualitatively capture the action of nifedipine on APD, but the sOptoHTS with "sprinkling" is generally simple, modular, and industrially applicable.

Figure 13:
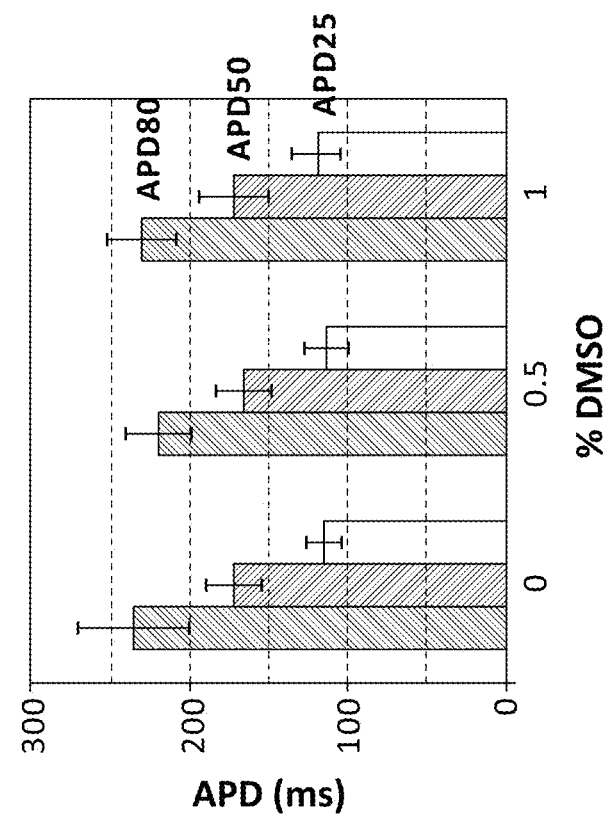

FIG. 13 shows the effect of DMSO on APD. CM-ChR2 cells were dosed with 0, 0.5, and 1% DMSO in Tyrode's solution to assess the effect of DMSO on APD. Within the used concentrations to administer drugs and/or dyes (in all cases <1%), DMSO was not seen to affect the electrophysiological (EP) measurements.

Figure 14:
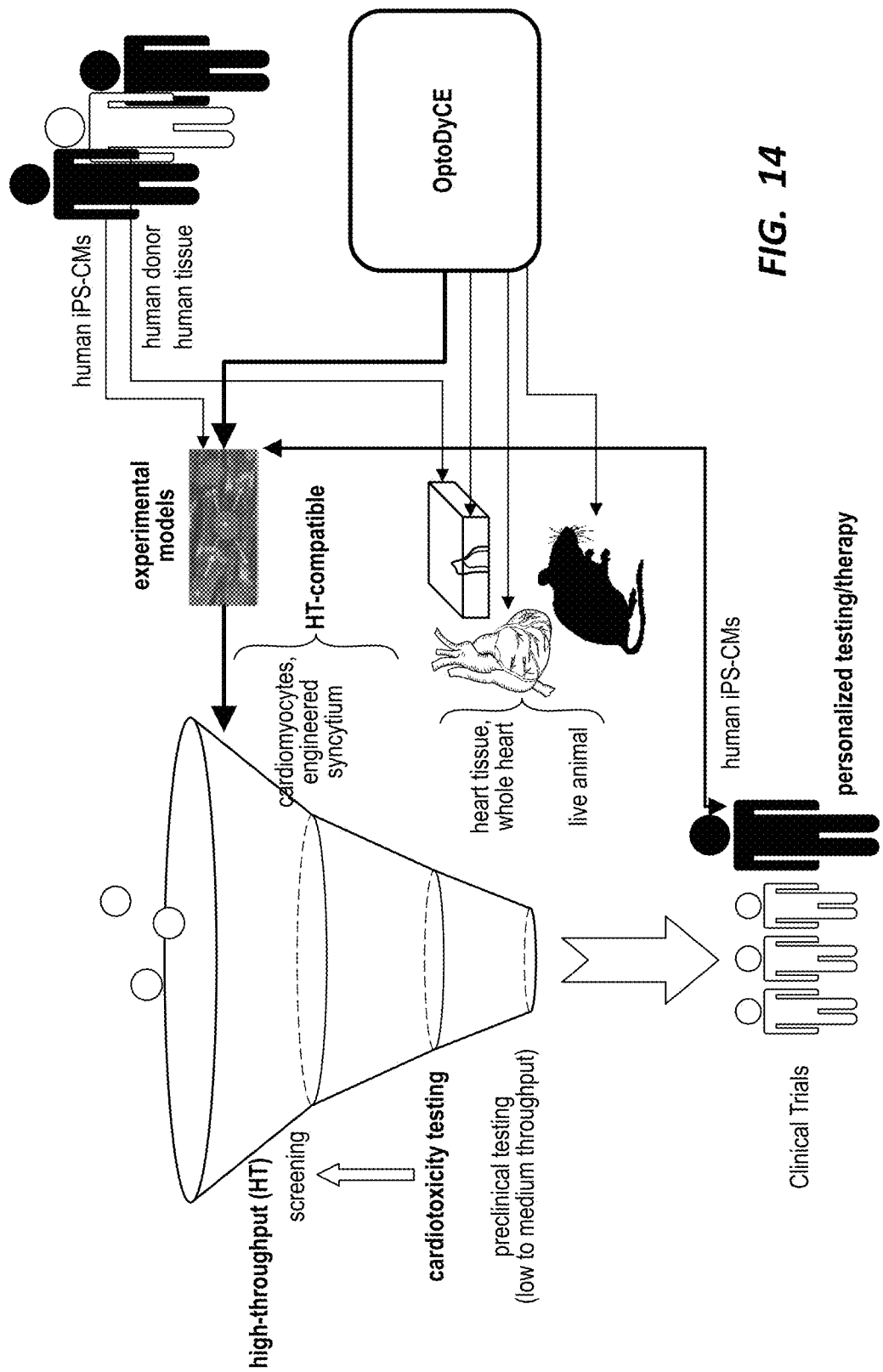

FIG. 14 is a schematic of HT in drug discovery and cardiotoxicity testing. In the "funnel" workflow of drug development/drug testing, only some assays are HT-compatible. The all-optical dynamic cardiac electrophysiology framework (OptoDyCE) provided herein is applicable to various experimental models (cells, tissue, whole heart, and live animal testing) but generally only some of these (CMs and some engineered syncytia, e.g., human iPS-CMs) are scalable and HT-compatible. Furthermore, they are generally the only ones that can be used directly for personalized testing/therapy on the same patient. OptoDyCE technology can elevate such functional cellular/multicellular CM assays for drug discovery or cardiotoxicity testing to HT-status.

Figure 15:
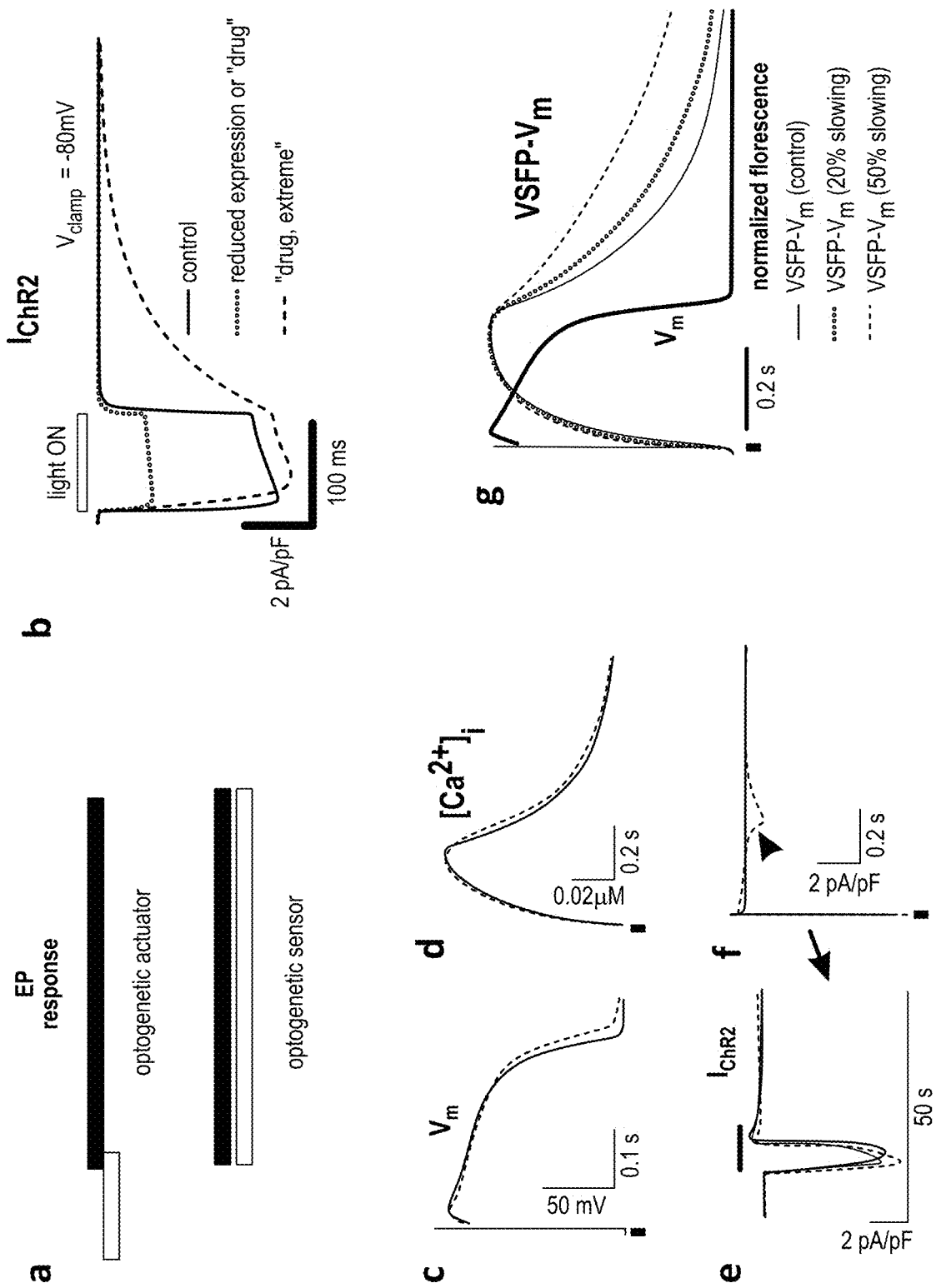

FIG. 15 depicts drug testing considerations and computational analysis of the use of optogenetic tools. A comparison of actuators (e.g., ChR2) versus optogenetic sensors (e.g., VSFP2.3) in human ventricular myocytes is depicted. A fast optogenetic actuator acts as a stimulation impulse and is "time-detached" from the EP response (see panel "a"), and therefore a hypothetical drug action that affects ChR2 current amplitude and/or kinetics (see panel "b") has minimal effect on the optically-triggered APs (APs) (see panel "c") and calcium transients (CTs) (see panel "d"), if light irradiances are adjusted to provide supra-threshold currents (see panel "e"). Even extreme drug interference with ChR2 off-kinetics results in minor (5%) APD prolongation (see panel "c") due to re-activation of inward ChR2 current during repolarization (see panel "f"). In contrast, an optogenetic sensor, e.g., VSFP2.3, is fully "temporally-convolved" with the EP response (see panel "a"), and even a mild drug action on the sensor can profoundly influence the EP readout (see panel "g").

FIG. 16 depicts experimental HT implementation and validation of automated OptoDyCE. Human ChR2-iPSC-CMs in a monolayer (see panel "a") or in 3D structures (see panel "e"), and rat ChR2-CMs (OptoHTS) and "spark"-ChR2-CMs (sOptoHTS) (see panels "b," "c," "d," "g," and "h") are optogenetically transformed to respond to optical stimulation. ChR2 expression cg by eYFP reporter (green), α-actinin staining (red), and DAPI nuclear stain (blue) are shown (see panels "a" and "c"). Scale bars are 30 µm (see panel "a") and 25 µm (see panel "c"). Optical pacing reliably triggers Vm and [Ca2+]i signals, measured optically (see panels "a," "d," and "e"). Validation of OptoHTS comes from identical AP and CT morphology for electrically-paced CM-controls (non-transduced) and optically-paced ChR2-CMs (see panels "f" and "g"); in sOptoHTS, high "spark" cell density can lead to APD shortening compared to control CM (see panel "h"; see also FIGS. 7A and 7B) without much effect on CT morphology (see panel "h"). A fully automated HT version of OptoDyCE in 96-well format using a custom-built optical setup and an automation protocol is demonstrated (see panels "i" and "j").

Figure 17:
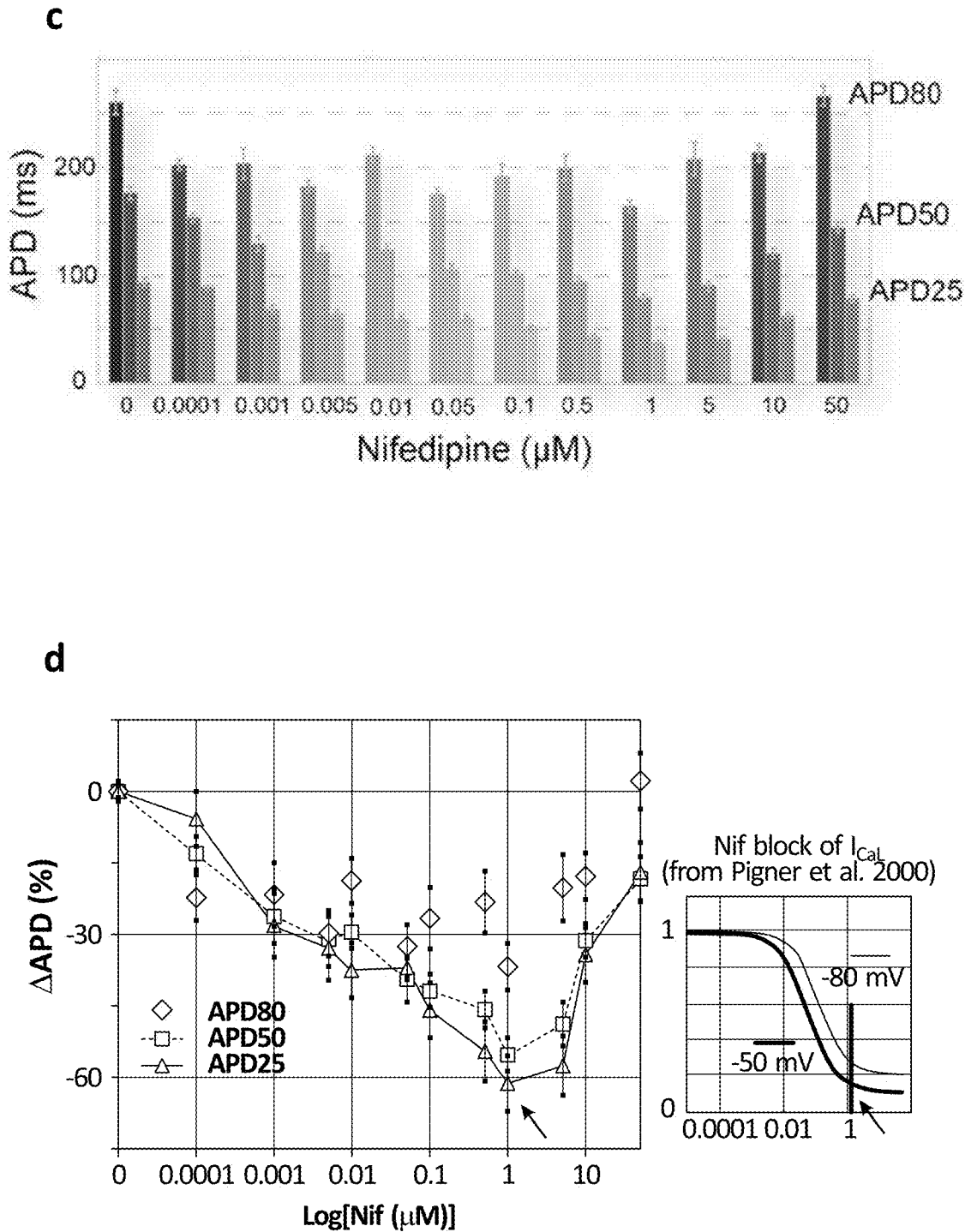
Figure 17:
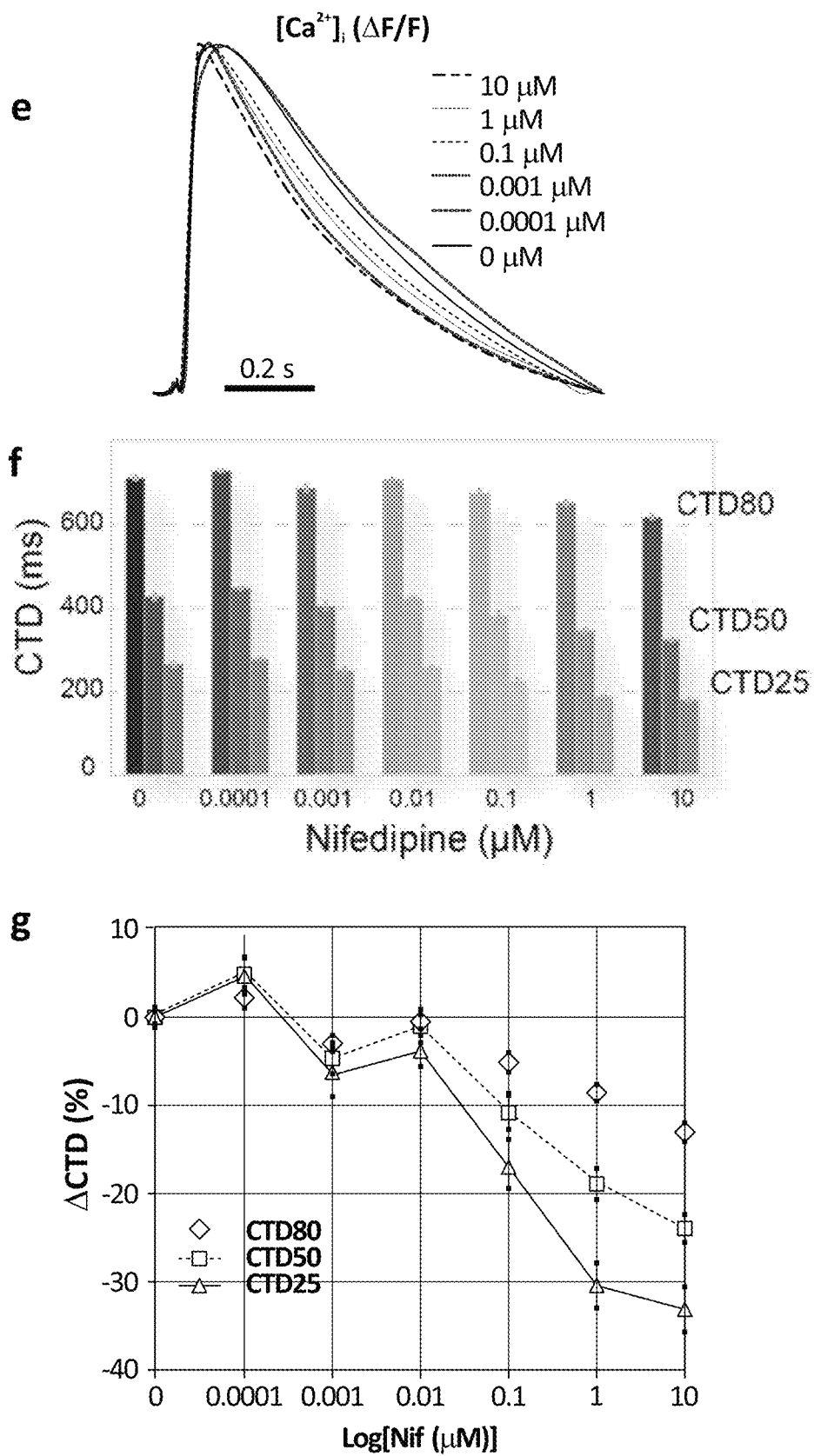

FIG. 17 is a demonstration of OptoHTS for HT dose-response drug testing. Nifedipine, an L-type $[Ca^{2+}]_i$ channel ($I_{CaL}$) blocker, is applied at 12-concentration graded dosing (0-50 µM) to ChR2-CMs in 96-well plates (see panel "a"). Optical recordings of multiple voltage (see panels "b"-"d") or calcium events (see panels "e"-"g") are obtained during optical pacing at 1 Hz, screening the full plate in under 10 minutes (see also FIG. 8). Example averaged over 10 seconds (see panels "b" and "e") and quantitative results for APD and CTD (see panels "c," "d," "f," and "g") are shown. Expected APD (N=4 to 7 samples, at least 800 single-cell records per concentration) (see panels "b"-"d") and CTD (N=4 to 6 samples, at least 800 single-cell records per concentration) (see panels "e"-"g") shortening, especially at the APD25/CTD25 and APD50/CTD50 levels, occurred due to nifedipine blocking the inward L-type calcium current. Maximum APD shortening is observed at around 1 µM, consistent with maximum block of $I_{CaL}$ reached at that concentration (see panel "d" inset). Beyond 1 µM, indirect (voltage-mediated) or non-specific action on other ion channels partially counters the block of inward $Ca^{2+}$ current and can reduce or eliminate the APD shortening (see panel "d"). Nifedipine appears to monotonically shorten CTD up to 10 µM (see panels "f" and "g"). Data are presented as mean±standard error of the mean (SEM), and each well is considered an independent sample, represented by a spatially-averaged trace.

Figure 18:
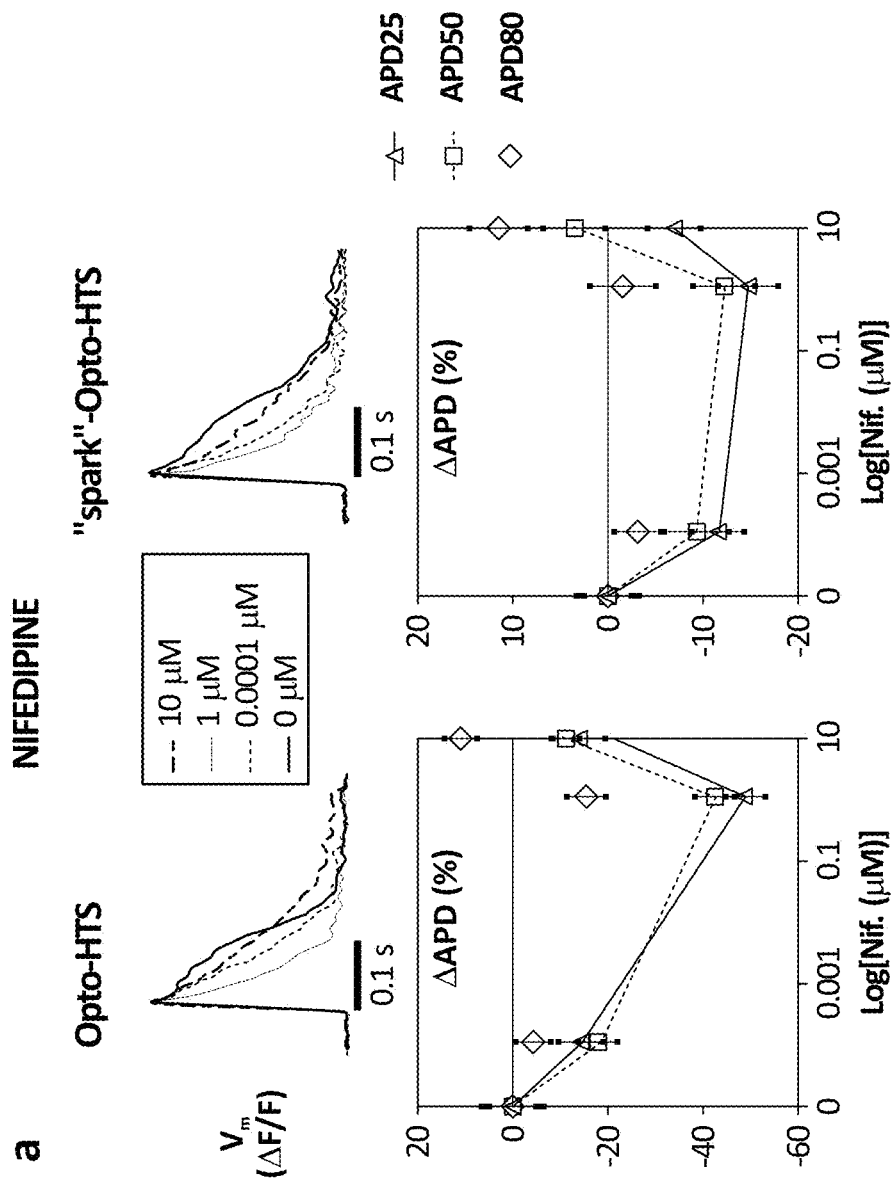
Figure 18:
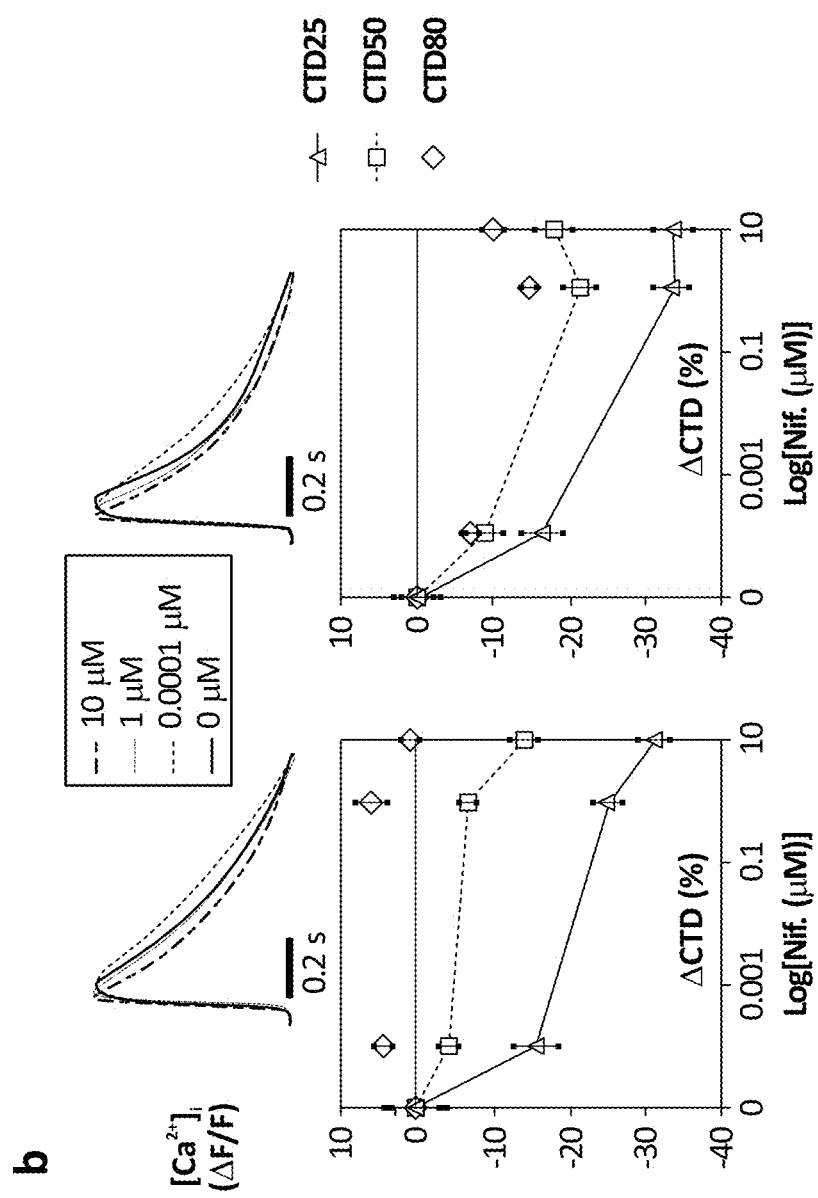
Figure 18:
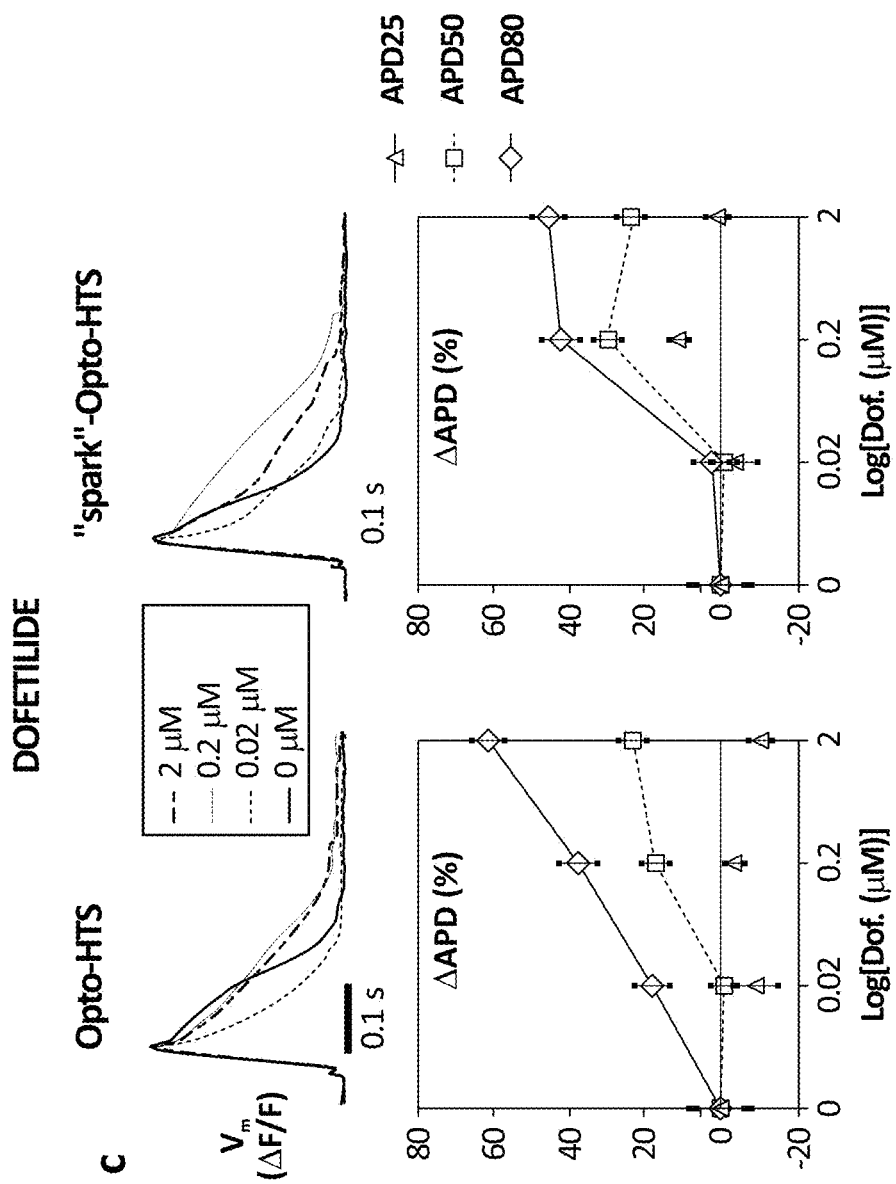
Figure 18:
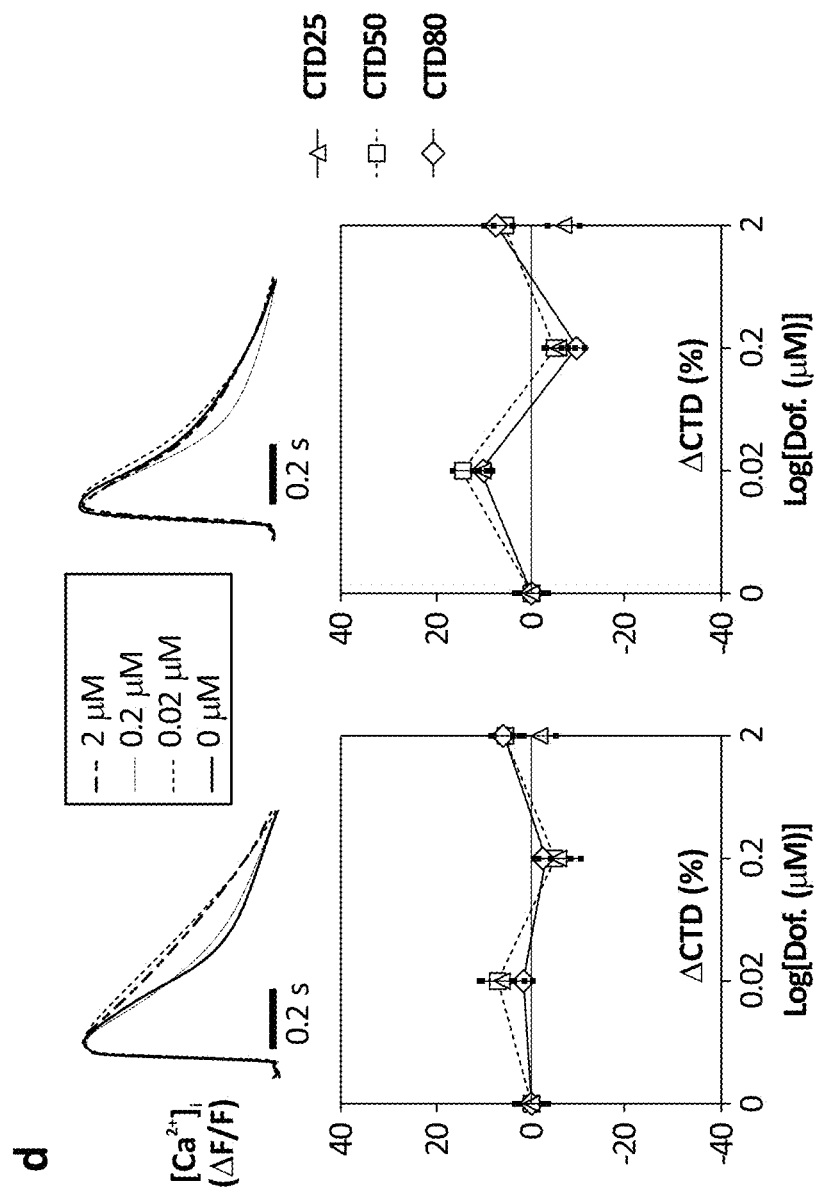

FIG. 18 depicts experimental comparison of OptoHTS versus "spark"-OptoHTS for functional drug testing. With reference to panels "a"-"d," OptoHTS (left) and sOptoHTS (right) provide qualitatively and quantitatively similar results for measured effects on APD (see panels "a" and "c") and CTD (see panels "b" and "d") for both nifedipine (see panels "a" and "b") and dofetilide, a blocker of the rapid delayed rectifier, $I_{Kr}$ (see panels "c" and "d"). N=3 to 16 samples (at least 600 single-cell records or more) for each condition and each data point in the panels above. Data are presented as mean±SEM, and each well is considered an independent sample.

Figure 19:
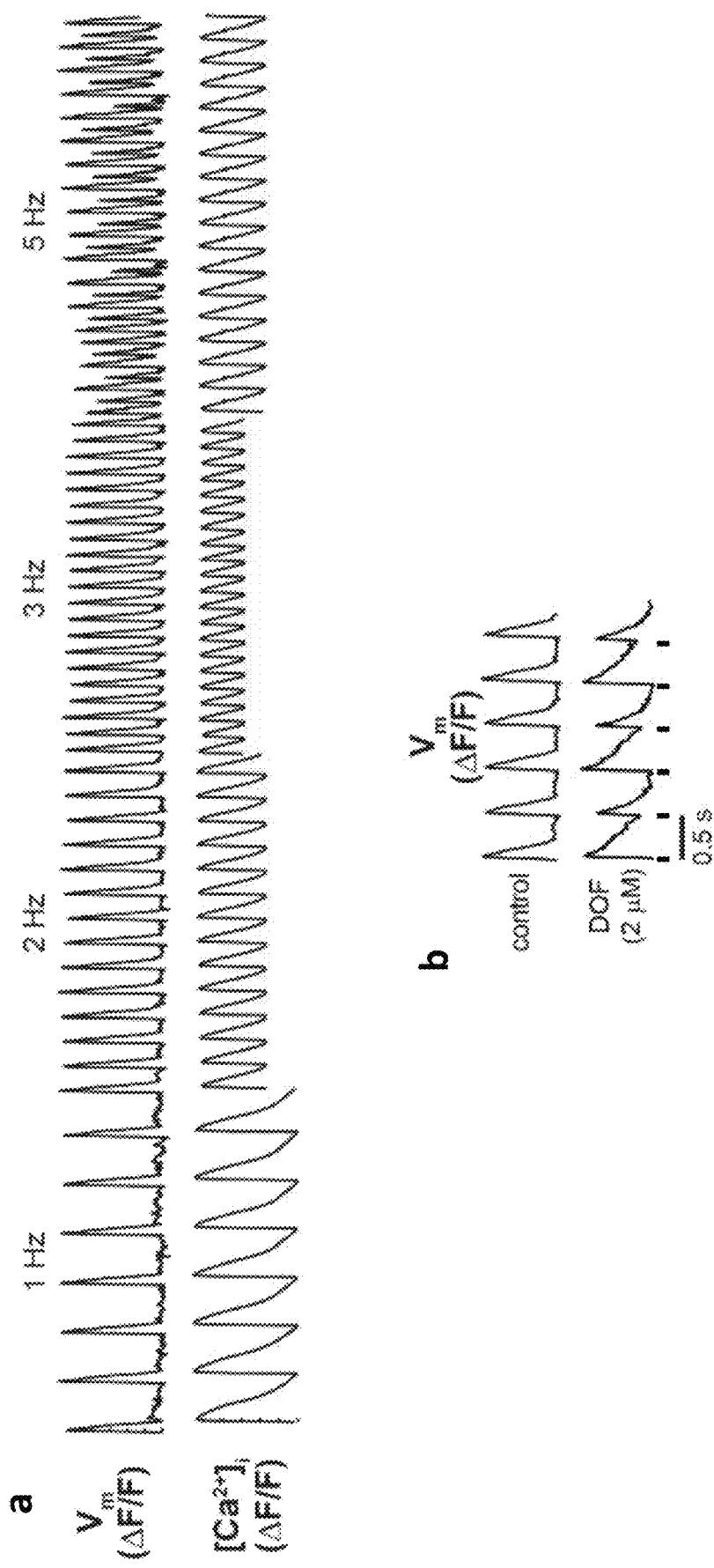

FIG. 19 depicts the utility of OptoDyCE for spatio-temporal characterization. Dynamic pacing provides a means of studying pacing-induced $V_m$ and $Ca^{2+}$ restitution and instabilities (see panel "a") or drug-induced instabilities, i.e., 2 µM dofetilide leading to voltage alternans at relatively low pacing frequency (2 Hz) (see panel "b"). High-content dynamic information is obtained from a single data run (see panels "c"-"h"). For example, restitution and temporal or spatial variability (quantified by median absolute deviation (MAD)) are shown as functions of both drug dose and pacing frequency for peak calcium in the presence of nifedipine (see panels "c"-"e") and for APD in the presence of dofetilide (see panels "f" and "g"). Nifedipine action on peak calcium (% change) is dose-dependent but frequency-independent (see panels "c" and "d"). Nifedipine appears to reduce temporal variability of peak calcium (assessed by MAD), and this reduction is augmented by higher-frequency pacing (see panel "e"). Dofetilide shows enhanced action on APD50 at higher frequency (opposite to reverse-use dependence) (see panels "f" and "g"). Spatial variation as a function of drug dose can also be assessed by analyzing multiple regions of interest (ROIs) within the same well (see panel "h"; see also FIGS. 8-9C). Dofetilide at 2 µM seems to increase spatial variability in APD, i.e., increase dispersion of repolarization, compared to control during 1 Hz pacing (p<0.05 for APD50 obtained using ANOVA test followed by a Tukey-Kramer post hoc correction for multiple comparisons). N=5 to 16 samples (at least 1000 single-cell records or more) for each condition and each data point in the panels above. Data are presented as mean±SEM, and each well is considered an independent sample.

Figure 20B:
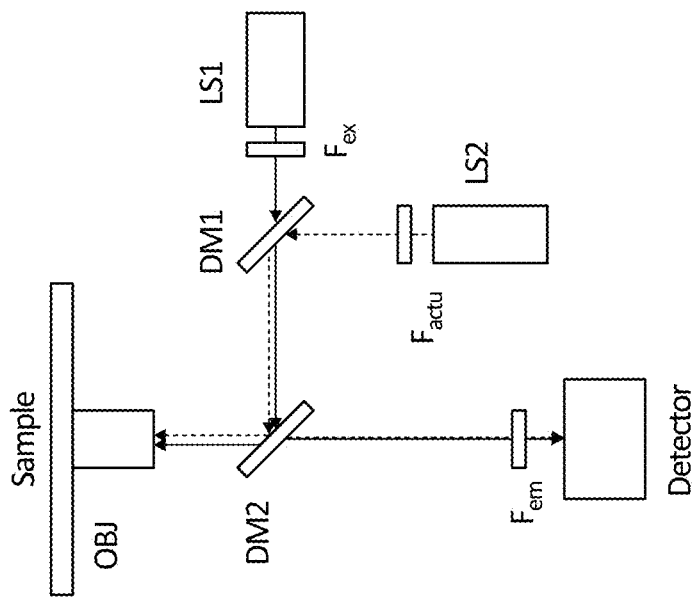
Figure 20A:
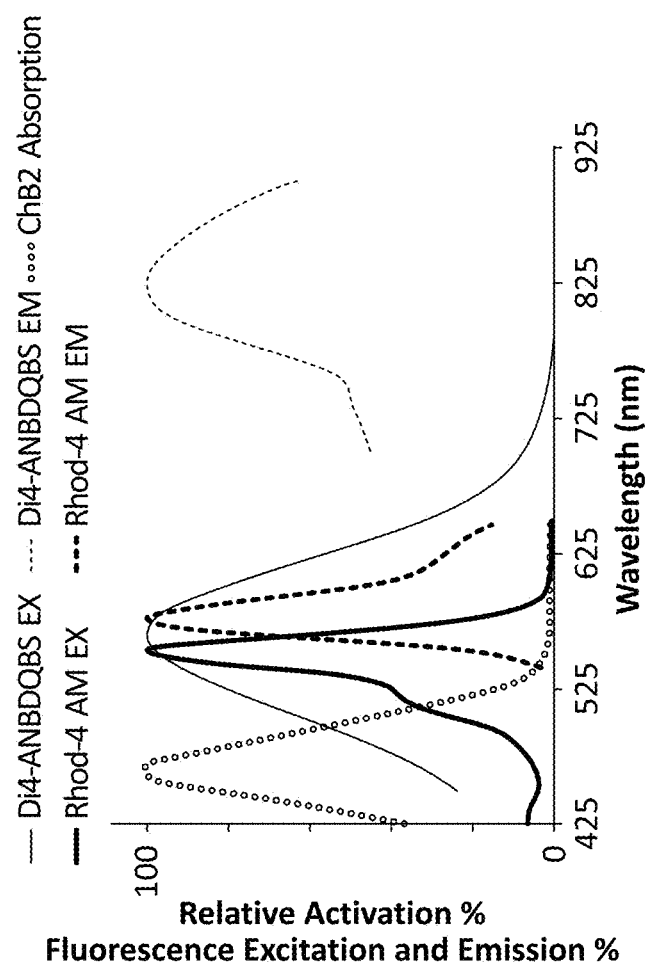

FIG. 20A depicts activation spectra for ChR2 and excitation (EX) and emission (EM) spectra for the voltage sensitive dye Di-4-ANBDQBS and the calcium sensitive dye Rhod-4™, AM.

FIG. 20B illustrates a generalized optical path of the OptoDyCE system.

Figure 21:
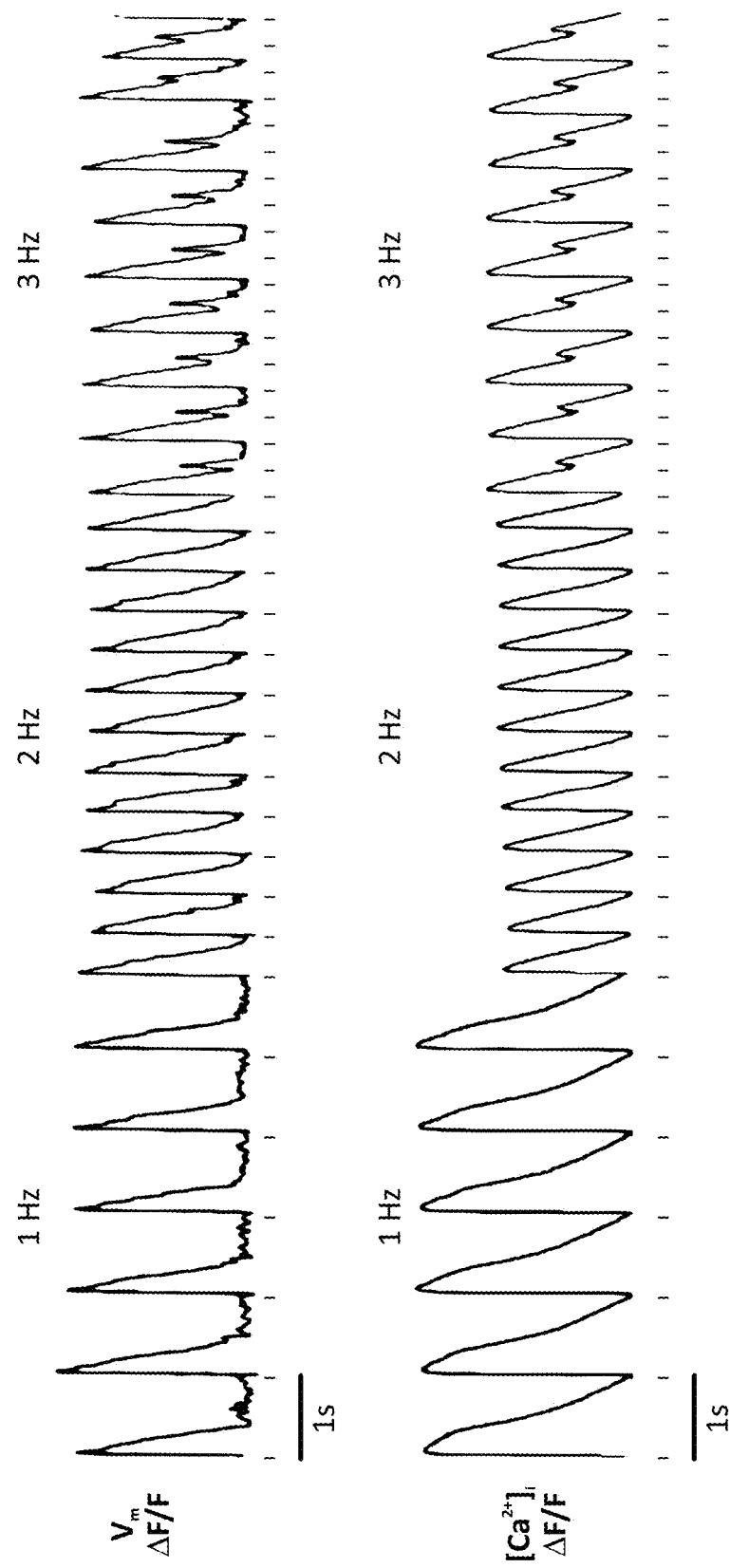

FIG. 21 depicts example optical recordings in ChR2-expressing neonatal rat ventricular myocytes. Membrane potential ($V_m$; top) and intracellular calcium ($[Ca^{2+}]_i$; bottom) recordings were obtained using Di-4-ANBDQBS (excitation: 650 nm; emission: >700 nm) and Rhod-4™, AM (excitation 530 nm; emission: 605 nm), respectively. Cells were optically paced using 5 ms pulses at 1 Hz, 2 Hz, and 3 Hz.

Figure 22:
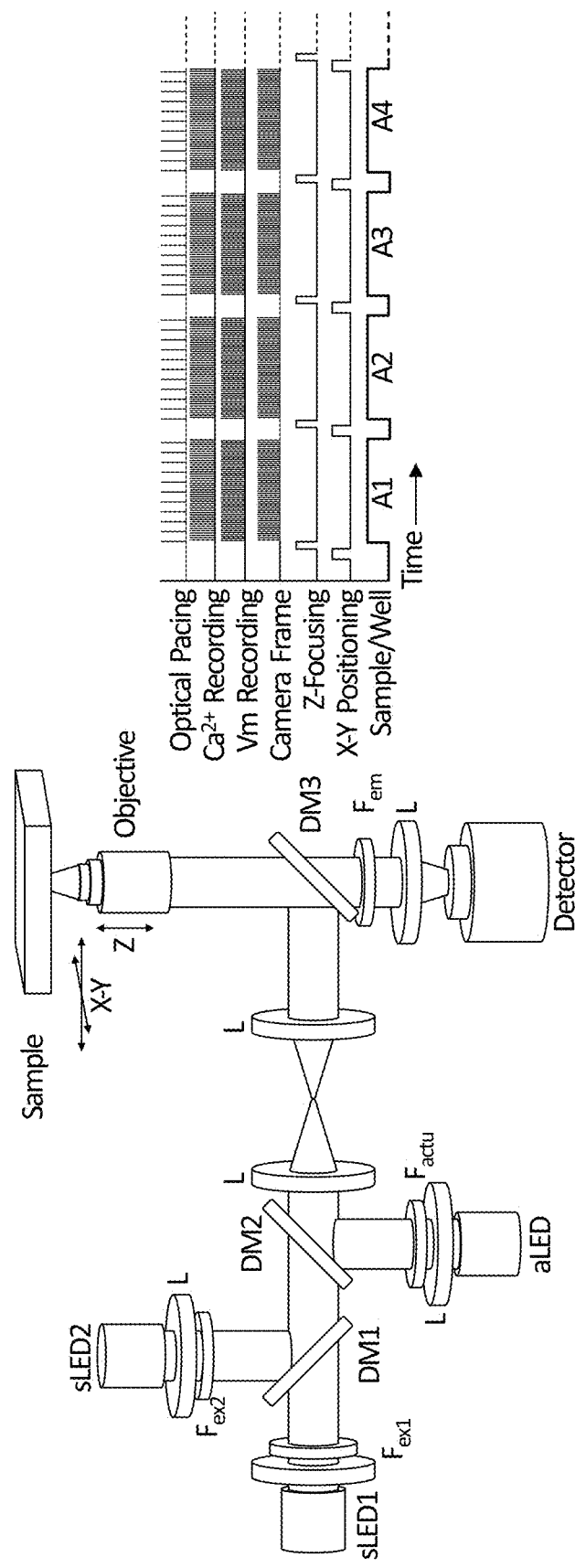

FIG. 22 is a schematic of an embodiment of an all-optical on-axis electrophysiology system in the context of imaging a multi-well plate. The two LEDs (sLED1 and 2) are gated by the detector, so that each frame alternately records signals illuminated by sLED1 then sLED2. Additionally, a third LED is used to provide optogenetic actuation (a fourth LED can also be included for other actuators). The light paths are combined using dichroic mirrors, then directed to the sample using the special multi-band dichroic, DM3 to the objective. Fluorescent signals are collected by the objective and directed to DM3 where they are split from the illumination path to a single detector. The system is said to be "temporally multiplexed" because the recorded signal channels are separated temporally (through fast switching between frames).

DETAILED DESCRIPTION

The present disclosure relates generally to bio-photonic devices or cells and cell cultures including bio-photonic devices and target cells. The present disclosure also relates to methods of preparing cell cultures including bio-photonic devices and target cells. Methods of analyzing the electrophysiology of target cells using the cell cultures are also disclosed. The present disclosure also relates to systems for analyzing the electrophysiology of target cells.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

A system has been developed for HT cardiac electrophysiology and electromechanics. The system includes a method for combined optical pacing and optical recording (also referred to herein as all-optical electrophysiology) from a variety of primary and stem-cell-derived cells and tissues, hardware, automation, and analysis software.

The system can be used to assist in multiple areas of the preclinical stage of drug testing and development. It can be used to better predict cardiotoxicity while still in the preclinical drug trial phase while not solely relying on current overly simplified metrics. The system can also be used in early drug discovery phases for screening for specific ion channel targeting drugs.

The system can also be used for phenotyping iPSC-CMs and other excitable cells and characterizing other biologics. Additionally, due to its contactless nature, it can be used for long-term studies. Because of its fast, cost-effective, HT nature, the system can also be used for quality testing of drugs in production.

Additional benefits to system provided herein: it is cost effective (<$100,000) to implement and is straightforward to implement, unlike traditional methods for studying cardiac EP. Furthermore, the technology is not just limited to specific cell types, including other excitable cell types (e.g., neurons, muscle cells, etc.), and it can be used for characterizing induced pluripotent stem cells (iPSCs).

Figure 1:
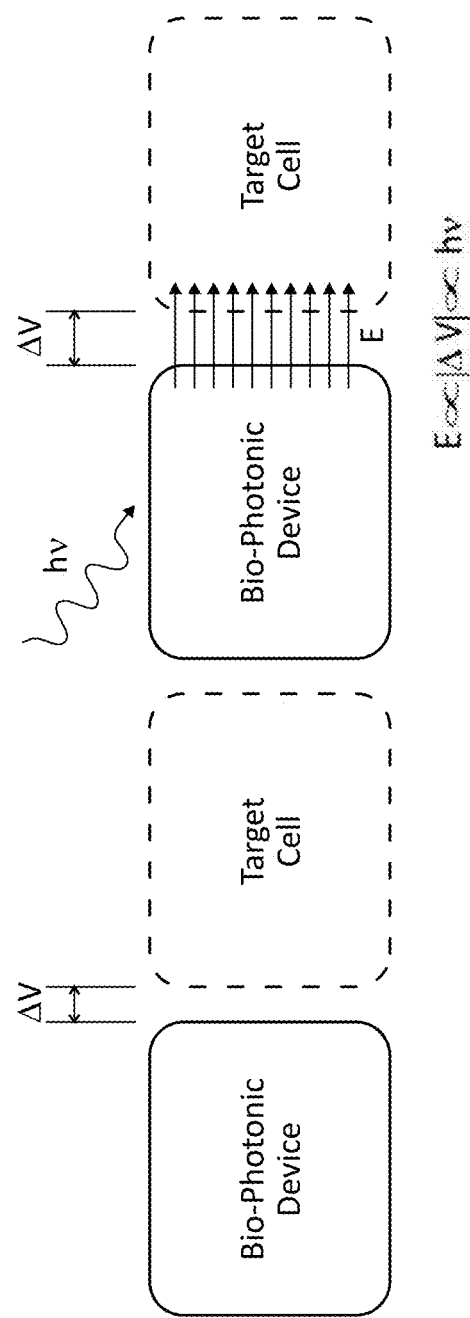
FIG. 1 is a conceptual illustration of bio-photonic cells or devices using photon-energy to generate a localized electric field capable of affecting the membrane potential of a target cell.
Figure 2:
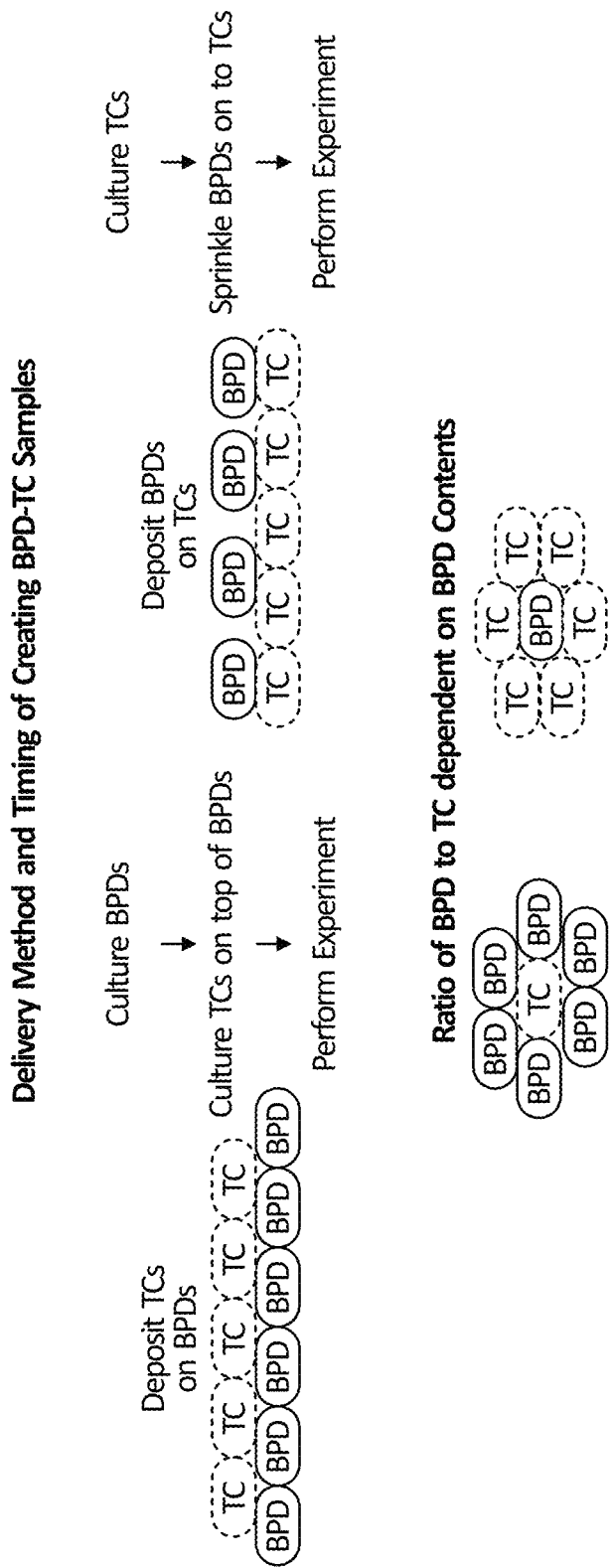
FIG. 2 is an outline of the delivery method and timing of bio-photonic device/target cell combination. The target cells can either be deposited on top of a pre-existing layer of bio-photonic devices, or the bio-photonic devices can be "sprinkled" on top of the target cells. The deposition of the bio-photonic device and target cell can be simultaneous or sequential in time and spatially-patterned for localized effects and/or variable ratios. Functional and optimal target cell/bio-photonic device ratios are dependent on the intrinsic properties of the contents of the bio-photonic device. The intrinsic properties include the efficiency of the contained photonic devices or photonic entities to convert incident energy into changes in the localized electric field or other photons or the efficiency of the photonic device to convert an external substrate into photons.

The system may use bio-photonic cells or devices. As depicted in FIG. 1, the bio-photonic devices can use photon-energy to generate a localized electric field capable of affecting the membrane potential of a target cell. FIG. 2 illustrates some embodiments of delivery methods and timing for preparing bio-photonic device/target cell combinations. The target cells can either be deposited on top of a pre-existing layer of bio-photonic devices, or the bio-photonic devices can be "sprinkled" on top of the target cells. The deposition of the bio-photonic device and target cell can be simultaneous or sequential in time and spatially-patterned for localized effects and/or variable ratios. Functional and optimal target cell/bio-photonic device ratios may be dependent on the intrinsic properties of the contents of the bio-photonic device. The intrinsic properties include, but are not limited to, the efficiency of the contained photonic devices or photonic entities to convert incident energy into changes in the localized electric field or other photons or the efficiency of the photonic device to convert an external substrate into photons.

Figure 3:
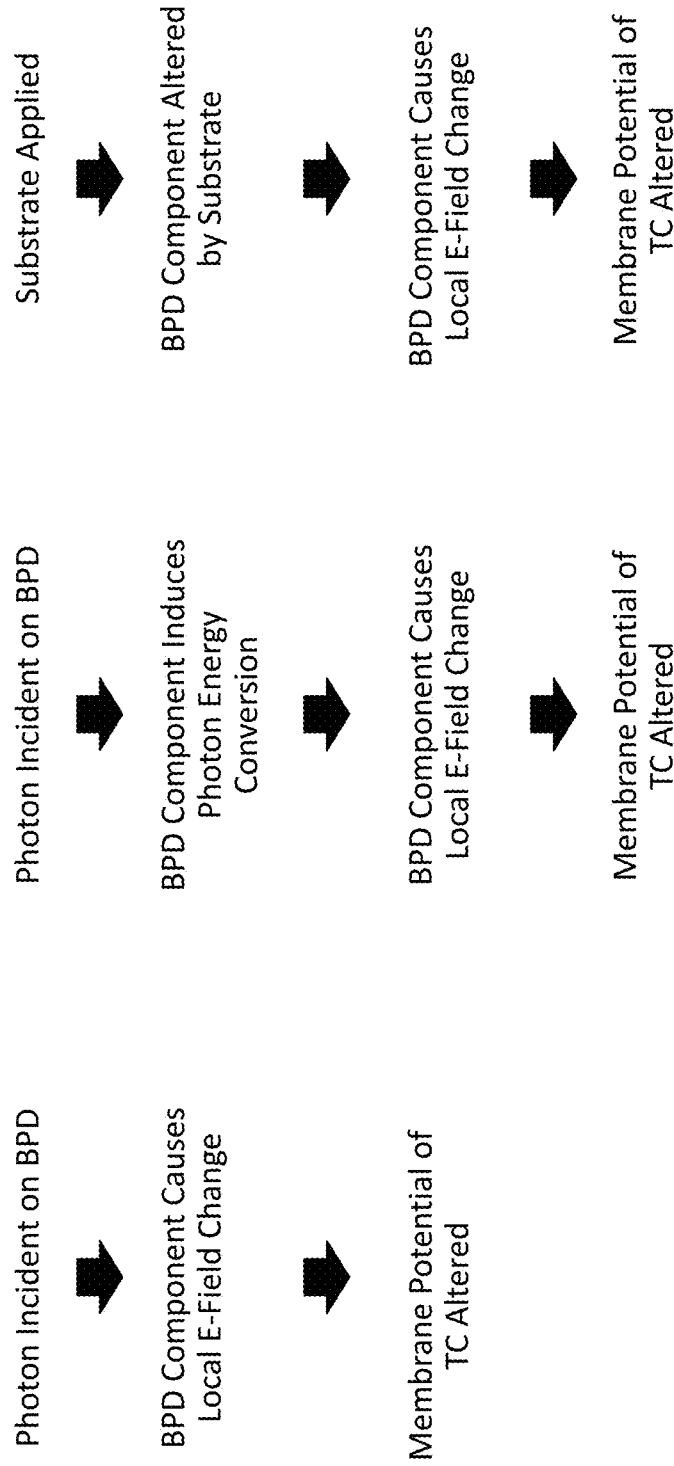
FIG. 3 is an outline of three examples of how bio-photonic devices can be used to affect the membrane potential of the target cells. The bio-photonic devices can have the optically activated component alone, a combination of an energy-conversion entity and an optically activated component, or a photon-emitting entity and an optically activated component.

FIG. 3 outlines three examples of how bio-photonic devices can be used to affect the membrane potential of the target cells. The bio-photonic devices can have the optically activated component alone, a combination of an energy-conversion entity and an optically activated component, and/or a photon-emitting entity and an optically activated component. The methods and systems shown in FIGS. 1-3 are described in further detail below.

Improvement of preclinical cardiotoxicity testing, discovery of new ion-channel-targeted drugs, and phenotyping and use of stem cell-derived CMs and other biologics can necessitate HT, cellular-level electrophysiological interrogation tools. Optical techniques for actuation and sensing can provide instant parallelism, enabling contactless dynamic HT testing of cells and small-tissue constructs, which are not generally affordable by other means. Here is shown, computationally and experimentally, limits of all-optical electrophysiology when applied to drug testing. OptoDyCE, a fully automated system for all-optical cardiac electrophysiology, is also implemented and validated. Optical actuation is validated by virally introducing optogenetic drivers in rat and human CMs or through the modular use of dedicated light-sensitive somatic "spark" cells. It is shown that this automated all-optical approach can provide HT means of cellular interrogation (i.e., allow for dynamic testing of >600 multicellular samples or compounds per hour) and yield high-content information about the action of a drug over time, space, and doses.

The development of new drugs can be lengthy and inefficient. The approval process alone takes, on average, seven to ten years (see Reichert, J. M. *Nat Rev Drug Discov* 2, 695-702, (2003)). In the United States, <0.05% of all compounds undergoing preclinical tests become marketed drugs, and <30% of compounds evaluated in clinical trials make it to market (see Preziosi, P. *Nat Rev Drug Discov* 3, 521-526, (2004)). Perhaps most costly, and with the greatest negative societal and ethical impact, is the withdrawal of drugs from the market after they have been approved. Insufficient or inadequate tools for predicting failure before more expensive phases of testing, both in animal and human, can drive up drug costs and decrease the desire for pharmaceutical companies to pursue more "high-risk" drugs that would result in little payout.

In 2004, it was estimated that a 10% improvement in failure prediction before clinical trials could save $100 million in development costs per drug (see FDA, U., Food & Administration, D. Challenge and opportunity on the critical path to new medical products. Rockville (Md.): FDA (2004)). Developing tools for improved failure prediction of a drug in earlier stages of the development process can reverse the current trends in the drug development process. In the last 40 years, over 20% of drugs discontinued at all phases of development, including discovery, preclinical and clinical evaluation, and post-market surveillance, have been due to cardiac toxicity where unintended interactions with cardiac ion channels result in proarrhythmic effects (see Piccini, J. P. et al. *Am Heart J* 158, 317-326, (2009)). In response, international regulatory agreements were developed that mandate testing of all new drugs, both cardiac and non-cardiac, for cardiac liability, including drug-induced long QT interval (LQT) and risk for development of life-threatening arrhythmias, such as Torsade de Pointes (TdP) (see Fermini, B. et al. *J Biomol Screen*, doi: 10.1177/1087057115594589 (2015)).

Figure 4:
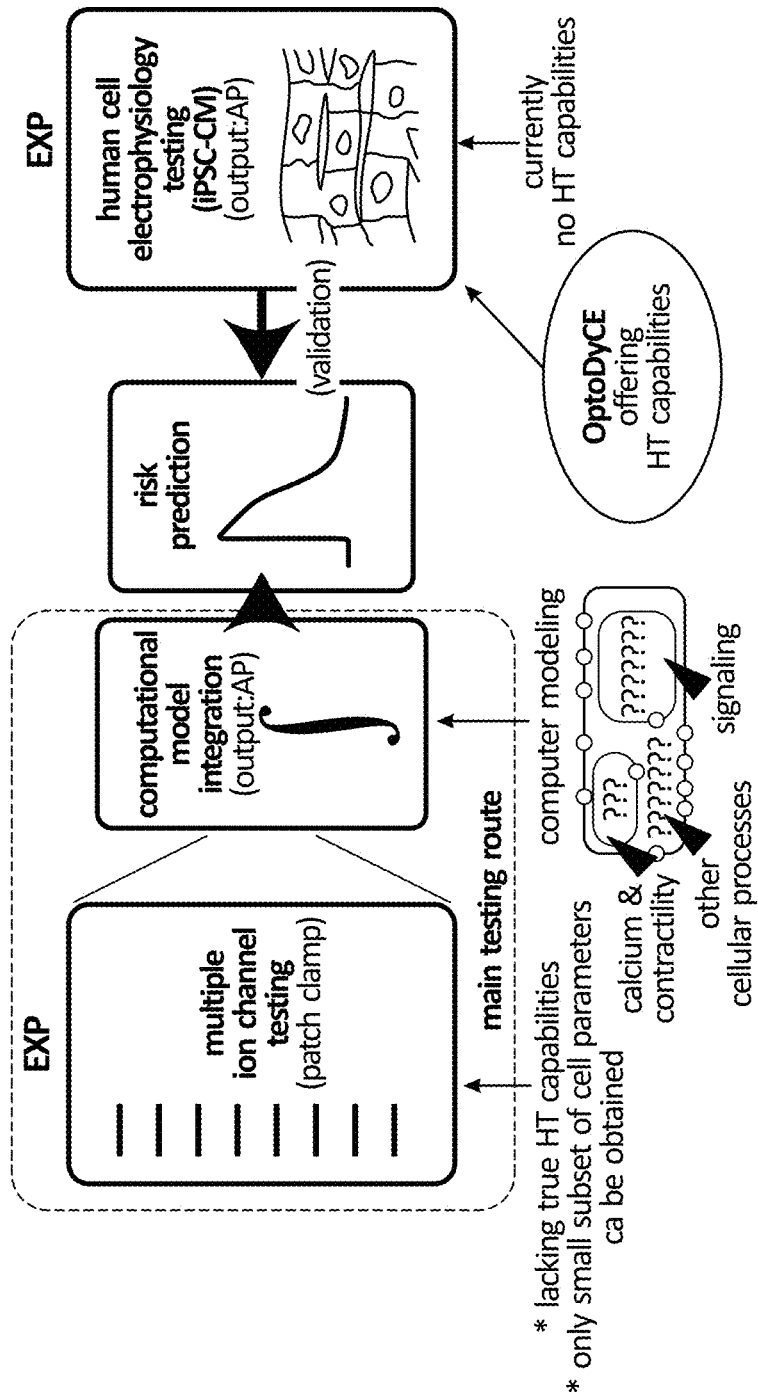
FIG. 4 depicts the CiPA concept (see Fermini, B. et al. *J Biomol Screen* (2015)), which aims to help change/improve current ICH (International Conference on Harmonization of Technical Requirements for Registration of Pharmaceuticals for Human Use—coordinated regulatory efforts by Europe, Japan, and the United States concerning pharmaceutical products) regulations for pre-clinical cardiotoxicity testing to avoid unnecessary drug attrition, reduce cost, and improve drug development. The arrhythmia risk is to be derived from experimental data using multi-channel testing by manual or planar automated patch clamp in recombinant expression systems (see IONWORKS® in Table 1), which are then integrated using computational tools to predict the overall action of a compound on human cell electrophysiology, i.e., on the action potential (AP)—this experimental step plus the computational step form the main testing route. The predictions (the effects of a compound on the human AP) are to be validated using cell electrophysiology measurements in human cardiomyocytes (CMs; most likely, iPSC-CMs). Note that, currently, both of the two experimental components in this scheme lack true HT capabilities. Planar patch systems have evolved but do not pass the HT threshold; CM electrophysiology (AP measurements) currently cannot be performed in HT fashion. The platform OptoDyCE, as provided herein, aims to bring HT capabilities to the cell-level testing in human CMs. This experimental approach (on the right) is more direct and can theoretically (pending maturation of the iPSC-CM technology)

Currently required preclinical cardiotoxicity testing (part of the drug-development process, see FIG. 14) specifically focuses on a drug's blocking action on the hERG $K^+$ channel that provides one of the main repolarizing currents in CMs. The blocking of this channel impacts repolarization and is often associated with LQT and thus with increased risk of TdP. However, it has recently been recognized that a drug's proarrhythmic effect, or "torsadogenicity," is often shaped by its action on multiple ion channels, where the net effect may be different than the outcome of a simple HERG $K^+$ channel block (see Fermini, B. et al. *J Biomol Screen*, doi:10.1177/1087057115594589 (2015); Bowlby, M. R., et al. *Current drug metabolism* 9, 965-970, (2008); Mirams, G. R. et al. *Cardiovasc Res* 91, 53-61, (2011); Redfern, W. S. et al. *Cardiovasc Res* 58, 32-45, (2003); and Rodriguez, B. et al. *Clinical pharmacology and therapeutics* 88, 130-134, (2010)). Indeed, there are hERG $K^+$ blockers that are known to not cause TdP (e.g., ranolazine or verapamil), resulting in false positives by the current testing methodology. Likewise, drugs with minor effect on the hERG $K^+$ channel but causing TdP (e.g., tedisamil), produce false negatives (see Mirams, G. R. et al. *Cardiovasc Res* 91, 53-61, (2011)). As a result, an integrative approach (both cell-level and multicellular) may be useful, and current regulations may need to be revisited (see FIG. 4 showing an overview of the CiPA concept (see Fermini, B. et al. *J Biomol Screen*, doi:10.1177/1087057115594589 (2015))). Computational efforts are underway (see Mirams, G. R. et al. *Cardiovasc Res* 91, 53-61, (2011) and Rodriguez, B. et al. *Clinical pharmacology and therapeutics* 88, 130-134, (2010)) to integrate multi-channel data obtained in recombinant expression systems (non-myocytes) to predict the action of a drug on the human cardiac AP (see FIG. 4).

While computational models can be powerful in simulating a wide range of conditions, they still require validation and generally rely on extensive experimental data for individual ion channels. Additionally, these data have their limitations due to being obtained in non-myocytes and by non-HT technology. This type of experimental data (e.g., patch clamp data on select ion channels, see FIG. 4) can still leave the computational models under-constrained. This high level of uncertainty can result from missing detailed information on calcium and contractility handling as well as important intracellular signaling aspects. For example, models incorporating even an extensive ion channel data set, obtained using patch clamp in non-myocytes, may not be able to predict the proarrhythmic effects of a leukemia drug like ponatinib, a tyrosine kinase inhibitor, or other non-classic multi-target regulators of electrophysiology.

An alternative, more direct, and relevant experimental test bed for drug/cardiotoxicity screening may be provided by direct cell-level measurements in CMs. In particular, human patient-derived CMs (induced pluripotent stem cell derived iPSC-CMs) show potential, considering recent strides in their optimization and production-scaling (see Bellin, M., et al. *Nature reviews. Molecular cell biology* 13, 713-726, (2012) and Khan, J. M., et al. *Br J Pharmacol* 169, 304-317, (2013)). The use of iPSC-CMs can provide a venue for patient-specific drug-testing, as acquiring native human heart tissue from the patient is generally undesirable and not scalable for use in HT technology (see FIG. 14). The functional data obtained in myocytes by HT technology may not only yield an independent risk assessment of a drug on human cardiac electrophysiology but may also help improve and constrain computational models developed in this area. However, there are currently no HT solutions (i.e., having the ability to screen>10,000 compounds a day) for performing robust CM EP testing.

Classic electrophysiology involves physical contact and therefore is inherently very low throughput (i.e., manual). New technical developments towards increased throughput (see Dunlop, J., et al. *Nat Rev Drug Discov* 7, 358-368, (2008) and Fertig, N. et al. *Future medicinal chemistry* 2, 691-695, (2010)) include the automated planar patch, IONWORKS® by MOLECULAR DEVICES™, at the single-channel level; the Fluorometric Imaging Plate Reader (FLIPR®) by MOLECULAR DEVICES™; MAESTRO™ Multichannel Electrode Arrays (MEAs) recording local field potentials by AXION BIOSYSTEMS™; impedance-based assays with XCELLIGENCE® by ACEA BIOSCIENCES™; and the kinetic plate reader FDSS/µCELL™ by HAMAMATSU™ for cellular measurements (see Table 1 below for a detailed comparison).

TABLE 1

| System | Description | PROS | CONS |
| --- | --- | --- | --- |
| IonWorks Molecular Devices 2-7 | Actuation: Electrical Sensing: Population patch clamp | Closest to classic ion channel characterization Fast readout Dynamic stimulation available | Limited throughput/expandability Limited spatial resolution Contact-requiring Not robust (needs "well behaved" cell lines; not applicable to any primary cells or mini-tissues) No calcium/contractility measurements High complexity; custom plates High cost |

TABLE 1-continued

| System | Description | PROS | CONS |
| --- | --- | --- | --- |
| Maestro Multichannel Electrode Array (MEAs) Axion Biosystems 2, 1741 | Actuation: Electrical Sensing: Local field potential | Label-free Long-term recording possible Fast readout Dynamic stimulation available | Limited throughput/expandability Limited spatial resolution Contact-requiring Not robust (not applicable to mini-tissues) No direct measurements of action potentials, calcium or contractility High complexity; custom plates |
| xCELLigence Acea Biosciences 8, 12, 13 | Actuation: Electrical Sensing: Impedance | Label-free Long-term recoding possible | Limited throughput/expandability Tracks only slow processes Limited spatial resolution Contact-requiring Not robust (not applicable to mini-tissues) No direct measurements of action potentials, calcium or dynamic contractions High complexity; custom plates High cost |
| FLIPR Molecular Devices 3, 7, 14, 15 | Actuation: Chemical Sensing: Optical (fluorescence) | Highly parallel Contactless Optical readout | No dynamic stimulation Slow readout No spatial information Not robust (not-applicable to mini-tissues) No direct measurements of action potentials or contractility High complexity; custom plates High cost |
| FDSS/μCell Hamamatsu 14, 16 | Actuation: Chemical (or electrical field) Sensing: Optical (fluorescence) | Highly parallel Contactless Optical readout Dynamic stimulation available | Limited dynamic stimulation Relatively slow readout (typical <5 fps) No spatial information (low SNR) Not robust (not applicable to mini-tissues) No direct measurements of action potentials or contractility High complexity; custom plates High cost |

The following limitations of these systems motivate the need for further developments towards HT cell-level electrophysiology. 1) Requirements for contact can prevent scaling to the HT-level (a non-contact modality is desirable). Examples of contact-requiring systems include IONWORKS®, MEAs, and XCELLIGENCE®. 2) Lack of electrophysiologically-relevant fast readout can prevent tracking of fast APs. Optical sensing using FLIPR® and the FDSS/μCELL™ system for cellular measurements are highly parallel but are unable to capture AP morphology with high temporal resolution. 3) Inability for dynamic actuation (pacing with adaptable protocols) and frequency-response testing (e.g., FLIPR®), which is quite relevant in drug-induced cardiotoxicity (see Moreno, J. D. et al. *Sci Transl Med* 3, 98ra83, doi:10.1126/scitranslmed.3002588 (2011)). 4) Cell-type restrictions: more phenotypic outputs, such as iPSC-CMs or primary CMs as test beds, are desirable rather than the currently-employed recombinant expression systems. However, handling limitations present challenges (e.g., in IONWORKS®, a proper seal can be reliably formed only with "well-behaved" cell lines (see Dunlop, J., et al. *Nat Rev Drug Discov* 7, 358-368, (2008)). 5) None of the current automated systems can characterize tissue-level/ multicellular effects, in 2D or 3D, even though arrhythmias are inherently spatio-temporal phenomena. An all-optical EP approach (see Ambrosi, C. M., et al. *Prog Biophys Mol Biol* 115, 294-304, (2014); Entcheva, E. *Am J Physiol Heart Circ Physiol* 304, Hi 179-1191, (2013); and Hochbaum, D. R. et al. *Nat Methods* 11, 825-833, (2014)) can overcome these limitations and facilitate HT-level cellular testing through built-in parallelism. The contactless optical stimulation and readout can be used over millions of locations simultaneously, including three-dimensional settings. Such a system has not been realized to date.

OptoDyCE is an automated platform for all-optical dynamic interrogation of CM electrophysiology. By employing optogenetic tools, dynamic interrogation of multiple cell types is able to be performed, including human iPSC-CMs in monolayers or in small three-dimensional cell constructs, with applicability to drug testing. While OptoDyCE can work with various experimental systems, its combination with scalable (i.e., HT-compatible) models, like stem-cell-derived CMs and small engineered cardiac syncytia, can be relevant to the drug screening and testing process (see FIG. 14). The HT capabilities of OptoDyCE are demonstrated using multicellular samples in 96-well format by combining optogenetic actuation with simultaneous optical sensing of voltage, intracellular calcium, or contractility by synthetic red-shifted dyes or dye-free video tracking. OptoDyCE can permit the fast quantification of CMs' EP and electromechanical response to a drug over time and space at both the cellular and global scale.

Considerations for Applying Optogenetics to Drug Testing

New fast optogenetic tools for optical stimulation (actuation) (see Nagel, G. et al. *Biochem Soc Trans* 33, 863-866, (2005); Nagel, G. et al. *Proc Natl Acad Sci USA* 100, 13940-13945, (2003); and Abilez, O. J. *Conference proceedings: . . . Annual International Conference of the IEEE Engineering in Medicine and Biology Society. IEEE Engineering in Medicine and Biology Society. Annual Conference* 2012, 1386-1389, (2012)) and recording (sensing) (see Hochbaum, D. R. et al. *Nat Methods* 11, 825-833, (2014); Dugue, G. P., et al. *Progress in brain research* 196, 1-28, (2012); and Leyton-Mange, J. S. et al. *Stem Cell Reports* 2, 163-170, (2014)) can offer solutions for the observation and fine control of multiple cells simultaneously, but their limitations must be considered in the context of drug screening (see FIG. 15). Both optogenetic actuators and sensors are biological entities that contain essential elements of ion channel proteins, making them potentially susceptible to the drugs being tested. The extent of such undesirable effects on the EP response of the cells of interest is considered. The action of a fast optogenetic actuator, e.g., Channelrhodopsin-2 (ChR2), that provides only a short stimulation impulse in CMs can be viewed as time-detached from the EP response (see FIG. 15, panel "a"), hence mostly benign. Indeed, it is shown computationally that for brief light pulses, even dramatic hypothetical drug effects on the ChR2 current amplitude and/or kinetics are practically inconsequential for the optically-triggered APs and CTs, as long as light irradiances are maintained at supra-threshold levels relative to what is required to activate ChR2 (see FIG. 15, panels "b"-"f"; details in Computational Analysis of Optogenetics and Cell Coupling in EXAMPLES below). In contrast, an optogenetic sensor, e.g., the voltage sensor VSFP2.3 (see Akemann, W., et al. *Biophys J* 96, 3959-3976, (2009)), is continuously engaged and thus fully temporally-convolved with the EP response (see FIG. 15, panel "a"). Even a mild drug action on the sensor can profoundly alter the EP readout (see computational predictions, FIG. 15, panel "g"). The same applies to other voltage (see Hochbaum, D. R. et al. *Nat Methods* 11, 825-833, (2014) and Leyton-Mange, J. S. et al. *Stem Cell Reports* 2, 163-170, (2014)) or calcium (GCaMP) optogenetic sensors, even if they exhibit superior kinetics compared to VSFP2.3. While suitable for long-term monitoring (order of days to months) (see Leyton-Mange, J. S. et al. *Stem Cell Reports* 2, 163-170, (2014)), channel-based optogenetic sensors may not be ideal for acute (order of minutes to hours) drug-testing applications due to such potential direct interference; instead, classic synthetic optical dyes for voltage and calcium or dye-free imaging may be more suitable, as they are already used in industrial applications.

The OptoDyCE System for Cardiac Electrophysiology

Provided herein is OptoDyCE, an automated system for all-optical dynamic cardiac electrophysiology testing at the cellular/multicellular level, which combines optogenetic actuation via ChR2 (or other opsins) with simultaneous optical sensing of voltage or intracellular calcium by synthetic red-shifted dyes (di-4-ANBDQBS and Rhod-4™, AM, respectively) or other dyes spectrally-shifted with respect to the optical actuator, e.g., ChR2, or dye-free video-tracking of contraction. The HT capabilities of OptoDyCE are illustrated with multicellular samples in 96-well format (see FIG. 16).

For several decades, optical techniques, including video recording of mechanical contractions and optical imaging of APs and CTs obtained by employing synthetic dyes and more recently, by optogenetic probes, have provided understanding of cardiac electrophysiology. However, their integration with optical pacing (for all-optical electrophysiology (see Hochbaum, D. R. et al. *Nat Methods* 11, 825-833, (2014) and Burton, R. A. B. et al. *Nature Photonics*, doi: 10.1038/nphoton.2015.196 (2015)) is a key development for cardiotoxicity testing because of the frequency-dependent aspect of drug actions and arrhythmia predictions (see Moreno, J. D. et al. *Sci Transl Med* 3, 98ra83, (2011)). Therefore, parallelism/scalability in both stimulation and recording can be crucial to increasing throughput when testing a dynamic system like cardiac tissue for instabilities (arrhythmias).

In OptoDyCE, contactless optical pacing reliably triggers voltage ($V_m$) and calcium ($[Ca^{2+}]_i$) signals, as well as quantifiable mechanical contractions, in either primary cardiomyocytes, e.g., neonatal rat ventricular myocytes (NRVMs), or stem-cell-derived cardiomyocytes, e.g., iPSC-CMs, in both cell monolayers and 3D structures (experimental data in FIG. 16, panels "a," "b," and "e"; see also FIGS. 5A-6B). The ability for optical pacing can be imparted via one of two quick and efficient transduction methods applied within 24 to 48 hours prior to experimentation to yield: 1) OptoHTS: using direct adenoviral gene delivery in human (ChR2-hiPSC-CM) or neonatal rat ventricular CMs (ChR2-CM) (see Ambrosi, C. M., et al. *Prog Biophys Mol Biol* 115, 294-304, (2014); Williams, J. C. et al. *PLoS Comput Biol* 9, e1003220, (2013); and Ambrosi, C. M., et al. *Methods Mol Biol* 1181, 215-228, (2014)) or 2) sOptoHTS: "sprinkling" of dedicated light-sensitive "spark" cells on top of samples of non-transduced CMs, a version of a "tandem-cell-unit" concept (see Jia, Z. et al. *Circulation. Arrhythmia and electrophysiology* 4, 753-760, (2011)) (see FIG. 16, panels "c"-"e"; see also EXAMPLE 3 below).

OptoHTS is validated by comparing AP and CT morphology of optically-stimulated ChR2-CM samples and electrically-paced non-transduced CM samples, confirming that optogenetic pacing is a suitable alternative to electrical stimulation for drug testing purposes (see FIG. 16, panels "f" and "g"), as predicted computationally (see Williams, J. C. et al. *PLoS Comput Biol* 9, e1003220, (2013) and Williams, J. C. et al. *Biophys J* 108, 1934-1945, (2015)). sOptoHTS provides an attractive, modular method of light sensitization: a bank of generic "spark" cells (light-sensitized somatic cells, including immortal cell lines) can be used in conjunction with a variety of non-modified experimental cardiac systems. Eliminating the need for genetic transformation of the target cells and the associated efforts for optimization of gene delivery in each studied cell type constitute advantages of sOptoHTS. However, caution may be applied regarding the geometry of the "spark" cell distribution, since loading effects of higher "spark"-cell concentrations can locally shorten the AP (see FIGS. 7A, 7B, and 16, panel "h"), while still having minimal effects on CT morphology. Proper "spark"-cell delivery, such as a localized/patterned pacing site (see Ambrosi, C. M., et al. *Scientific Reports*, doi:10.103B/srep17350 (2015)), can address the issue.

A fully automated HT version of OptoDyCE in 96-well format is demonstrated herein using an optical setup, custom-built around an inverted microscope employing a high-speed camera, an automation protocol, and custom-developed software for semi-automated analysis (see FIGS. 11 and 16, panels "i" and "j"). In the current proof-of-concept implementation of OptoDyCE, dynamic drug-dose testing using a multi-beat pacing protocol can be performed on a 96-well platform in less than 10 minutes (see FIGS. 8 and 17, panel "a"). High spatio-temporal resolution video recordings obtained by the system in these 10 minutes can provide over 30,000 single-cell readouts per 96-well plate, probed by multiple pacing stimuli. These records can be investigated at both the global and cellular scale to assess proarrhythmic risk by quantifying shape and duration parameters of the voltage, calcium, or contraction responses, and also sub-cellular spontaneous $Ca^{2+}$ release (SCR) events, instabilities in intracellular calcium (see FIGS. 9A-9C), abnormalities in the AP morphology, e.g., early afterdepolarizations (EADs) (see FIGS. 10A-10C), as well as abnormal mechanical activity (aftercontractions) (see FIG. 19, panels "a" and "b"). The system has been designed to be easily and economically adopted, compared to a prior report on all-optical electrophysiology in neurons (see Hochbaum, D. R. et al. *Nat Methods* 11, 825-833, (2014)).

Low-power LED light sources and portable, modular components allowing straightforward customization can be used.

Drug Dose-Response Testing Using OptoHTS

In order to validate the OptoDyCE system as well as illustrate the range of dynamic information that can be obtained, the well-understood class-IV antiarrhythmic agent nifedipine was chosen to perform drug dose-response testing. The drug was applied in 12 doses (0 to 50 µM) to 96 ChR2-CM samples (see FIG. 17, panel "a"). Using optical pacing at 1 Hz, the dose-response to nifedipine was quantified in terms of AP duration (APD) and CT duration (CTD) (see FIG. 17, panels "b"-"g"). Expected APD shortening (see FIG. 17, panels "b"-"d") and CTD shortening (see FIG. 17, panels "e"-"g") were observed, especially at the plateau phase (APD25/CTD25 and APD50/CTD50), due to nifedipine blocking the inward L-type calcium current, $I_{CaL}$. Nifedipine caused CTD to monotonically decrease up to 10 µM (see FIG. 17, panels "f" and "g"). In contrast, after maximum APD shortening at around 1 µM, corresponding to maximum block of $I_{CaL}$ reached at that concentration (see FIG. 17, panel "d" inset), the APD response to nifedipine reversed its direction, as seen clinically (see Redfern, W. S. et al. *Cardiovasc Res* 58, 32-45 (2003)). This may be due to indirect (voltage-mediated) or non-specific action on other ion channels, partially countering the $I_{CaL}$ block (see FIG. 17, panel "d"). Note that the benefits of the in vitro HT platform disclosed herein are in the ability to quickly and finely probe many concentrations and to help determine the "therapeutic window," i.e., the window for which a drug is both effective (has the desired action) and safe.

Clinically, the drug-metabolizing action of the cytochrome P450 enzymes present in cells can amplify or suppress the effect of a drug resulting in a lower or higher apparent drug dose (as in some failed drugs (see Preziosi, P. *Nat Rev Drug Discov* 3, 521-526, (2004))); the present data can be used to judge the "room for error" in the therapeutic window for a drug.

Validation of Functional Drug Testing Using sOptoHTS

The development of sOptoHTS using dedicated "spark" cells was motivated, at least in part, by the search for a simple and quick solution for optical actuation without genetically modifying the target cells (CMs) under investigation. The genetic modification of primary CMs or iPSC-CMs to make them light-sensitive in OptoHTS can require optimization that may be cell type or clone specific. In contrast, a stable "spark" cell line can be an attractive solution for industrial applications as it may not require any development on the user end; it can be provided as a simple reagent to be added ("sprinkled") shortly before experimentation (24 hours); and a variety of somatic (non-excitable) cells can serve as donor "spark" cells for optical actuation, including cardiac fibroblasts.

To validate sOptoHTS, the dose-dependent effects of nifedipine and of dofetilide were further compared using the two methods, OptoHTS vs. sOptoHTS (see FIG. 18). Dofetilide, a class-III anti-arrhythmic agent and intended hERG channel blocker, has a known risk for drug-induced LQT and TdP due to its APD-prolonging action (see Redfern, W. S. et al. *Cardiovasc Res* 58, 32-45 (2003)), making it a suitable choice for validating the system's ability to discern both APD-shortening (nifedipine) and APD-prolongation (dofetilide) for use as a drug-testing platform. sOptoHTS was able to successfully track the drug-dose dependent effects on APD and CTD, similar to OptoHTS (see FIG. 18, panels "a"-"d"). With proper tuning of the "spark" cell distribution, this simple and modular approach provided by sOptoHTS can be applied to HT EP drug testing.

Dynamic Functional Probing Over Time and Space by OptoDyCE

EP responses can be frequency-dependent; therefore passive observation of spontaneous activity (see Leyton-Mange, J. S. et al. *Stem Cell Reports* 2, 163-170, (2014)) is generally insufficient in drug testing and for arrhythmia assessment. Unlike most currently-employed systems (see Table 1), the present platform allows for active dynamic interrogation, such as robust pacing protocols that can reveal $V_m$, $[Ca^{2+}]_i$, or contraction's frequency response (restitution) and temporal instabilities (see FIGS. 6A, 6B, 9A-10C, and 19, panel "a"). For example, a consistent generation of voltage instabilities known as alternans can be captured at 2 Hz optical pacing in the presence of 2 µM dofetilide due to drug-induced APD prolongation (see FIG. 19, panel "b").

Restitution and temporal or spatial variability assessed by MAD (see EXAMPLE 9 below) can be quantified as a function of drug dose (see FIG. 19, panels "c"-"h"). These can be directly relevant to the "torsadogenicity" of a drug, providing a more complete assessment than traditional (single-channel block) testing or current state-of-the-art assays (see Table 1). The dynamic testing data reveal that nifedipine action on peak calcium (% change) is dose-dependent ($p<0.05$ obtained using ANOVA test followed by a Tukey-Kramer post hoc correction for multiple comparisons) but frequency-independent (see FIG. 19, panels "c" and "d"). Furthermore, nifedipine reduces temporal variability of peak calcium (assessed by MAD), and this reduction is augmented by higher-frequency pacing (see FIG. 19, panel "e"). For dofetilide, enhanced relative APD50 prolongation was found at higher frequency, which is opposite to purported reverse-use dependence (see FIG. 19, panels "f" and "g").

Triggered proarrhythmic events resulting in drug-dose related temporal variations in AP morphology, including dose-dependent increase in EADs, can be revealed in optically paced samples treated with dofetilide (see FIGS. 10A-10C). Furthermore, because of the ability to study multicellular samples, spatial variability can be quantified as a function of drug dose by analyzing individual cells or ROIs within the same sample/well (see FIG. 19, panel "h"; see also FIGS. 8-9C). For example, it was found that dofetilide at 2 µM increases spatial variability in APD (i.e., increases dispersion of repolarization—a known proarrhythmic factor), compared to control during 1 Hz pacing ($p<0.05$ for APD50 obtained using ANOVA test followed by a Tukey-Kramer post hoc correction for multiple comparisons). Dispersion of repolarization and abnormal AP events (e.g., EADs), in addition to being caused by heterogeneous block of the delayed rectifier $K^+$ channel (upon application of dofetilide), can also be linked to localized SCR—a recognized factor in the development of life-threatening arrhythmias, including drug-triggered events, and a hallmark of heart failure (see Johnson, D. M. et al. *Circ Res* 112, 246-256, (2013)). By recording multi-cellular samples with cellular-level resolution, SCR events triggered by a drug can be identifiable, which may not be observed in the global traces (see FIGS. 9A-9C).

OptoDyCE can elevate cellular electrophysiology to the HT level. The ability for highly-parallel dynamic stimulation can be a key component of assessing arrhythmia propensity. While non-optogenetic (mostly thermally-mediated) solutions are being pursued, opsin-based stimulation cannot be matched in terms of low energy, reliability, and precision. It is shown, computationally and experimentally, that optogenetic stimulation does not generally interfere with the EP response of CMs and it can be realized in several simple ways. The sOptoHTS method with sprinkled "spark" cells can be used for drug testing. The sOptoHTS method does not require genetic modifications in the studied cells and can be incorporated in the current manufacturing workflow provided herein. Furthermore, the computational analysis provided herein illustrates that optogenetic sensors, which are often derived from ion channel modules and other druggable components, may not be desirable in acute drug testing due to the temporal convolution of their response with the measured parameter of interest (AP or CT). While they can be useful reporters of activity long-term and in vivo, their use in the context of drug testing must generally be validated. Instead, here it is shown that spectrally-suitable synthetic optical sensors can work well.

OptoDyCE can meet the HT standard (see FIG. 14). "High-throughput" or "HT" in the industrial setting of drug discovery and testing implies capability of performing over 10,000 assays a day (see considerations in FIG. 8). HT can require that the samples and the process are scalable, manufacturing-friendly, and amenable to handling with standard liquid and cell dispensing robotics within a standardized plate-format setting. With robotic dispensing of cells and drugs, the 96-well format, demonstrated here, can be instantly upgraded to 384-well or other standard plate formats, with simple reprogramming. Thus, the present system is scalable. The current implementation has built-in parallelism within a well, interrogating hundreds of cells simultaneously (see FIGS. 8-9C), but generally relies on serial traversing of the wells; a macroscopic version (see Burton, R. A. B. et al. *Nature Photonics*, doi:10.1038/npho-ton.2015.196 (2015) and Entcheva, E. et al. *Prog Biophys Mol Biol* 92, 232-257, (2006)) of OptoDyCE with larger FOV can further increase throughput by order(s) of magnitude. The all-optical approach can also be applied for the quantification of a drug's action on cardiac conduction, including wave dynamics (see Burton, R. A. B. et al. *Nature Photonics*, (2015)), but with sacrifice of throughput due to space (spatial wavelength) generally required to accommodate such measurements.

The OptoDyCE framework is not limited to a particular experimental model. In addition to cultured cells, all-optical approaches can be used with cardiac tissue and whole hearts, including in vivo (see FIG. 14). The contactless nature of interrogation in OptoDyCE can make it versatile and applicable to non-planar, 3D samples (see FIG. 16), unlike the available technologies listed in Table 1. As illustrated in FIG. 14, OptoDyCE can elevate EP testing to HT status. This can require the experimental model to be HT-compatible, such as CMs and small engineered tissues that can be cultured. Despite recognized current problems with human iPSC-CMs, namely immaturity and variability (see Knollmann, B. C. *Circ Res* 112, 969-976, (2013)), there may not be better alternatives when HT-format assays are considered.

Native cardiac tissue (animal or human-derived) can generally provide a superior testing platform for assessing conduction abnormalities in a lower-throughput format (see FIG. 14). However, it may not be generally a suitable experimental target for the HT-level screening tests for several reasons: (a) there is limited availability of human heart tissue, and testing cannot generally be patient-specific because of the invasive nature of heart biopsies; (b) scalability is lacking due to spatial constraints—to make native tissue HT-compatible, the size of the individual tissue samples may have to be reduced/cut, creating issues with handling; (c) viability and stability—cultured cell systems are inherently better suited for industrial scale handling and more stable than organotypic cultures. Furthermore, pre-clinical testing in live animals can also play a key role, as systems-level effects may need to be probed. However, that is generally done in a low-throughput format at a later validating stage.

HT electrophysiology with OptoDyCE can allow for prediction of successful drug candidates as well as more informed failure prediction in order to reduce cost in later testing phases. The results provided herein may also illustrate the high-content data that can be obtained with the disclosed platform. The ability to simultaneously measure dynamically-controlled APs, CTs, and contractions, and to extract a large number of arrhythmia-relevant parameters, including, but not limited to, frequency-dependent morphological changes (alternans, EADs, DADs, aftercontractions) as well as SCR, temporal, and spatial variability of the response, can allow the quantification of a drug's proarrhythmic risk in a more comprehensive way than with any of the current platforms.

Such comprehensive evaluation of the cellular responses can be better suited to capture the effects of more recently acknowledged non-classical multi-target modulators of ion channels, such as kinase inhibitors, for example (see Lu, Z. et al. *Sci Transl Med* 4, 131ra150, (2012) and Yang, T. et al. *Circulation* 130, 224-234, (2014)), compared to patch-clamp data collection on a subset of individual ion channels, especially when done in non-myocytes. Drug effects mediated through intracellular signaling pathways, e.g., PI3K, may not be instantaneous and may be likely to engage a large number of ion channels, in some of which the effects may be small or the measurements may be challenging (e.g., measuring the late sodium current) (see Lu, Z. et al. *Sci Transl Med* 4, 131ra150, (2012)). Though not directly demonstrated here, such delayed/chronic action can be studied with the provided platform, as cultured systems can be stable over the relevant time frame (order of hours) and integral readouts (APs, CTs) can be better and more relevant measures of such complex effects. A limitation of the optical interrogation methods, discussed here, compared to direct electrical measurements, may be the difficulty in assessing absolute values, e.g., resting membrane potential or diastolic calcium levels. Even with ratiometric measurements (using dual-wavelength sensors), calibration can be difficult to apply in a HT setting. Nevertheless, drug-induced relative changes in these parameters can be inferred by the multitude of other measurements as they may directly influence the excitability and stability of the electrical response.

The high-content data may present a challenge for automated processing but also an opportunity. Data mining and analysis (e.g., principal component analysis) of such a massive number of outputs obtained in a self-consistent manner in the same experimental system under the same conditions can provide a unique opportunity to design classifiers of a compound's cardiotoxicity risk or of its ability to achieve desired safe modification of CM function. Such extensive high-quality data in response to a large number of known drugs can also be invaluable as means to tuning and constraining of currently pursued computer models for cardiotoxicity predictions at the cell and tissue level (see FIG. 4). By offering a currently missing option for automated HT CM electrophysiology, OptoDyCE can also impact developments concerning human iPSC-CMs (see Bellin, M., et al. *Nature reviews. Molecular cell biology* 13, 713-726, (2012) and Khan, J. M., et al. *Br J Pharmacol* 169, 304-317, (2013)) (see FIG. 4) by allowing for combinatorial optimization of factors involved in cell maturation, phenotype selection, and tissue engineering. In turn, the utilization of these new optimized human, potentially patient-specific, experimental models in conjunction with the provided HT testing platform may have the potential to improve pre-clinical drug testing, reduce cost, reduce animal use, and increase a therapy's likelihood of clinical success.

The pre-clinical process of drug discovery and testing can involve multiple stages with different objectives and different suitable experimental systems and assays. For cardiac electrophysiology applications, the top, HT type of assays can yield fast, massively-parallel coverage of a large number of compounds and combinations in order to eliminate high-risk items.

Secondary filters in the drug testing process for cardiac electrophysiology can be provided by medium to low throughput assays designed to test tissue-level/conduction properties. Engineered tissue equivalents may be suitable, but native cardiac tissue (animal or human-derived) can generally provide a superior testing platform for assessing conduction abnormalities in this lower-throughput format (see FIG. 14). Native tissue is generally not a suitable experimental target for the HT-level screening tests for several reasons. 1. Source and relevance: the excitement with stem-cell-derived myocytes (especially iPSC-CMs) is based on the idea that drug testing can become patient-specific. This cannot be achieved with native human heart tissue (i.e., patient heart biopsies are invasive and not desirable). There is a limited availability of donor human heart tissue, which varies a lot in state, patient age, drug and disease history, making it unsuitable for HT screening purposes. 2. Spatial constraints: HT inevitably means scaling-down the sample size, e.g., dramatically, to increase throughput within the same plate format. If native tissue is to be used (animal or human), it must be chopped up to very tiny pieces (in the sub-millimeter range) in order to provide independent samples and to make it amenable to HT-format measurements. This presents problems with handling and viability. An interesting alternative is to use a "patterned" drug application (via microfluidics) within a bigger tissue sample (see Chang, T. C. et al. *Lab Chip* 14, 4540-4551, (2014)). In the case of cardiac tissue, inherent electrical coupling between the cells and inherent spatial variations can present a problem for independent readouts. 3. Viability and sample stability: cultured cell systems are inherently better suited for industrial scale handling. They are easier to modify genetically in a consistent manner; they are functionally more stable over time than organotypic cultures, for example, which show rapid de-differentiation and loss of function, despite ongoing efforts to stabilize them (i.e., efforts to produce long-term cultured tissue slices) (see Brandenburger, M. et al. *Cardiovasc Res* 93, 50-59, (2012)). 4. Finally, the preclinical process requires testing of systems-level effects, which needs to be done in live animals and is low-throughput in nature. All-optical methods are compatible with experimental models across these stages, but they are generally most impactful at the HT level.

Bio-photonic devices or cells may include a synthetic cell body (e.g., a liposome) or real cell body (e.g., a HeLa cell, a CHO cell, an NIH/3T3 cell, a HEK293 cell, a fibroblast, a mesenchymal stem cell, an iPSC, an embryonic stem cell, a progenitor cell, etc.) including photon-sensitive or photon-generating entities (e.g., chromophores, nanoparticles, etc.) that have at least one of the following properties: 1) create a local electric field change induced by at least one of the following: a) a chromophore absorbing a photon and inducing a conformational change in an ion channel or other membrane-bound protein, such as ChR2 or other opsins and/or b) a nanoparticle or chromophore that is able to absorb photons and generate electric fields, such as plasmonic nanoparticles; 2) convert photons of a specific energy to a different energy by at least one of the following: a) multi-photon absorption; b) sequential-photon absorption up-conversion, e.g., up-conversion nanoparticles (UCNP); and/or c) possessing large non-linear coefficients performing second and higher-order harmonic generation, multi-wave mixing, or spontaneous parametric down-conversion; 3) emit photons without the presence of external photons, but rather the presence of a substrate, i.e., bioluminescence enzyme or hybrid (luminopsin).

Bio-photonic devices producing local electric field changes can be used to alter the membrane potential of neighboring target cells without the specific need of gap-junctions or connexins between the bio-photonic device and target cell and/or without relying on sufficient electric field strength at the membrane of the target cell allowed by at least one of the following: a) proximity of the bio-photonic devices and target cells and/or b) intrinsic properties of the chromophores/nanoparticles.

Bio-photonic devices containing energy-converting entities can be used for: activating photon-sensitive entities to induce a local electric field change, where the entities are either inside the bio-photonic device or target cell; and allowing for activation of photon-sensitive entities that are either inside the bio-photonic device or target cell at different wavelengths compared to what is intrinsically required to activate the photon-sensitive entities.

Bio-photonic devices carrying emitting-only entities can be used for: activating photon-sensitive entities to induce a local electric field change, where the entities are either inside the bio-photonic device or target cell; and allowing for activation of photon-sensitive entities that are inside the bio-photonic device or target cell without the need for an external light source.

Combined bio-photonic device/target cell cultures or samples can be generated by: sequential-in-time deposition or "sprinkling" bio-photonic devices on to already cultured target cells; sequential-in-time deposition of target cells on top of "substrates" of bio-photonic devices; and because gap junctions are not a prerequisite, the samples can be ready in less than 24 hours of combining the two cell types.

Bio-photonic devices capable of altering membrane potentials to impart light sensitivity on target cell samples: when combined with fluorescent reporters, all-optical EP measurements can be performed; provides a means of having high spatio-temporal control of target cells; allows standardization and consistency (bio-photonic devices can be manufactured in a highly controlled manner and provided as a reagent); does not require genetic modification of the target cells and permits their direct use/study without any added complexity.

An automated system for all-optical electrophysiology can be constructed that employs the bio-photonic device/target cell samples. The system can be low-energy and miniaturized. Deposition of bio-photonic devices can be fully automated using robotics.

Bio-photonic device/target cell samples combined with the automated system can be used to perform HT EP testing. Such testing can be for: ion-channel targeting drug screening; cardiotoxicity screening; cell phenotyping (e.g., functional characterization of stem-cell-derived CMs). Automated software can be used for processing the EP data obtained using the HT EP data.

An aspect of the disclosure relates to a bio-photonic device including a photonic device or photonic entity comprising a chromophore, a nanoparticle, or a combination of both a chromophore and a nanoparticle that absorbs radiation in the near UV (100 nm-400 nm), visible (400 nm-700 nm), and/or near infrared (700 nm-1,300 nm). When exposed to light, the bio-photonic device may undergo at least one of the following processes to induce a local electric field change: i) a conformational change that results in the state-change of an ion channel present in the cell causing an influx or efflux of ions; ii) a conformational change that results in the state-change of a non-ion channel protein present in the cell; or iii) forms a dipole to generate a localized plasmonic electric field strong enough to affect neighboring cells.

Another aspect of the disclosure relates to a bio-photonic device including a photonic entity comprising a chromophore, a nanoparticle, or a combination of both a chromophore and a nanoparticle that exhibits non-linear-optical properties in the near UV (100 nm-400 nm), visible (400 nm-700 nm), and/or near infrared (700 nm-1,300 nm). When exposed to light, the bio-photonic device may be capable of photon energy conversion via one of the following: i) multi-photon absorption; ii) sequential-photon absorption up-conversion; or iii) large non-linear optical coefficients for performing second and higher-order harmonic generation, multi-wave mixing, or spontaneous parametric down-conversion.

Another aspect of the disclosure relates to a photonic entity comprising either a chromophore, a nanoparticle, or a combination of both a chromophore and a nanoparticle that emits photons in the near UV (100 nm-400 nm), visible (400 nm-700 nm), and/or near infrared (700 nm-1,300 nm) without the presence of near UV, visible, and/or near infrared radiation, but rather at least one of the following: i) an external chemical substrate or ii) an external, localized electromagnetic field.

The bio-photonic device, as described above, may be non-excitable. For example, the bio-photonic device may not be able to fire an AP. The bio-photonic device may be a synthetic cell. For example, the synthetic cell may be a liposome. The bio-photonic device may be a non-excitable cell. For example, the non-excitable cell may be at least one of a HeLa cell, a CHO cell, an NIH/3T3 cell, a HEK293 cell, a fibroblast, a mesenchymal stem cell, an iPSC, an embryonic stem cell, a progenitor cell, any somatic non-excitable cell, and/or any other non-excitable cell.

The bio-photonic device may be combined with an exogenous photonic entity that can alter the energy requirements and/or the energy production of the bio-photonic device. The exogenous photonic entity may include one or more of the following: a) increased exogenous all-trans-retinal (ATR) to lower the power required to excite ChR2; b) a photonic entity that can alter the energy bands to induce a conformational change in a chromophore; c) a photonic entity that can alter the resonant frequency of a plasmonic nanoparticle; or d) a photonic entity that can alter the emitted energy from a photon-emitting photonic entity.

Another aspect of the disclosure relates to methods for altering the energy requirements and/or energy production of a bio-photonic device by application of an exogenous photonic device. The methods may include: a) increased exogenous ATR to lower the power required to excite ChR2; b) an exogenous photonic device that can alter the energy bands to induce a conformational change in a chromophore; c) an exogenous photonic device that can alter the resonant frequency of a plasmonic nanoparticle; or d) an exogenous photonic device that can alter the emitted energy from a photon-emitting photonic device.

Another aspect of the disclosure relates to a cell culture including the combination of one or more bio-photonic devices with target cells or target excitable cells, whereby the combination of bio-photonic devices imparts light sensitivity at specific energies on the target cells. In some embodiments, the cell culture can include target cells that were cultured first and wherein the bio-photonic devices were added later, and only less than about 3, about 6, about 12, or about 24 hours prior to analysis by light stimulation of the bio-photonic devices. In certain embodiments, the bio-photonic device may be plated first and the target cells may be added later and only less than about 3, about 6, about 12, or about 24 hours prior to analysis by light stimulation of the bio-photonic device. The cell culture may further include a fluorescent probe or reporter that emits light in response to electrical excitation of the target cells. In some embodiments, the light emitted by the fluorescent reporter may be of a different wavelength than the wavelength of light to which the bio-photonic device is most responsive.

Another aspect of the disclosure relates to methods for using a bio-photonic device to impart light sensitivity at specific energies on target cells. The methods may include providing strong enough optically induced electric field changes by: i) proximity between the bio-photonic device and a target cell; ii) an adequate number of photonic entities contained in the bio-photonic device to drive field changes; and/or iii) photonic entities that can convert photons to changes in the local electric field with sufficient efficiency. The methods may also include allowing sufficient proximity of the bio-photonic device to opto-electrically alter the membrane potentials of the target cell achieved: i) without the need for gap-junction proteins such as connexins and/or ii) within the minimum time required for appropriate proximity to be obtained (order of hours), rather than limited by the time course of cell-cell coupling to be obtained.

Another aspect of the disclosure relates to methods for placing a bio-photonic device in sufficient proximity to a target cell. For example, the bio-photonic device can be placed in sufficient proximity to a target cell by: a) sequential-in-time deposition or "sprinkling" bio-photonic device on to already cultured target cells; b) sequential-in-time deposition of target cells on top of "substrates" of bio-photonic devices; and/or c) because gap junctions are not a prerequisite, the samples can be ready in less than 24 hours of combining the two cell types.

Another aspect of the disclosure relates to methods for performing spatial and temporal manipulation using a bio-photonic device combined with a sample containing cells capable of firing APs (excitable cells). The methods may include a light provided by an external source to: i) optically activate photonic entities in a bio-photonic device capable of altering the membrane potential of neighboring cells and/or ii) activate photonic entities in the bio-photonic device capable of performing photon-energy conversion. The methods may include a light provided by an internal source: i) produced by exposing the photon-emitting photonic entities in the bio-photonic device to the correct substrate to produce photon emission and/or ii) used to activate other light-sensitive photonic entities in either the bio-photonic device or target cell to produce a membrane potential change in the target cell. The methods may include modulation of a light source by: i) using light pulses of sufficient time length to create enough energy to activate the target cells; ii) using light pulses at desired frequencies to activate the target cells; and/or iii) by temporally controlling administration of the external substrate. The methods may include spatial modulation of the light source.

Another aspect of the disclosure relates to methods for performing all-optical EP measurements in a sample. The methods may include: a) use of optical stimulation and/or b) use of fluorescent reporters for reading out EP signals.

Another aspect of the disclosure relates to portable, stand-alone imaging devices for performing all-optical EP measurements on a multi-well sample. The devices may include a compact imaging device including an imaging sensor, for example, that is a pixel array. The pixel array may include a CMOS detector, an EMCCD, a CCD, a single photon counting device array, an avalanche photodiode array, and/or a photomultiplier tube array. Furthermore, the devices may include adequate specifications determined by the fluorescent reporter, including: 1) a pixel well-depth capacity of sufficient size to capture the full range of the recorded signal; 2) dark counts well below the dynamic range of the recorded signal; and/or 3) a quantum efficiency large enough to capture the signal. The devices, when combined with the imaging optics, may: 1) capture activity across at least a 400 µm FOV or larger and/or 2) provide a resolution of at least 0.8 µm/pixel or smaller. The devices may include a readout rate sufficiently faster than the signal speed, a frame rate greater than about 200 frames/second, and/or may be a component of a smartphone camera.

In some embodiments, the devices may include light sources for exciting fluorescent reporters for imaging. The light sources may be incoherent sources (e.g., LEDs, including low-powered LEDs; OLED displays; and/or halogen, arc, or other high-powered incoherent sources). The light sources may be coherent sources (e.g., lasers). The light sources may be spectra having small bandwidths centered at the excitation wavelengths of the fluorescent reporter.

In certain embodiments, the devices may include light sources for providing photon-activation of the bio-photonic devices. The light sources may be incoherent sources (e.g., LEDs, including low-powered LEDs; OLED displays; the screen of a portable electronic device (e.g., the screen of a smartphone); halogen, arc, or other high-powered incoherent sources). The light sources may be coherent sources (e.g., lasers). The light sources may be low-powered (e.g., producing irradiances on the order of 1 mW/mm$^2$ depending on the energy requirements of the bio-photonic device). The low-powered light source may allow for use of miniaturized light sources and/or may be coupled to a spatio-temporal modulation device to project time varying signals on to the sample, for example, using a digital micro-mirror device (DMD) and/or a means of wave-front modulation (e.g., a liquid-crystal spatial light modulator and/or a dynamic holographic plate/film). The light sources may have spectra with small bandwidths and may be centered at the wavelengths to activate the bio-photonic device.

In various embodiments, the devices may include optics. The optics may include objectives: having numerical apertures (NAs) of at least 0.75; capable of imaging a FOV of at least 400 µm; being dry lenses; and/or capable of transmitting fluorescent excitation light and light to activate the bio-photonic devices to the sample. The optics may include interference filters: to narrow down the bandwidth of any illumination sources; to narrow down the bandwidth of emitted photons seen by the imaging sensor; and/or to act as dichroic mirrors to combine and transmit illumination light to the sample, and pass emitted light to the imaging sensor. The optics may include a series of lenses to project illumination light sources on to the sample, capable of illuminating over the whole ROI down to a diffraction-limited spot. The optics may include a series of lenses capable of projecting the emitted photons on to the imaging sensor with minimal distortion to maximize the effective spatial resolution of the device.

In some embodiments, the devices may include automated movement in the x-y plane: to address specific or all wells of the sample and/or to address multiple FOVs within a single well in the sample.

In certain embodiments, the devices may automatically focus on to the sample. Automated focus on the sample may be: performed after the device has positioned a new well over the objective; performed after positioning a new FOV; and/or to automate image collection in multiple sequential or non-sequential planes of the sample.

In various embodiments, the devices may include a manufactured, external housing unit containing one or more of the components described above. The housing unit may include a means of modularly exchanging: imaging devices, optics, and/or light sources. The devices may include a platform for securing the sample on to the device, data ports for computer-controlled communication with the components, and/or a means of environmentally sealing the contained components.

In some embodiments, the devices may include an environmental chamber (e.g., an incubator) for performing long-term experiments including: a heating element, gas control, an optically clear bottom-port for optical access to the sample to perform optical control and measurements, a means of mounting on to the portable device, and/or a means of electronically controlling and monitoring the chamber.

In certain embodiments, the devices may be compatible with a hermetically or otherwise sealed system: for performing contactless EP measurement with highly contagious or other biohazard materials and/or providing a means of not requiring separate systems for biohazardous and non-biohazardous materials due to the capacity to completely isolate the imaging systems from the sample.

In various embodiments, the devices may include a means of a remote control of the imaging system.

Another aspect of the disclosure relates to a robotic system for performing all-optical EP measurements (e.g., a fully robotic system). The system may be capable of automated: deposition of bio-photonic devices, maintenance of samples, introduction of fluorescent reporters, and/or treatment with external compounds. The system may be controlled remotely. The system may employ use of commercially available robotic deposition systems. The system may be contained within an external housing unit.

Another aspect of the disclosure relates to software for automated control of the device and/or software for automated analysis of the results. Yet another aspect of the disclosure relates to methods for using the energy lowering entities to allow for low powered light sources to be used. Yet another aspect of the disclosure relates to methods employing the devices, software, and methods for performing HT EP screening for: drug-ion channel interactions, cardiotoxicity screening, and/or cell phenotyping.

Another aspect of the disclosure is directed to a solid-state system for a temporally multiplexed all-optical dynamic electrophysiology scope (see, e.g., FIG. 22). In some embodiments, an on-axis optical dynamic electrophysiology system can include at least three solid-state, digitally controlled light sources, such as LEDs and/or solid-state lasers. The light sources may be capable of fast switching (>200 Hz). The light sources may have wavelengths in the near UV (100-400 nm), visible (400 nm-750 nm), and/or near infrared (750 nm-1,550 nm). An on-axis optical dynamic electrophysiology system can include at least one solid-state detector (e.g., CMOS, EMCCD, CCD, etc.). The solid-state detector may be capable of frame-rates greater than about 200 Hz. The solid-state detector may provide digital pulses synced with each frame. The solid-state detector may have at least 64×64 pixels. An on-axis optical dynamic electrophysiology system can include one or more of the following dichroic mirrors: one dichroic mirror for each light source to combine on to a single, on-axis optical path; and/or a single dichroic mirror capable of directing all illumination paths to the sample through the imaging lens and then pass all the imaging paths to the detector simultaneously. An on-axis optical dynamic electrophysiology system can include an imaging objective that can be at least one of a standard microscope objective or a GRIN™ objective.

In certain embodiments, the optical path of the on-axis optical dynamic electrophysiology system can be directed via free-space, optical fibers, a single unit comprised of fused GRIN lenses and dichroic beam splitters, or any combination thereof. The optical path can be considered "on-axis" where: all illumination light paths for sensing and actuation are combined onto a single light path prior to coupling into the imaging objective; all sensing/imaging light paths follow the same light path of the illumination light prior to being separated by a dichroic beam splitter; or light paths are separated and combined using dichroic beam splitters.

In various embodiments, the on-axis optical dynamic electrophysiology system can be scaled such that it is incorporated into an existing optical system such as a microscope or microendoscope. In various other embodiments, the on-axis optical dynamic electrophysiology system can be scaled such that it is operated in a parallel array or multiplexed array to provide simultaneous imaging over a multi-well plate.

The on-axis optical dynamic electrophysiology system may be capable of recording one or both of the following signals relevant to electrophysiology: 1) optogenetic sensors or synthetic dyes capable of fluorescently reporting intracellular calcium, membrane potential, and/or presence of other ions relevant to electrophysiology and 2) mechanical contraction.

In some embodiments, the on-axis optical dynamic electrophysiology system may be capable of quasi-simultaneous recording using a single detector by temporally multiplexed imaging obtained by TTL control of sensing LEDs such that: a single LED is active for each camera frame; each camera frame records a single recording channel (i.e., parameter), and/or the system sequentially cycles through each LED. In certain embodiments, the on-axis optical dynamic electrophysiology system may be capable of quasi-simultaneous recording using a single detector by employing a dichroic mirror capable of reflecting all sensing and actuation light paths to the sample and passing all recording light paths to the camera.

The on-axis optical dynamic electrophysiology system may be configured for all-optical electrophysiology by employing separate LEDs for optical actuation of the sample using: genetically encoded ion channels capable of controlling cellular membrane potential or release of intracellular calcium; and/or other bio-photonic devices capable of providing optical control of the cellular membrane potential. The on-axis optical dynamic electrophysiology system may be configured for all-optical electrophysiology by simultaneously providing temporally multiplexed imaging as described above.

The on-axis optical dynamic electrophysiology system can combine optical imaging (i.e., fluorescent and bright field) with optogenetic actuation. Furthermore, the on-axis optical dynamic electrophysiology system can be a complete optical system that is integrated into a fiber-optic based system for microendoscopic access or a stand-alone parallelized system for HT electrophysiology.

As will be understood by one of ordinary skill in the art, each embodiment disclosed herein can comprise, consist essentially of, or consist of its particular stated element, step, ingredient, or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples or exemplary language (e.g., "such as") provided herein is intended merely to better illuminate the disclosure and does not pose a limitation on the scope of the disclosure otherwise claimed. No language in the specification should be construed as indicating any non-claimed element essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless in cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Human iPS-Cardiomyocyte Culture and Gene Delivery

Frozen human iPSC-derived CMs (ICELL® Cardiomyocytes[2] CMC-100-012-001, CELLULAR DYNAMICS INTERNATIONAL™, Madison, Wis.) were thawed per the manufacturer's instructions. The cells were plated at the recommended plating density of 156,000 cells/cm$^2$ on fibronectin-coated 96-well glass-bottom plates. In some experiments, cells were grown in three-dimensional microgrooved scaffolds. These fibronectin-coated PDMS (SYLGARD® 184, DOW CORNING®, Midland, Mich.) scaffolds with microtopographical features (see FIG. 16, panel "e," peak-to-peak 120 µm, depth of 50 µm) were produced by molding onto metal templates fabricated by acoustic micromachining (see Entcheva, E. et al. *Lab Chip* 5, 179-183, (2005); Chung, C. Y. et al. *FASEB journal: official publication of the Federation of American Societies for Experimental Biology* 25, 851-862, (2011); and Chung, C. Y., et al. *J Cardiovasc Electrophysiol* 18, 1323-1329, (2007)); and small circular microgrooved scaffolds were punched-out and placed in the 96-well plates. After two days, adenoviral delivery of ChR2(H134R) to the iPSC-CMs was performed in-dish, similar to that used for generation of primary rat ChR2-CMs (see details below). The maintenance medium was replaced with viral doses of multiplicity of infection (MOI) 10, 15, 50, 100, 250, 500, and 1,000 prepared in OPTI-MEM™ (GIBCO®). Cells were incubated (37° C., 5% $CO_2$) and gently agitated every 20 minutes for a total of two hours, after which cells were returned to the maintenance media. Functional and structural testing was then performed two days after viral delivery to determine the optimal MOI.

Example 2—Primary Cardiomyocyte Isolation and Culture

Primary CMs were used through the study for all illustrative experiments with pharmacological treatments, mainly because at the current stage, they are perceived as more mature than the hiPSC-CMs and their response to drugs has been better documented. Briefly, neonatal (2-3 day old) SPRAGUE-DAWLEY® rats were sacrificed and ventricular tissue was removed per an approved Stony Brook University IACUC protocol. The tissue was digested overnight at 4° C. using 1 mg/mL trypsin (US BIOCHEMICALS®, Cleveland, Ohio) in Hanks' Balanced Salt Solution (HBSS, GIBCO® INVITROGEN™, Carlsbad, Calif.). The next morning, the tissue was serially digested using 1 mg/mL collagenase (WORTHINGTON BIOCHEMICAL®, Lakewood, N.J.) in HBSS at 37° C. and pipetted into conical tubes and placed on ice. After centrifugation, cells were re-suspended in culture medium M199 (GIBCO®) supplemented with 12 µM L-glutamine (GIBCO®), 0.05 µg/mL penicillin-streptomycin (MEDIATECH CELLGRO™, Kansas City, Mo.), 0.2 µg/mL vitamin $B_{12}$ (SIGMA ALDRICH®, St. Louis, Mo.), 10 mM HEPES (GIBCO®), 3.5 mg/mL D-(+)-glucose (SIGMA ALDRICH®), and 10% fetal bovine serum, FBS (GIBCO®). Fibroblasts were removed via a two-step pre-plating process, where the cell suspension was plated in a flask and incubated (37° C., 5% $CO_2$) for 45-60 minutes and switched to a new flask and the incubation repeated. CMs were then counted using a hemocytometer prior to plating in glass-bottom 96-well plates (see Jia, Z. et al. *Circulation. Arrhythmia and electrophysiology* 4, 753-760, (2011) and Chung, C. Y., et al. *J Cardiovasc Electrophysiol* 8, 1323-1329, (2007)).

Example 3—Gene and Cell Delivery for Optogenetic Actuation

Introduction of the optogenetic actuator was performed via direct gene delivery into CMs using an adenovirus (ChR2-CM) (see Williams, J. C. et al. *PLoS Comput Biol* 9, e1003220, (2013) and Ambrosi, C. M. et al. *Methods Mol Biol* 1181, 215-228, (2014)) or via "spark" cells (here an in-house developed stable ChR2-HEK293 cell line was used; other light-sensitized somatic cells can be used as well), based on a variation of the "tandem-cell-unit" (TCU) concept (see Jia, Z. et al. *Circulation. Arrhythmia and electrophysiology* 4, 753-760, (2011)). Through the text, for the general HT implementation of OptoDyCE, especially involving directly infected ChR2-CMs, OptoHTS is used, while for the specific implementation with "spark" cells sOptoHTS is used.

Adenoviral delivery of ChR2(H134R) to primary CMs was performed in suspension (see Ambrosi, C. M. et al. *Methods Mol Biol* 1181, 215-228, (2014)). Briefly, the plasmid pcDNA3.1/hChR2(H134R)-EYFP was used (ADDGENE™, Cambridge, Mass.; deposited by Dr. K. Deisseroth) (see Zhang, F. et al. *Nature* 446, 633-639, (2007)), to develop an adenoviral construct (pBR322 backbone) with a ubiquitous CMV promoter. First-generation adenovirus was generated by homologous recombination of the Ad-CMV-ChR2-eYFP into pTG3604; further propagation and purification of the virus genomes was done by transfection into HEK293 cells and CsC1 banding. CMs were re-suspended in 2% FBS M199 after counting and diluted to 1.125×10$^6$ cells/mL and infected using an optimized MOI of 15 for two hours in an incubator (37° C., 5% CO$_2$) with gentle agitation every 20 minutes. The MOI had been optimized during preliminary experiments to achieve >95% ChR2 expression in CMs within 48 hours using titer of 10$^{12}$ units/mL diluted in PBS, confirmed by eYFP reporter visualization and minimal cell death (by propidium iodide staining) (see Ambrosi, C. M., et al. *Prog Biophys Mol Biol* 115, 294-304, (2014) and Ambrosi, C. M. et al. *Methods Mol Biol* 1181, 215-228, (2014)). After two hours, the cell suspension was centrifuged and culture medium was removed and replaced with fresh 10% FBS M199 for plating (see Ambrosi, C. M. et al. *Methods Mol Biol* 1181, 215-228, (2014)).

The cell delivery approach employs "spark" cells (ChR2 (H134R)-HEK293), a stable cell line showing near 100% expression of ChR2. "Spark" cells were developed by transfecting HEK293 cells (CRL-1573™ ATCC®, Manassas, Va.) with the ChR2 plasmid pcDNA3.1/hChR2(H134R)-EYFP using LIPOFECTAMINE® 2000 (INVITROGEN™, Carlsbad, Calif.). ChR2-expressing cells were then selected by the application of 500 μg/mL geneticin (INVITROGEN™) (see Jia, Z. et al. *Circulation. Arrhythmia and electrophysiology* 4, 753-760, (2011)). Prior to use, the ChR2-HEK cells were grown at 37° C., 5% CO$_2$ in Dulbecco's Modified Eagle's Medium (DMEM; GIBCO® INVITROGEN™) supplemented with 10% FBS and 1% penicillin-streptomycin. After trypsinization, the cells were delivered by one of two methods during plating: co-culture, where the cells were mixed with CMs at the time of plating, or "sprinkling" of "spark" cells on top of already plated CMs 24 to 48 hours prior to experiments.

Example 4—Cell Plating

For all cell conditions, 50 μg/mL fibronectin, diluted in PBS, was used on 96-well glass-bottom plates (IN VITRO SCIENTIFIC™) and incubated at 37° C. for at least two hours prior to cell plating. Cells were plated in 10% FBS M199 media; on day two, the media was replaced with 2% FBS M199 until the day of experiments.

Non-infected control CMs and ChR2-CM cells (for OptoHTS) were plated using a concentration of 1.125×10$^6$ cells/mL to achieve a plating density of 470,000 cells/cm$^2$. For CM/ChR2-HEK co-cultures, CMs at a concentration of 1.125×10$^6$ cells/mL were mixed in a conical with trypsinized ChR2-HEK cells, pre-diluted to achieve ratios 150:1 CM to ChR2-HEK. After centrifugation, the media was removed and the cells were re-suspended in fresh 10% FBS M199 to achieve the same density of plating as the control CMs.

ChR2-HEK cell "sprinkling" (for sOptoHTS) was performed by exchanging culture media of already plated CMs with a cell suspension of "spark" ChR2-HEK cells, diluted to achieve ratios of 75:1 CM to ChR2-HEK cells. In this approach, the CMs were diluted to either 1.075×10$^6$ cells/mL and cultured for several days. 48 hours prior to experiments, ChR2-HEK cells were trypsinized and diluted in 2% FBS M199 to achieve the desired plating ratios at the required volume for a media exchange. Media in the dishes containing CMs was then removed and replaced with the ChR2-HEK cell suspension.

Example 5—Automated all-Optical Electrophysiology

All functional experiments were carried out 4-5 days after cell plating, at room temperature in Tyrode's solution containing the following (in mM): NaCl, 135; MgCl$_2$, 1; KCl, 5.4; CaCl$_2$, 1.5; NaH$_2$PO$_4$, 0.33; glucose, 5; and HEPES, 5 adjusted to pH 7.4 with NaOH (see Chung, C. Y., et al. *J Cardiovasc Electrophysiol* 18, 1323-1329, (2007)). The optical setup (see FIG. 16, panels "i" and "j") was built around an inverted microscope (NIKON® ECLIPSE™ TE-2000-U) fitted with a programmable x-y stage (OPTISCAN™ ES107; PRIOR SCIENTIFIC™; Rockland, Mass.) and automated z-focus (PS3H122™ Motorized Focus; PRIOR SCIENTIFIC™). Illumination for optical actuation and sensing was provided by TTL-programmable LEDs coupled into the system using a custom-built adapter. Optical actuation of ChR2 was provided by an LED, a 470 nm, 650 mW LED (THORLABS™; Newton, N.J.), controlled by an LED driver (THORLABS™), and fitted with a 470/28 nm bandpass filter, $F_{actu}$.

The components of the optical sensing light path were selected based on the optical sensor. Voltage measurements, $V_m$, were recorded using the synthetic voltage-sensitive dye Di-4-ANBDQBS39 (from Leslie Loew, University of Connecticut) with fluorescence excitation and emission peaks at 660 nm and >700 nm, respectively. Rhod-4™, AM (AAT BIOQUEST®, Sunnyvale, Calif.) with fluorescence excitation and emission peaks at 530 nm and 605 nm, respectively, was used for intracellular calcium, $[Ca^{2+}]_i$ recording.

Illumination for sensing was provided by sLED ($V_m$: 640 mW LED at 660 nm; or $[Ca^{2+}]_i$: 350 mW LED at 530 nm, both from THORLABS™), fitted with a bandpass filter $F_{ex}$ ($V_m$: 655/40 nm; or $[Ca^{2+}]_i$: 535/50 nm). The light paths for optical sensing and actuation were combined by a dichroic mirror DM1 (495 nm long-pass) and directed to the sample by DM2 ($V_m$: 685 nm long-pass; $[Ca^{2+}]_i$: 565 nm long-pass). Collimation optics comprised of several lenses (L), and an objective lens (in this case 20× NIKON® CFI SUPER PLAN FLUOR™) was used to direct light to the sample. Emitted fluorescence was collected by the objective lens and passed through DM2 and a band-pass emission filter $F_{em}$ ($V_m$: 700 nm long-pass; $[Ca^{2+}]_i$: 605/70 nm bandpass) to a photodetector (in this case, IXON ULTRA 897 EMCCD™; ANDOR™ TECHNOLOGY LTD., Belfast, UK).

The main experiments were carried out using 96-well plates, automated as shown in FIG. 16, panels "i" and "j." The stage was programmed to traverse each well (x-y coordinate), auto-focus (z) on the sample under constant fluorescent illumination and then record for 5-20 seconds, based on the desired optical pacing protocol. The optical pacing LED was controlled via TTL to deliver the desired pacing protocol, and the optical sensing LED was constantly on, while the camera was programmed to record only during the pacing. This protocol was repeated for each well over the entire dish. If needed, fluorescent images of the dye and of eYFP of the actuator were also recorded using an automated protocol. After recording, intensity values over time averaged over the full FOV or extracted per region were exported for post-processing.

Example 6—Optical Pacing and Optical Recording

Optical recording of membrane voltage, $V_m$, was performed using the synthetic voltage-sensitive dye Di-4-ANBDQBS, spectrally-compatible with ChR2. Briefly, a 17.5 mM stock solution in pure ethanol was diluted to 35 μM in Tyrode's solution. Cells were stained for six minutes in dye solution followed by a six minute wash in fresh Tyrode's solution. This wash solution was then replaced by fresh Tyrode's solution. Intracellular calcium, $[Ca^{2+}]_i$, was recorded using QUEST RHOD-4™, AM diluted from a 0.5 mM stock solution dissolved in DMSO with 20% PLURONIC® to 10 µM in Tyrode's solution. Samples were stained with this solution for 20 minutes, followed by a 20 minute wash in fresh Tyrode's solution, and finally a replacement with fresh Tyrode's solution before experiments.

Optical imaging was performed at >200 frames per second (fps) with 4×4 binning using NIS-ELEMENTS AR™ (NIKON® INSTRUMENTS; Melville, N.Y.). Optical stimulation (470 nm) was provided at pulse lengths of 5-20 ms, at 0.5-8 Hz, using irradiances of 0.4-7 mW/mm$^2$, as needed. Electrical stimulation (for comparing electrical versus optical stimulation) was delivered through a pair of parallel platinum electrodes connected to a pulse generator (IONOPTIX™, Milton, Mass.) providing 5 ms 10 V bipolar pulses at 0.5-2 Hz. Example data illustrating the dynamic capabilities of the OptoDyCE system are illustrated in FIG. 21. Both $V_m$ (top) and $Ca^{2+}$ (bottom) recordings were obtained from samples plated on 96-well pates and were paced at frequencies of 1, 2, and 3 Hz.

Comparison of electrical pacing of control CMs (without gene or cell delivery of ChR2) to optical and electrical pacing of ChR2-CM and CM/ChR2-HEK cells was carried out on 14-mm glass bottom dishes. Multiple FOVs were taken per dish, and each recording was divided into smaller ROI and intensity data over time was extracted and analyzed. Contractions were measured by post-processing of recorded videos and tracking cell motion (displacement) by naturally occurring cell heterogeneities (fiducial markers).

Example 7—Immunocytochemistry

To confirm ChR2 expression (in the primary rat CMs, in the CM/ChR2-HEK co-cultures, and the iPS-CMs) and to confirm myocyte-like properties of IPS-CMs, antibody staining and confocal imaging was performed (see FIGS. 5A, 5B, and 16, panels "a" and "c"), using the OLYMPUS™ FLUOVIEW™ FV1000 confocal system. Samples were fixed in 3.7% formaldehyde after performing functional experiments. Prior to antibody labelling, cell membrane permeabilization was performed by incubating samples in 0.02% TRITON™ X-100 for five minutes. Cells were labelled with mouse anti-α-actinin primary antibody (SIGMA ALDRICH®, A-7811) at 1:600 and ALEXA FLUOR® 647 goat anti-mouse IgG secondary antibody (INVITROGEN™, A-21235) at 1:1000. All antibodies were diluted using 1% bovine serum albumin (AMERSHAM™ PLC, Amersham, UK). 1% FBS was used as a blocking agent. After antibody staining, cell nuclei were stained with 1 µg/mL DAPI with 10 minute incubation in PBS. Imaging was done using the OLYMPUS™ FLUOVIEW™ FV1000 confocal system with acquisition rate at 4 µs/pixel. Gain was kept constant for control and test groups to normalize and exclude autofluorescence contributions.

Example 8—Drugs

Nifedipine (MW 346.33 g/mol; SIGMA ALDRICH®) concentrations of 50 µM, 10 µM, 5 µM, 1 µM, 0.5 µM, 0.1 µM, 0.05 µM, 0.01 µM, 0.005 µM, 0.001 µM, and 0.0001 µM were prepared in Tyrode's solution. A stock solution of 100 mM in DMSO was serially diluted in DMSO and then Tyrode's solution to the final concentrations. Dofetilide (MW 441.56 g/mol; FISHER™) concentrations of 2 µM, 0.2 µM, and 0.02 µM were prepared in Tyrode's solution. A stock solution of 200 mM in DMSO was prepared and serially diluted in DMSO and then Tyrode's solution to the final concentrations. DMSO was not seen to have an effect on APD at the used concentrations (<1% DMSO; see FIG. 13). Drug doses were dispensed manually after staining and washing and before experiments. Measurements were completed within 20-50 minutes after drug application, assuming steady-state of action.

Example 9—Data Processing and Analysis

Data was analyzed using custom developed HT software in MATLAB®, flashligHTS (see FIG. 11). The software was used to automatically extract "events" from recorded traces, i.e., APs and CTs, as well as to quantify certain morphological features of these events, while keeping track of wells (samples) and spatial locations (or ROIs). Data pre-processing included baseline correction, removal of artifacts, temporal filtering using a Savitzky-Golay polynomial filter (second order, 7-11 frame window) and normalization. All traces are reported in terms of percent change of fluorescence from baseline ($\Delta F/F$) and normalized percent $\Delta F/F$. All normalized example APs and CTs were averaged over 6-10 beats of filtered traces. Action potential durations (APDs) and calcium transient durations (CTDs) at 25%, 50%, and 80% were automatically extracted and defined as the time difference between the onset of an AP/CT and the point of 25%, 50%, and 80%, respectively, return to baseline. Contractions were quantified by video post-processing and expressed as relative displacement (in % length change). Phase maps to capture wavefront irregularities and localized abnormal activations (as shown in FIGS. 9A-9C) were constructed using the Hilbert transform, as described previously (see Entcheva, E. et al. *Prog. Biophys. Mol. Biol.* 92, 232-257 (2006)).

Data are presented in terms of mean±SEM. For drug dosing experiments, APD/CTD data for each group are calculated by finding the average APD/CTD for each well (usually 6-10 beats). All averaged APD/CTDs for each well for a condition (e.g., drug dose) are then averaged and the SEM is calculated. $\Delta$APD/CTD (%) is given as the percent change of this calculated average from the average of the control group (e.g., no drug). SEM is calculated by appropriately propagating the SEM from each group. Data combined over different cultures is only given in terms of $\Delta$APD/CTD (%). Here, for each run, the $\Delta$APD/CTD (%) is calculated with respect to the average control APD/CTD (over all control wells). These normalized $\Delta$APD/CTD (%) for each well are then combined across all runs and averaged.

Variations within a sample (temporal variation of events or spatial variation of events within the FOV) are quantified using the MAD as a measure of variability. MAD is calculated by taking the median of the absolute deviations from the data's median (see Equation 1) for APD25/50/80 or CTD25/50/80 for each sample and then averaged across samples.

$$MAD = median_i(|X_i - median_j(X_j)|) \qquad \text{Equation 1}$$

Statistical comparison of OptoHTS and sOptoHTS APDs was performed in MATLAB® using an ANOVA test followed by a Tukey-Kramer post hoc correction for multiple comparisons. Values of p<0.01 were considered statistically significant.

Example 10—Computational Analysis of Optogenetic Sensors and Actuators

Computational modeling of ChR2(H134R) action in human ventricular myocytes (see ten Tusscher, K. H. et al American journal of physiology. Heart and circulatory physiology 291, H1088-1100, (2006)), shown in FIGS. 7A and 15, panels "b"-"g," was performed in MATLAB®. Briefly, a four-state model of ChR2 with non-linear voltage and light dependence was integrated into a human ventricular cardiac model (see Williams, J. C. et al. PLoS Comput Biol 9, e1003220, (2013) and Williams, J. C. et al. Biophys J 108, 1934-1945, (2015)). To simulate a reduced expression or purported drug inhibitory action, we reduced the ChR2 conductance by 70%; while "drug, extreme" action was modeled by 70% reduced conductance and 95% slowing of Gd1 and Gd2 transition rates in the ChR2 state model (see FIG. 15, panels "b"-"f"). Irradiance was adjusted/increased to trigger a response in FIG. 15, panels "c"-"f" under the abnormal conditions. The action of the optogenetic voltage sensor VSFP2.3 in human ventricular myocytes was simulated using a state model of VSFP2.3 (see Akemann, W., et al. Biophys J 96, 3959-3976, (2009)). In FIG. 15, panel "g," VSFP-$V_m$ reports the fluorescence measured in a human ventricular myocyte. The "20% slowing" case was simulated by using a 0.8 scaling of all OFF rate constants in the model, and the "50% slowing" case was simulated by using a 0.5 scaling factor of all OFF rate constants (see Akemann, W., et al. Biophys J 96, 3959-3976, (2009)).

To simulate conditions in the "spark" OptoHTS approach, we used a human ventricular myocyte model (see ten Tusscher, K. H. et al. American journal of physiology. Heart and circulatory physiology 291, H1088-1100, (2006)), coupled to fibroblast(s) (see MacCannell, K. A. et al. Biophys J 92, 4121-4132, (2007)), modified to express ChR2 (see Williams, J. C. et al. PLoS Comput Biol 9, e1003220, (2013)). Multiple light-sensitive fibroblasts could be coupled to a CM to capture the electronic effects they have on APD, as shown in FIG. 7A. The effects of HEK cells would be qualitatively similar to the modelled fibroblasts, in the sense that they are both electrically passive cells with more depolarized resting membrane potential than the CMs.

Example 11—Spectral Considerations

Optical recording primarily involves two classes of synthetic fast fluorescent dyes: voltage and intracellular calcium. One of the key challenges to designing an all-optical electrophysiology system is minimizing spectral overlap of actuators (entities driving or suppressing cell activity) and sensors (fluorescent reporters that undergo spectral shifts in response to physiological changes). Commonly used voltage sensors include the styryl dyes, such as the blue-green excited Di-8-ANEPPS, which are not particularly efficient and overlap spectrally with the wavelengths of commonly used optogenetic actuators such as ChR2. More recently, new near-infrared dyes (650 nm), such as di-4-ANBDQBS (spectrum in FIG. 20A), have provided a means of further spectral separation from actuators. Calcium dyes are also of particular interest, due to the link between electrical activity and intracellular calcium (see E. Entcheva, et al. Progress in biophysics and molecular biology, 92(2), 232-257, (2006) and T. J. Herron, et al. Circ Res, 110(4), 609-623, (2012)). Unlike potentiometric dyes, commonly used calcium dyes, such as Rhod-4™, AM (spectrum in FIG. 20A), have much stronger optical signals. However, their affinity for $Ca^{2+}$ is vital for accurate representation of the $Ca^{2+}$ transient; higher affinity dyes can result in artificially prolonged transient recordings (see E. Entcheva, et al. Progress in biophysics and molecular biology, 92(2), 232-257, (2006); T. J. Herron, et al. Circ Res, 110(4), 609-623, (2012); and I. R. Efimov, et al. Circ Res, 95(1), 21-33, (2004)).

For actuation, light-sensitive ion channels, such as the blue-wavelength excited (470 nm) depolarizing (excitatory) channel, ChR2 is used (see N. Smedemark-Margulies, et al. Frontiers in Molecular Neuroscience, 6, (2013) and A. M. Packer, et al. Nat Neurosci, 16(7), 805-815, (2013)). FIG. 20A shows the action spectrum for ChR2, as well as the excitation and emission spectra for two compatible optical sensors: the calcium-sensitive probe Rhod-4™, AM and the red-shifted voltage sensor Di-4-ANBDQBS. Many of these probes and actuators have broad absorption and emission spectra which can overlap causing issues with excitation and stimulation. For example, ChR2 has an intermediate deactivating green state at 520 nm after activation with blue light, meaning excitation light for dyes such as Rhod-4™, AM could potentially affect ChR2 kinetics (see C. Bamann, et al. Journal of Molecular Biology, 375(3), 686-694, (2008)); however, in the OptoDyCE system this has not been found to cause significant effects.

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

What is claimed is:

1. A method of testing an effect of a compound on the electrophysiology of a target cell, the method comprising:
exposing a cell culture to a compound, the cell culture comprising:
a target cell without genetic transformation to make it light-sensitive; and a bio-photonic device comprising:
  a non-biological cell body; and
  at least one of a photon-sensitive entity or a combination of a photon-sensitive entity and a photon-generating entity disposed in the non-biological cell body, wherein the bio-photonic device is configured to activate the target cell;
exposing the cell culture to photonic energy; and
measuring an electrophysiological signal in the target cell.

2. The method of claim 1, further comprising:
using at least one of a fluorescent reporter disposed in the cell culture or an optical phenomenon to measure the electrophysiological signal in the target cell.

3. The method of claim 1, wherein the electrophysiological signal is selected from at least one of a level of intracellular calcium, a membrane potential, a level of an electrophysiology-associated ion, or a mechanical contraction.

4. The method of claim 1, wherein the photonic energy is provided by an external source.

5. The method of claim 1, wherein the photonic energy is provided by an internal source.

6. The method of claim 5, wherein the internal source is a photon-generating entity disposed in the cell body.

7. The method of claim 1, wherein the photonic energy is provided in pulses, continuously, and/or at a desired frequency.

8. The method of claim 7, wherein the photon-sensitive entity is configured to induce a local electric field change and/or convert photons having a first energy to photons having a second energy.

9. The method of claim 8, wherein the photon-sensitive entity is selected from at least one of a chromophore or a combination of a chromophore and a nanoparticle.

10. The method of claim 8, wherein the local electric field change is configured to change a membrane potential of the target cell disposed adjacent the bio-photonic device.

11. The method of claim 7, wherein the photon-generating entity is configured to emit photons in the absence of external photons and wherein the emitted photons activate the photon-sensitive entity to induce a local electric field change.

12. The method of claim 11, wherein the local electric field change is configured to change a membrane potential of the target cell disposed adjacent the bio-photonic device.

13. The method of claim 7, wherein the photon-sensitive entity is configured to absorb photonic energy between about 100 nm and about 1,300 nm and wherein the photon-generating entity is configured to emit photonic energy between about 100 nm and about 1,300 nm.

14. The method of claim 7, wherein the non-biological cell body is a synthetic vesicle.

15. The method of claim 7, wherein the non-biological cell body is selected from at least one of a liposome or a bio-compatible encapsulated entity, and wherein the non-biological cell body contains at least one of a protein or a light sensitive structure configured to convert optical radiation to a local electric field change.

16. The method of claim 1, wherein the target cell is a cardiomyocyte.

17. The method of claim 1, wherein the cardiomyocyte is derived from at least one of an induced pluripotent stem cell or an embryonic stem cell.

18. The method of claim 1, wherein the method is a high-throughput method.

19. The method of claim 1, wherein the method is an automated method.

* * * * *